US010953051B2

(12) United States Patent
Lang et al.

(10) Patent No.: US 10,953,051 B2
(45) Date of Patent: Mar. 23, 2021

(54) METHODS AND MEANS FOR PROTECTING THE SKIN AGAINST PATHOGENIC MICROORGANISMS

(71) Applicant: Novozymes A/S, Bagsvaerd (DK)

(72) Inventors: Christine Lang, Berlin (DE); Andreas Hellmann, Berlin (DE); Markus Veen, Berlin (DE); Budde Eckhard, Berlin (DE); Mewes Boettner, Berlin (DE); Andreas Reindl, Mannheim (DE); Rolf Knoll, Laudenbach (DE)

(73) Assignee: Novozymes A/S, Bagsvaerd (DK)

( * ) Notice: Subject to any disclaimer, the term of this patent is extended or adjusted under 35 U.S.C. 154(b) by 34 days.

(21) Appl. No.: 16/010,106

(22) Filed: Jun. 15, 2018

(65) Prior Publication Data

US 2019/0381117 A1 Dec. 19, 2019
US 2020/0121741 A9 Apr. 23, 2020

Related U.S. Application Data

(63) Continuation of application No. 15/247,001, filed on Aug. 25, 2016, now abandoned, which is a continuation of application No. 14/082,881, filed on Nov. 18, 2013, now abandoned, which is a continuation of application No. 13/604,124, filed on Sep. 5, 2012, now abandoned, which is a continuation of application No. 11/921,497, filed as application No. PCT/EP2006/006030 on Jun. 22, 2006, now abandoned.

(60) Provisional application No. 60/740,084, filed on Nov. 28, 2005.

(30) Foreign Application Priority Data

Jun. 22, 2005 (EP) .................................. 05013494

(51) Int. Cl.
*A61K 35/747* (2015.01)
*A61K 9/00* (2006.01)
*A61P 31/04* (2006.01)
*A61K 9/19* (2006.01)
*A61K 35/00* (2006.01)

(52) U.S. Cl.
CPC .......... *A61K 35/747* (2013.01); *A61K 9/0014* (2013.01); *A61K 9/19* (2013.01); *A61P 31/04* (2018.01); *A61K 2035/11* (2013.01)

(58) Field of Classification Search
None
See application file for complete search history.

(56) References Cited

U.S. PATENT DOCUMENTS 6,270,811 B1  8/2001  Fregonese
7,090,840 B2  8/2006  Cho
7,510,734 B2 * 3/2009 Sullivan .................. A61K 8/99
                                                      424/780
7,651,680 B2 * 1/2010 Breton ..................... A61K 8/19
                                                      424/600
2009/0130073 A1 5/2009 Reindl et al.

FOREIGN PATENT DOCUMENTS

WO   1999007332 A2   2/1999
WO   2000071139 A2   11/2000
WO   2003080813 A2   10/2003

OTHER PUBLICATIONS

Aly et al, 1972, The journal of investigative dermatology 58(4), 205-21.
Annuk et al, 2003, J Appl Microbiol 94, 403-41.
Bisno et al, 1984, Am J Med 76(5A), 172-179.
Brook et al, 2000, Pediatr Dermatol 17(5), 360-363.
Elek, 1956, Annals of the New York Academy of Sciences 65, 85-90.
Falsen et al, 1999, Int J Syst Bacteriol 49(1), 217-221.
Feingold, 1985, Cutis 36(5A), 1.
Gfatter et al, 1997, Dermatology 195(3), 258-262.
Gibbons et al, 1975, Annual review of microbiology 29(1), 19-44.
Hurst, 1959, Pediatrics 25, 11-20.
Imokawa et al, 1986, The Society for in vestigative Dermatology 87(6), 758-761.
Korting et al, 1990, Acta derm venereol 70, 429-457.
Korting et al, 1992, International journal of hygiene and environmental medicine 193(1), 78-90.
Larson, 2001, Emerg infect diseases 7(2), 225-230.
Leyden et al, 1987, J Invest Dermator 88(3), 65-72.
Milyani et al, 1978, J Med Microbiol 11(4), 379-386.
Ocana et al, 1999, FEMS Immunology and medical microbiology 23(2), 87-92.
Ohnishi et al, 1999, Clinical and diagnostic laboratory immunology 6(1), 101-104.
Osman et al, 2003, Biosis access No. PREV200300522983.
Osman et al, 2003, Turkish journal of biology 27(3), 131-136.
Ouwehand et al, 2003, Lett Appl Microbiol 36, 327-331.
Roth et al, 1988, Annual review of microbiology 42(1), 441-464.
Selwyn et al, 1972, Br Med J 1(793), 136-140.
Sullivan et al, 2001, Lancet infect diseases 1(2), 101-114.
Yosipovitch et al, 1996, Cosmetics toiletries magazine 111(12), 101-102.

* cited by examiner

*Primary Examiner* — Vera Afremova
(74) *Attorney, Agent, or Firm* — Eric J. Fechter

(57) ABSTRACT

Described are microorganisms which are, in a first aspect, able to to stimulate the growth of microorganisms of the resident skin microbial flora and which do not stimulate the growth of microorganisms of the transient pathogenic micro flora. In a second aspect microorganisms are described which are able to inhibit the growth of microorganisms of the transient pathogenic skin micro flora and which do not inhibit the growth of microorganisms of the resident skin micro flora. Also described are compositions comprising such microorganisms as well as the use of such microorganisms in cosmetic, prophylactic or therapeutic applications.

19 Claims, 11 Drawing Sheets

FIGURE 10
FIGURE 10A
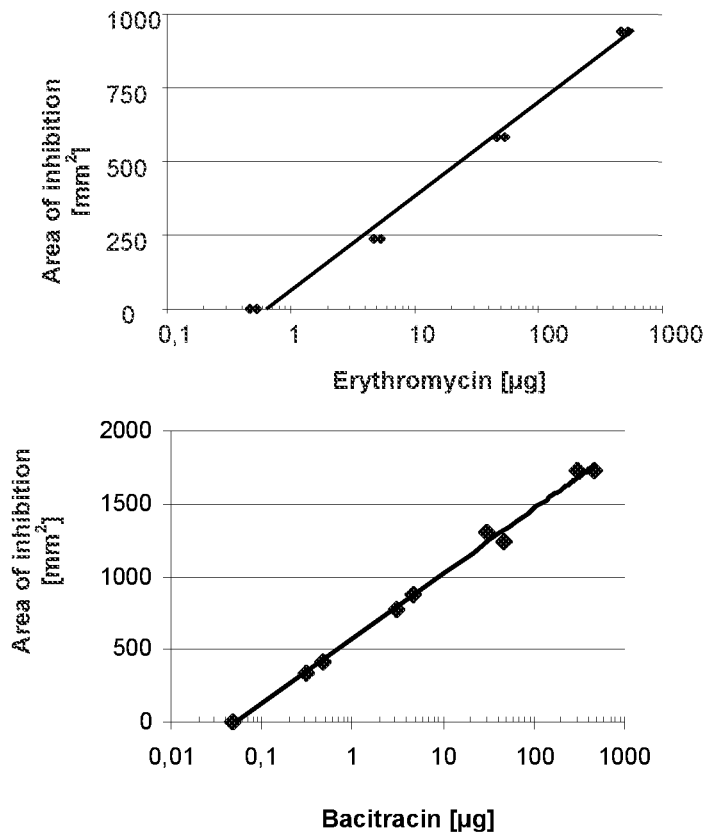
FIGURE 10B
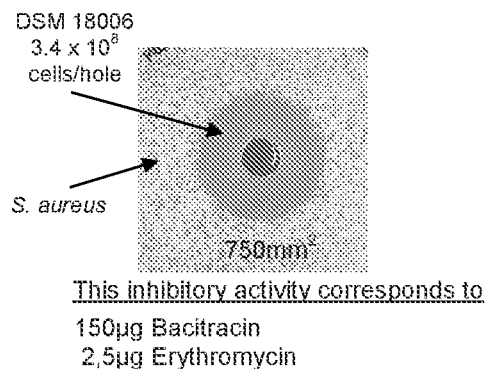

METHODS AND MEANS FOR PROTECTING THE SKIN AGAINST PATHOGENIC MICROORGANISMS

CROSS-REFERENCE TO RELATED APPLICATIONS

This application is a continuation of U.S. application Ser. No. 15/247,001, filed Aug. 25, 2016, which is a continuation of U.S. application Ser. No. 14/082,881, filed Nov. 18, 2013, which is a continuation of U.S. Application Ser. No. 13/604,124 filed Sep. 5, 2012, which is a continuation of U.S. application Ser. No. 11/921,497, filed Jul. 9, 2009, which is a national stage application (under 35 U.S.C. 371) of PCT/EP2006/006030 filed Jun. 22, 2006, which claims benefit of European application 05013494.9 filed Jun. 22, 2005, and U.S. Provisional application 60/740,084 filed Nov. 28, 2005. The entire content of each aforementioned application is hereby incorporated by reference in its entirety.

The present invention relates to microorganisms which are able to stimulate the growth of microorganisms of the resident skin microbial flora and which do not stimulate the growth of microorganisms of the transient pathogenic micro flora. The present invention also relates to compositions, comprising such microorganisms, e.g. cosmetical or pharmaceutical compositions and to the use of such microorganisms in cosmetic, prophylactic or therapeutic applications.

The human skin is populated by a large variety of microorganisms that mainly live as commensals in a relatively stable composition on the surface of the skin (Roth and James, 1988). This normal skin flora is termed "resident skin flora".

The main function of the human skin is to protect the tissue beneath it against the environment (Feingold, 1985). This normal skin flora especially protects the skin against the intrusion of potentially pathogenic microorganisms (Bisno, 1984). Certain microorganisms dominate the resident microbial flora. More than ninety percent of the microorganisms of the resident microbial flora are *Staphylococcus epidermidis* (coagulase negative), *Micrococcus* spec., Diphteroids and propionibacteria (Leyden et al., 1987). Therefore, a stabilisation of the natural skin flora supports the protection of the skin and prevents the intrusion of pathogens. The health of the skin increases. The importance of the natural skin flora has been described in several clinical studies. It has been shown that in the first days after birth of an infant, where this skin flora has not yet been developed, the danger of a *Staphylococcus aureus* infection is very high. With increasing development of the flora, the skin is protected from the colonization by pathogenic microorganisms (Hurst, 1959). In another study with infants, it has been observed that after treatment with the antibiotic amoxicillin, the resident flora was drastically (about 50%) repressed. This led to more than a fourteen-fold increase of the pathogenic yeast *Candida albicans*. The discontinuation of the antibiotic treatment led to a regeneration of the resident flora and the repression of *Candida albicans* (Brook, 2000).

The microorganisms of the resident skin flora prevent the colonization by pathogenic microorganisms by competing for attachment sites and essential nutrients on the skin surface (Sullivan et al. 2001). Pathogenic microorganisms are able to specifically attach to structures of the epidermis using special binding proteins. In this context, different mechanisms are known. From *Staphylococcus aureus*, for example, specific adhesins are known. These allow the pathogenic microorganism to attach to fibronectin structures. Pathogens generally have a higher potential to attach to the host. This explains the virulence of these microorganisms (Gibbons and Houte, 1975).

The danger of colonization by pathogenic microorganisms increases drastically in the case of small lesions or other damages on the surface of the skin, especially when the normal skin flora is damaged by antibiotics or by excessive washing (Elek, 1956). However, the resident skin flora is better adapted to the skin regarding nutrient utilisation. This leads to an advantage of the resident skin flora (Larson, 2001). Apart from this, the organisms of the resident skin flora are able to produce antimicrobial substances to fight against pathogenic microorganisms. This is also an advantage for resident microorganisms regarding nutrients and energy sources (Selwyn and Ellis, 1972; Milyani and Selwyn, 1978).

Moreover, substances that are secreted by the skin, like complex lipids (triglycerides), are degraded to unsaturated fatty acids that inhibit pathogenic microorganisms like *Streptococcus pyrogenes* or gram negative bacteria and fungi (Aly et al., 1972).

The microbial skin flora affects several factors of the skin that are of cosmetic relevance. These are pH value of the skin, barrier function and lipid content. *S. epidermidis* is able to fight against pathogenic microorganisms by lowering the pH value (about 4-6). Pathogens are not able to grow at decreased pH values (Korting et al., 1990; Lukas, 1990; Korting, 1992; Yosipovitch and Maibach, 1996; Gfatter et al., 1997).

The water barrier function and the lipid content of the skin depend on the ceramide content of the horny layers (Imokawa et al., 1986). Lowering of the ceramide content causes a drying and rifting of the skin. A study with atopical dermatitis patients having these appearances of the skin showed that the microbial skin flora dramatically changes to *Staphylococcus aureus*. This pathogen features a very high ceramidase activity, while normal commensals of the resident skin flora do not have this activity. Sphingomyelinase activities that lead to the release of ceramides in the skin are comparable in the resident and pathogenic flora of atopic dermatitis patients (Ohnishi et al., 1999).

Thus, there is a need for means and methods allowing to protect the skin, in particular the human skin, against pathogenic microorganisms.

The present invention addresses this need and provides microorganisms and methods which protect the skin against the colonization by pathogenic microorganisms. In particular, it provides the embodiments as characterized in the claims.

Accordingly, the present invention in a first aspect relates to a microorganism which is able to stimulate the growth of one or more microorganisms of the resident skin microbial flora and which does not stimulate the growth of microorganisms of the transient pathogenic micro flora.

The inventors surprisingly found that an effective protection of the skin against a colonization by pathogenic microorganisms can be achieved by administering to the skin the above described microorganisms or inactivated forms thereof. The inventors for the first time identified corresponding microorganisms and provided methods for their identification. These microorganisms are able to regenerate and to stabilize the natural skin flora due to a specific stimulation of the growth of microorganisms of the resident skin microbial flora. By this, the growth of pathogenic microorganisms is suppressed. Furthermore, the entrance of pathogenic microorganisms into the skin microbial flora can be prevented. The microorganism of the present invention allow, e.g., to stimulate the resident microbial flora in deeper horny layers of the skin when microorganisms in the upper layers of the skin have been removed by washing.

Many different microorganisms exist on the skin. Some belong to the normal (resident) flora of the skin and are harmless commensals and some are potential pathogens.

Basically, organisms on the skin can be classified into two categories:
1. Resident organisms: resident organisms are permanent inhabitants of the skin which colonise on the surface of the skin, the stratum corneum and within the outer layer of the epidermis and the deeper crevices of the skin and hair follicles. These microorganisms of the resident microbial skin flora can grow and multiply on the skin without invading or damaging the skin tissue. Washing does not easily remove these organisms in deeper skin regions. Resident microorganisms are harmless commensals.
2. Transient organisms: transient organisms are microorganisms which are deposited on the skin but do not multiply there or contaminants which multiply on the skin and persist for short periods. They cannot settle permanently on healthy skin whose microenvironment is heavily determined by the resident micro flora. Transient organisms are potentially pathogenic.

Thus, the term "resident skin microbial flora" relates to the microorganisms which can normally be found on healthy skin, preferably human skin, and which constitute the majority of the microorganisms found on the skin.

In particular, the term "resident skin microbial flora" relates to microorganisms which are permanent inhabitants on the surface of the skin, the stratum corneum and within the outer layer of the epidermis and the deeper crevices of the skin and hair follicles. These microorganisms are characterized in that they can grow and multiply on the skin without invading or damaging the skin tissue. A characteristic of these microorganisms is that washing does not easily remove them in deeper skin regions. The microorganisms of the resident skin microbial flora are harmless commensals.

The term "resident skin microbial flora" preferably relates to a flora of aerobic and anaerobic microorganisms which can be found on skin, preferably human skin. More preferably, it relates to a flora of microorganisms which comprises *Staphylococcus epidermidis* (coagulase negative), *Micrococcus* spec., Diphteroids and propioni bacteria. Typically, about 90% of the aerobic resident microbial skin flora consists of *Staphylococcus epidermidis*. The remaining about 10% are composed of mainly *Micrococcus* spec. (80% *Micrococcus luteus*) and Diphteroids (13%). The term "Diphtheroid" denotes a wide range of bacteria belonging to the genus *Corynebacterium*. For convenience, cutaneous diphtheroids have been categorized into the following four groups: lipophilic or nonlipophilic diphtheroids; anaerobic diphtheroids; diphtheroids producing porphyrins. Major representatives (90%) of the anaerobic microbial skin flora are propionibacteria; especially *Propionibacterium acnes, P. granulosum* and *P. avidum* can be isolated from the skin. The anaerobic flora accounts for approximately 4% of the total resident skin flora.

More preferably, more than 90% of the microorganisms of the microbial flora belong to *Staphylococcus epidermidis, Micrococcus* spec., Diphteroids and propioni bacteria. Even more preferably, the resident skin microbial flora is characterized in that its major constituent is *Staphylococcus epidermidis*.

The constituents and the composition of the microbial skin flora can be determined quantitatively and qualitatively, e.g. by peeling off the upper skin layers with scotch tape. Microorganisms of the resident skin microbial flora can be identified within the upper ten skin layers peeled off, e.g., by scotch tape. Exemplary, to isolate these microorganisms six 2 cm$^2$ scotch tapes are each pressed on a defined region of the skin, preferably of the forearm and afterwards each tape stripe is transferred from the skin to a selective culture agar plate for either gram positive (e.g. BHI, Difco Inc.) or gram negative bacteria (e.g. MacConkey agar, Difco Inc.) or to a selective culture agar for yeasts and fungi (e.g. Plate Count Agar, Difco Inc.). Afterwards the microorganisms that have been transferred from skin to culture agar plates are cultivated at 30° C. and 37° C., aerobically and anaerobically for about 24 hours.

Colony forming units are determined by morphological and biochemical methods for a qualitative analysis and by counting for quantification. The relative composition and total cell counts are determined. The person skilled in the art can determine the genus and/or species of the microorganisms of the resident skin microbial flora which have been isolated as described above by methods known in the art. For example, the person skilled in the art may identify said microorganisms due to metabolic footprinting, fatty acid composition and composition of the cell wall etc.

The term "skin" refers to the body's outer covering, as known to the person skilled in the art. Preferably the term relates to three layers: epidermis, dermis, and subcutaneous fatty tissue. The epidermis is the outermost layer of the skin. It typically forms the waterproof, protective wrap over the body's surface and is made up of stratified squamous epithelium with an underlying basal lamina. It usually contains no blood vessels, and is nourished by diffusion from the dermis. The main type of cells which make up the epidermis are keratinocytes, with melanocytes and Langerhans cells also present. The epidermis is divided into several layers where cells are formed through mitosis at the innermost layers. They move up the strata changing shape and composition as they differentiate and become filled with keratin. They eventually reach the top layer called stratum corneum and become sloughed off, or desquamated. The outermost layer of the epidermis consists of 25 to 30 layers of dead cells. Conventionally, the epidermis is divided into 5 sublayers or strata (from superficial to deep): the stratum corneum, the stratum lucidum, the stratum granulosum, the stratum spinosum and the stratum germinativum or stratum basale. Typically, the interface between the epidermis and dermis is irregular and consists of a succession of papillae, or fingerlike projections, which are smallest where the skin is thin and longest in the skin of the palms and soles. Typically, the papillae of the palms and soles are associated with elevations of the epidermis, which produce ridges. Subcutaneous fatty tissue is the deepest layer of the skin. A characteristic of this layer is that it is composed of connective tissue, blood vessels, and fat cells. Typically, this layer binds the skin to underlying structures, insulates the body from cold, and stores energy in the form of fat. In general the skin forms a protective barrier against the action of physical, chemical, and bacterial agents on the deeper tissues. This means that tissues belonging, e.g. to the oral cavity or the vaginal region or mucous membranes do not belong to the skin. In a preferred embodiment the term "skin" relates to the outermost layer of the body's covering, i.e. the epidermis. In a more preferred embodiment the term "skin" relates to the stratum corneum of the epidermis. In an even more preferred embodiment the term skin relates to the outermost 25 to 30 layers of dead cells of the epidermis. In the most preferred embodiment the term "skin" relates to the outermost 10 layers of dead cell of the epidermis The term "stimulates" in connection with the growth of microorganisms of the resident skin microbial flora means that the growth of one or more of these microorganisms is increased when contacted with a microorganism according to the invention. An increased growth means preferably an increase in proliferation, i.e. cell divisions per time unit. Alternatively, the term "stimulates" also refers to an increase in size of individual cells. Bacterial cell size can be assessed by flow cytometry (e.g. Becton-Dickinson FACSort flow cytometer, San Jose, Calif.) after staining with the stain SYBR Green I (Molecular Probes, USA). Bacteria cell size is assessed in Side-Angle Light Scatter (SSC) mode.

An increased growth thus means an increase in biomass production per time unit.

The stimulation of growth of the microorganism(s) of the resident skin microbial flora can preferably be observed in vitro, more preferably in an assay in which a microorganism according to the invention is contacted with one or more microorganisms of the resident skin microbial flora and the growth of the(se) microorganism(s) of the resident skin microbial flora is determined. The growth can be determined by counting the numbers of cells/colonies after different time intervals of incubation and can be compared with a control which does not contain a microorganism according to the invention, thereby allowing to determine whether there is an increase in growth.

An in vitro assay for determining the stimulation of growth is described in the Examples and comprises a so-called "in vitro hole plate assay". In brief, such an assay comprises the following steps:

cultivation of at least one microorganism of the resident skin microbial flora and evenly spreading it/them on a prepared agar plate containing a suitable agar medium for growth, and preferably detection, of the respective microorganism(s);

providing holes in the inoculated agar plate;

filling the holes with precultured cells of a microorganism according to the invention;

incubating the agar plates for an appropriate amount of time and under conditions allowing growth of the microorganism(s) of the resident skin microbial flora; and determining the growth of the microorganism(s) of the resident skin microbial flora surrounding the holes containing a microorganism according to the invention and comparing it to the growth of the microorganism(s) surrounding a hole which does not contain a microorganism according to the invention.

The determination of the growth in the last step may be effected by available means and methods for determining the number of cells and/or colonies, e.g. by staining with an appropriate dye and/or optical means such as densitometry and counting the cells/colonies under the microscope.

Even more preferably, the stimulation of growth of the microorganism(s) of the resident skin microbial flora can also be observed in an in situ skin assay. Such assay is described in the Examples and, in brief, comprises the following steps:

cultivation of at least one microorganism of the resident skin microbial flora and evenly spreading it on an area of skin of a test individual;

applying an aliquot of a microorganism according to the invention in a punctual area within the area on which the microorganism(s) of the resident skin microbial flora has/have been spread;

incubating the skin for an amount of time sufficient to allow growth of the microorganism(s) of the resident skin microbial flora;

transferring the upper skin layers, including the microorganisms comprised in these, to an agar plate containing an appropriate growth medium;

incubation of the agar plates for a period of time and under conditions allowing the growth of the microorganism(s) of the resident skin microbial flora;

determining the growth of the microorganism(s) of the resident skin microbial flora surrounding the area at which the microorganism according to the invention was applied and comparing it to the growth of the microorganism(s) in a control in which no microorganism of the invention was applied.

The area of skin used for this assay may be any suitable area of skin of an individual, preferably of a human individual. In a preferred embodiment it is an area of skin on the forearm of a human individual. The size of the area is not decisive, preferably it is about 1 to 40 $cm^2$, more preferably 5 to 20 $cm^2$, even more preferably 5 to 10 $cm^2$, e.g. about 5, 6, 7, 8, 9 or 10 $cm^2$.

The microorganism(s) of the resident skin microbial flora are evenly distributed on the area, preferably in a density of approximately $10^2$ $cfu/cm^2$-$10^3$ $cfu/cm^2$. The microorganism(s) spread on the skin are air dried and an aliquot of a microorganism according to the invention is applied in a punctual manner within the area. This can be achieved by means known to the person skilled in the art. For example, the microorganisms according to the invention are centrifuged (15 min, 4000×g). The cell pellet is washed two times with K/Na-buffer (each 1 ml). Cells are resuspended in 200 µl K/Na buffer and 10 µl of prepared microorganisms are punctual applied on the pre-inoculated skin area with a micro pipet.

The incubation of the skin preferably takes place at room temperature for, e.g., two hours. The transfer of the upper skin layers, including the microorganisms comprised therein, may, e.g., be effected with the help of an adhesive tape stripe. The agar plates to which the upper skin layers have been transferred are incubated at a temperature allowing growth of the microorganism(s) or the resident skin microbial flora to be tested and contain a growth medium known to support growth of this (these) microorganism(s). The incubation typically takes place for about 24 hours. The growth of the microorganism(s) can be detected by methods known to the person skilled in the art. Preferably, it is determined by densitometry or by counting the colonies formed in the neighborhood of the point at which an aliquot of the microorganism of the invention was applied. Bacterial cell size can be assessed by flow cytometry (e.g. Becton-Dickinson FACSort flow cytometer, San Jose, Calif.) after staining with the stain SYBR Green I (Molecular Probes, USA). Bacteria cell size is assessed in Side-Angle Light Scatter (SSC) mode.

A microorganism is regarded to stimulate the growth of one or more microorganisms of the resident skin microbial flora if it leads to an increase of growth of at least one such microorganism in an in vitro hole plate assay of at least 5%, preferably of at least 10%, 20%, 30%, 40%, 50%, 60%, or 70%, more preferably of at least 75% and even more preferably of at least 80% and most preferably of at least 85% in comparison to a control to which no microorganism has been added.

More preferably, a microorganism is regarded as stimulating the growth of one or more microorganisms of the resident skin microbial flora if it leads to an increase of growth of at least one such microorganism in an in situ skin assay of at least 5%, preferably of at least 10%, 20%, 30%, 40%, 50%, 60%, or 70%, more preferably of at least 75%, even more preferably of at least 80% and most preferably of at least 85%.

In a preferred embodiment the microorganism according to the invention stimulates the growth of the major representative of the residual skin flora, i.e. *Staphylococcus epidermidis*. The meaning of the word "stimulates growth" is as described herein-above and preferably means a stimulation in vitro, more preferably in an in vitro hole plate assay as described herein-above. Even more preferably it means a stimulation in an in situ skin assay as described herein-above. Most preferably it means a stimulation in an in vitro as well as in an in situ assay. The in vitro hole plate assay and the in situ skin assay are preferably carried out as described in the Examples. In a preferred embodiment the microorganism of the present invention also stimulates the growth of *Micrococcus* spec., preferably of *Micrococcus luteus*. In a more preferred embodiment, also the growth of Diphteroids, preferably of bacteria belonging to the genus *Corynebacterium* is stimulated.

In a particularly preferred embodiment the microorganism according to the invention stimulates the growth of all microorganisms of the resident skin microbial flora.

The microorganism according to the invention is also characterized in that it does not stimulate the growth of microorganisms of the transient pathogenic micro flora. The term "transient pathogenic micro flora" refers to microorganisms which are deposited on the skin but do not multiply there or to contaminants which multiply on the skin and persist for short periods. In particular, if a microorganism is applied to the skin and is unable to grow and reproduce there under the environmental conditions provided by the healthy skin and cannot permanently colonize this organ (or a region of it), it is considered to belong to the transient pathogenic micro flora. Several bacteria, yeast and fungi can be transiently isolated from human skin but particularly the following microorganism can be classified to the transient micro flora due to their frequent appearance: *Staphylococcus aureus, Streptococcus pyogenes*, gram-negative bacilli (e.g *Acinetobacter calcoaceticus*), *Candida albicans* and *Malassezia furfur*. Microorganisms of the transient micro flora often have pathogenic factors that allow the bacterium to attach to disordered skin regions. This can e.g. be the attachment to collagen structures or keratin structures.

The microorganisms of the transient pathogenic micro flora can be determined, e.g., by metabolic footprinting, the evaluation of fatty acid composition and the composition of the cell wall, sequencing of 16S ribosomal RNA or the detection of specific DNA probes encoding specific pathogenic factors.

The term "does not stimulate the growth of microorganisms of the transient pathogenic micro flora" means that the microorganism of the invention does not stimulate the growth of at least one, preferably of more than one, preferably of more than two, more preferably of more than five and particularly preferred of any of the microorganisms of the transient pathogenic flora.

A microorganism is regarded as not stimulating the growth of a microorganism of the transient pathogenic micro flora if it does not lead to an increased growth of such a microorganism of the transient pathogenic micro flora when contacted with it. The stimulation of growth or its absence can be tested in vitro or in situ as described above in connection with the property of a microorganism of the invention to stimulate the growth of at least one microorganism of the resident skin microbial flora. Most preferably the test for determining stimulation or its absence takes place by carrying out an in vitro hole plate assay and/or an in situ skin assay as described above, more preferably as described in the Examples. A microorganism is regarded as not stimulating the growth of a microorganism of the transient pathogenic micro flora if the growth of the latter microorganism is not increased or only slightly increased when contacted with the former microorganism. "Slightly increased" means that the growth is increased not more than by 5% when compared to the control, more preferably not more than 2% when compared to the control. The term "not increased" means that there can be found no statistically relevant difference between the growth of the microorganism of the transient pathogenic micro flora contacted with a microorganism of the invention when compared to the control where no microorganism of the invention is present. The term "not increased" in a preferred embodiment also includes those cases where a microorganism actually leads to a decrease of the growth of a microorganism of the transient pathogenic micro flora, i.e. where it represses the growth of such a microorganism.

In another preferred embodiment the microorganism of the present invention does not negatively influence the growth of the microorganisms of the transient pathogenic micro flora. The term "not negatively influence" means that that there can be found no inhibition of the growth of the microorganism of the transient pathogenic micro flora contacted with a microorganism of the invention when compared to the control where no microorganism of the invention is present.

In a further preferred embodiment, the microorganism of the present invention does not stimulate the growth of the major representative of the transient pathogenic micro flora, i.e. *Staphylococcus aureus*. The test for determining whether a microorganism does or does not stimulate the growth of *Staphylococcus aureus* is preferably an in vitro and/or an in situ test as described herein-above, more preferably a test as described in the Examples.

In a particularly preferred embodiment the microorganism of the present invention is a microorganism belonging to the group of lactic acid bacteria. The term "microorganism belonging to the group of lactic acid bacteria" encompasses (a) microorganism(s) which belong(s) to bacteria, in particular belonging to gram-positive fermentative eubacteria, more particularly belonging to the family of lactobacteriaceae including lactic acid bacteria. Lactic acid bacteria are from a taxonomical point of view divided up into the subdivisions of *Streptococcus, Leuconostoc, Pediococcus* and *Lactobacillus*. The microorganism of the present invention is preferably a *Lactobacillus* species. Members of the lactic acid bacteria group normally lack porphyrins and cytochromes, do not carry out electron-transport phosphorylation and hence obtain energy only by substrate-level phosphorylation. I.e. in lactic acid bacteria ATP is synthesized through fermentation of carbohydrates. All of the lactic acid bacteria grow anaerobically, however, unlike many anaerobes, most lactic acid bacteria are not sensitive to oxygen and can thus grow in its presence as well as in its absence. Accordingly, the bacteria of the present invention are preferably aerotolerant anaerobic lactic acid bacteria, preferably belonging to the genus of *Lactobacillus*.

The lactic acid bacteria of the present invention are preferably rod-shaped or spherical, varying from long and slender to short bent rods, are moreover preferably immotile and/or asporogenous and produce lactic acid as a major or sole product of fermentative metabolism. The genus *Lacto-*

*bacillus* to which the microorganism of the present invention belongs in a preferred embodiment is divided up by the following characteristics into three major subgroups, whereby it is envisaged that the *Lactobacillus* species of the present invention can belong to each of the three major subgroups:

(a) homofermentative lactobacilli
  (i) producing lactic acid, preferably the L-, D- or DL-isomer(s) of lactic acid in an amount of at least 85% from glucose via the Embden-Meyerhof pathway;
  (ii) growing at a temperature of 45° C., but not at a temperature of 15° C.,
  (iii) being long-rod shaped; and
  (iv) having glycerol teichoic acid in the cell wall;
(b) homofermantative lactobacilli
  (i) producing lactic acid, preferably the L- or DL-isomer(s) of lactic acid via the Embden-Meyerhof pathway;
  (ii) growing at a temperature of 15° C., showing variable growth at a temperature of 45° C.;
  (iii) being short-rod shaped or coryneform; and
  (iv) having ribitol and/or glycerol teichoic acid in their cell wall;
(c) heterofermentative lactobacilli
  (i) producing lactic acid, preferably the DL-isomer of lactic acid in an amount of at least 50% from glucose via the pentose-phosphate pathway;
  (ii) producing carbondioxide and ethanol
  (iii) showing variable growth at a temperature of 15° C. or 45° C.;
  (iv) being long or short rod shaped; and
  (v) having glycerol teichoic acid in their cell wall.

Based on the above-described characteristics, the microorganisms of the present invention can be classified to belong to the group of lactic acid bacteria, particularly to the genus of *Lactobacillus*. By using classical systematics, for example, by reference to the pertinent descriptions in "Bergey's Manual of Systematic Bacteriology" (Williams & Wilkins Co., 1984), a microorganism of the present invention can be determined to belong to the genus of *Lactobacillus*. Alternatively, the microorganisms of the present invention can be classified to belong to the genus of *Lactobacillus* by methods known in the art, for example, by their metabolic fingerprint, i.e. a comparable overview of the capability of the microorganism(s) of the present invention to metabolize sugars or by other methods described, for example, in Schleifer et al., System. Appl. Microb., 18 (1995), 461-467 or Ludwig et al., System. Appl. Microb., 15 (1992), 487-501. The microorganisms of the present invention are capable of metabolizing sugar sources which are typical and known in the art for microorganisms belonging to the genus of *Lactobacillus*.

The affiliation of the microorganisms of the present invention to the genus of *Lactobacillus* can also be characterized by using other methods known in the art, for example, using SDS-PAGE gel electrophoresis of total protein of the species to be determined and comparing them to known and already characterized strains of the genus *Lactobacillus*. The techniques for preparing a total protein profile as described above, as well as the numerical analysis of such profiles, are well known to a person skilled in the art. However, the results are only reliable insofar as each stage of the process is sufficiently standardized. Faced with the requirement of accuracy when determining the attachment of a microorganism to the genus of *Lactobacillus*, standardized procedures are regularly made available to the public by their authors such as that of Pot et al., as presented during a "workshop" organized by the European Union, at the University of Ghent, in Belgium, on Sep. 12 to 16, 1994 (Fingerprinting techniques for classification and identification of bacteria, SDS-PAGE of whole cell protein). The software used in the technique for analyzing the SDS-PAGE electrophoresis gel is of crucial importance since the degree of correlation between the species depends on the parameters and algorithms used by this software. Without going into the theoretical details, quantitative comparison of bands measured by a densitometer and normalized by a computer is preferably made with the Pearson correlation coefficient. The similarity matrix thus obtained may be organized with the aid of the UPGMA (unweighted pair group method using average linkage) algorithm that not only makes it possible to group together the most similar profiles, but also to construct dendograms (see Kersters, Numerical methods in the classification and identification of bacteria by electrophoresis, in Computer-assisted Bacterial Systematics, 337-368, M. Goodfellow, A. G. O'Donnell Ed., John Wiley and Sons Ltd, 1985).

Alternatively, the affiliation of said microorganisms of the present invention to the genus of *Lactobacillus* can be characterized with regard to ribosomal RNA in a so called Riboprinter® More preferably, the affiliation of the newly identified species of the invention to the genus *Lactobacillus* is demonstrated by comparing the nucleotide sequence of the 16S ribosomal RNA of the bacteria of the invention, or of their genomic DNA which codes for the 16S ribosomal RNA, with those of other genera and species of lactic acid bacteria known to date. Another preferred alternative for determining the attachment of the newly identified species of the invention to the genus *Lactobacillus* is the use of species-specific PCR primers that target the 16S-23S rRNA spacer region. Another preferred alternative is RAPD-PCR (Nigatu et al. in Antonie van Leenwenhoek (79), 1-6, 2001) by virtue of that a strain specific DNA pattern is generated which allows to determine the affiliation of an identified microorganisms in accordance with the present invention to the genus of *Lactobacillus*. Further techniques useful for determining the affiliation of the microorganism of the present invention to the genus of *Lactobacillus* are restriction fragment length polymorphism (RFLP) (Giraffa et al., Int. J. Food Microbiol. 82 (2003), 163-172), fingerprinting of the repetitive elements (Gevers et al., FEMS Microbiol. Lett. 205 (2001) 31-36) or analysis of the fatty acid methyl ester (FAME) pattern of bacterial cells (Heyrman et al., FEMS Microbiol. Lett. 181 (1991), 55-62). Alternatively, lactobacilli can be determined by lectin typing (Annuk et al., J. Med. Microbiol. 50 (2001), 1069-1074) or by analysis of their cell wall proteins (Gatti et al., Lett. Appl. Microbiol. 25 (1997), 345-348.

In a preferred embodiment of the present application the microorganism is a probiotic *Lactobacillus* species. The term "probiotic" in the context of the present invention means that the microorganism has a beneficial effect on health if it is topically applied to the skin. Preferably, a "probiotic" microorganism is a live microorganism which, when topically applied to the skin, is beneficial for health of this tissue. Most preferably, this means that the microorganism has a positive effect on the micro flora of the skin.

In a preferred embodiment the microorganism of the present invention belongs to the species of *Lactobacillus paracasei, Lactobacillus brevis* or *Lactobacillus fermentum*. However, the *Lactobacillus* species are not limited thereto.

In a particularly preferred embodiment of the present invention the microorganism of the present invention is selected from the group consisting of *Lactobacillus paracasei, Lactobacillus brevis* or *Lactobacillus fermentum* being deposited at the DSMZ under the accession number DSM 17248 (*Lactobacillus paracasei* ssp *paracasei* LB-OB-H2), DSM 17247 (*Lactobacillus brevis* LB-OB-H1), DSM 17250 (*Lactobacillus brevis* LB-OB-H4) and DSM 17249 (*Lactobacillus fermentum* LB-OB-H3). The invention also relates to a mutant or derivative of the above-mentioned deposited *Lactobacillus* strains wherein said mutants or derivatives have retained their capability to stimulate the growth of at least one microorganism of the resident skin microbial flora and their property not to stimulate the growth of microorganisms of the transient pathogenic micro flora.

The term "*Lactobacillus paracasei, Lactobacillus brevis* or *Lactobacillus fermentum* being deposited at the DSMZ under the accession number" relates to cells of a microorganism belonging to the species *Lactobacillus paracasei, Lactobacillus brevis* or *Lactobacillus fermentum* deposited at the Deutsche Sammlung für Mikroorganismen and Zellkulturen (DSMZ) on Apr. 18, 2005 and having the following deposit numbers: DSM 17248 (*Lactobacillus paracasei* ssp *paracasei* LB-OB-H02), DSM 17247 (*Lactobacillus brevis* LB-OB-H01, DSM 17250 (*Lactobacillus brevis* LB-OB-H04) and DSM 17249 (*Lactobacillus fermentum* LB-OB-H03). The DSMZ is located at the Mascheroder Weg 1 b, D-38124 Braunschweig, Germany. The aforementioned deposits were made pursuant to the terms of the Budapest treaty on the international recognition of the deposit of microorganisms for the purposes of patent procedures.

In a particular preferred embodiment the microorganisms of the present invention are "isolated" or "purified". The term "isolated" means that the material is removed from its original environment, e.g. the natural environment if it is naturally occurring, or the culture medium if it is cultured. For example, a naturally-occurring microorganism, preferably a *Lactobacillus* species, separated from some or all of the coexisting materials in the natural system, is isolated. Such a microorganism could be part of a composition, and is to be regarded as still being isolated in that the composition is not part of its natural environment.

The term "purified" does not require absolute purity; rather, it is intended as a relative definition. Individual microorganisms obtained from a library have been conventionally purified to microbiological homogeneity, i.e. they grow as single colonies when streaked out on agar plates by methods known in the art. Preferably, the agar plates that are used for this purpose are selective for *Lactobacillus* species. Such selective agar plates are known in the art.

In another aspect the present invention relates to an inactivated form of the microorganism of the present invention, which is, e.g., thermally inactivated or lyophilized, but which retains the property of stimulating the growth of microorganisms of the resident skin microbial flora and of not stimulating the growth of microorganisms of the transient pathogenic micro flora.

According to the present invention the term "inactivated form of the microorganism of the present invention" includes a dead or inactivated cell of the microorganism of the present invention, preferably of the *Lactobacillus* species disclosed herein, which is no longer capable to form a single colony on a plate specific for microorganisms belonging to the genus of *Lactobacillus*. Said dead or inactivated cell may have either an intact or broken cell membrane. Methods for killing or inactivating cells of the microorganism of the present invention are known in the art. El-Nezami et al., J. Food Prot. 61 (1998), 466-468 describes a method for inactivating *Lactobacillus* species by UV-irradiation. Preferably, the cells of the microorganism of the present invention are thermally inactivated or lyophilised. Lyophilisation of the cells of the present invention has the advantage that they can be easily stored and handled while retaining their property to stimulate growth of microorganisms of the resident skin microbial flora while not stimulating the growth of microorganisms of the transient pathogenic micro flora. Moreover, lyophilised cells can be grown again when applied under conditions known in the art to appropriate liquid or solid media. Lyophilization is done by methods known in the art. Preferably, it is carried out for at least 2 hours at room temperature, i.e. any temperature between 16° C. and 25° C. Moreover, the lyophilized cells of the microorganism of the present invention are stable for at least 4 weeks at a temperature of 4° C. so as to still retain their properties as described above. Thermal inactivation can be achieved by incubating the cells of the microorganism of the present invention for at least 2 hours at a temperature of 170° C. Yet, thermal inactivation is preferably achieved by autoclaving said cells at a temperature of 121° C. for at least 20 minutes in the presence of satured steam at an atmospheric pressure of 2 bar. In the alternative, thermal inactivation of the cells of the microorganism of the present invention is achieved by freezing said cells for at least 4 weeks, 3 weeks, 2 weeks, 1 week, 12 hours, 6 hours, 2 hours or 1 hour at −20° C. It is preferred that at least 70%, 75% or 80%, more preferably 85%, 90% or 95% and particularly preferred at least 97%, 98%, 99% and more particularly preferred, 99.1%, 99.2%, 99.3%, 99.4%, 99.5%, 99.6%, 99.7%, 99.8% or 99.9% and most particularly preferred 100% of the cells of the inactivated form of the microorganism of the present invention are dead or inactivated, however, they have still the capability to stimulate growth of microorganisms of the resident skin microbial flora but do not stimulate growth of microorganisms of the transient pathogenic micro flora. Whether the inactivated form of the microorganism of the present invention is indeed dead or inactivated can be tested by methods known in the art, for example, by a test for viability.

The term "inactivated form of the microorganism of the present invention" also encompasses lysates or fractions of the microorganism of the present invention, preferably of the *Lactobacillus* species disclosed herein, wherein said lysates or fractions preferably stimulate the growth of a microorganism of the resident skin microbial flora and does not stimulate the growth of microorganisms of the transient pathogenic micro flora, in particular, *Staphylococcus aureus* as described herein. This stimulation can be tested as described herein and in particular as described in the appended Examples. In case, a lysate or fraction of the microorganism of the present invention may stimulate the growth of a microorganism of the transient pathogenic micro flora, then the skilled person can, for example, further purify said lysate or fraction by methods known in the art, which are exemplified herein below, so as to remove substances which may stimulate the growth of microorganisms of the transient pathogenic micro flora. Afterwards the person skilled in the art can again test said lysate or fraction whether it stimulates the growth of a microorganism of the resident skin microbial flora but not the growth of a microorganism of the transient pathogenic micro flora.

According to the present invention the term "lysate" means a solution or suspension in an aqueous medium of cells of the microorganism of the present invention that are broken or an extract. However, the term should not be construed in any limiting way. The cell lysate comprises, e.g., macromolecules, like DNA, RNA, proteins, peptides, carbohydrates, lipids and the like and/or micromolecules, like amino acids, sugars, lipid acids and the like, or fractions of it. Additionally, said lysate comprises cell debris which may be of smooth or granular structure. Methods for preparing cell lysates of microorganism are known in the art, for example, by employing French press, cells mill using glass or iron beads or enzymatic cell lysis and the like. In addition, lysing cells relates to various methods known in the art for opening/destroying cells. The method for lysing a cell is not important and any method that can achieve lysis of the cells of the microorganism of the present invention may be employed. An appropriate one can be chosen by the person skilled in the art, e.g. opening/destruction of cells can be done enzymatically, chemically or physically. Non-limiting examples for enzymes and enzyme cocktails are proteases, like proteinase K, lipases or glycosidases; non-limiting examples for chemicals are ionophores, detergents, like sodium dodecyl sulfate, acids or bases; and non-limiting examples of physical means are high pressure, like French-pressing, osmolarity, temperature, like heat or cold. Additionally, a method employing an appropriate combination of an enzyme other than the proteolytic enzyme, an acid, a base and the like may also be utilized. For example, the cells of the microorganism of the present invention are lysed by freezing and thawing, more preferably freezing at temperatures below −70° C. and thawing at temperatures of more than 30° C., particularly freezing is preferred at temperatures below −75° C. and thawing is preferred at temperatures of more than 35° C. and most preferred are temperatures for freezing below −80° C. and temperatures for thawing of more than 37° C. It is also preferred that said freezing/thawing is repeated for at least 1 time, more preferably for at least 2 times, even more preferred for at least 3 times, particularly preferred for at least 4 times and most preferred for at least 5 times.

Accordingly, those skilled in the art can prepare the desired lysates by referring to the above general explanations, and appropriately modifying or altering those methods, if necessary. Preferably, the aqueous medium used for the lysates as described is water, physiological saline, or a buffer solution. An advantage of a bacterial cell lysate is that it can be easily produced and stored cost efficiently since less technical facilities are needed.

According to the invention, lysates are also preparations of fractions of molecules from the above-mentioned lysates. These fractions can be obtained by methods known to those skilled in the art, e.g., chromatography, including, e.g., affinity chromatography, ion-exchange chromatography, size-exclusion chromatography, reversed phase-chromatography, and chromatography with other chromatographic material in column or batch methods, other fractionation methods, e.g., filtration methods, e.g., ultrafiltration, dialysis, dialysis and concentration with size-exclusion in centrifugation, centrifugation in density-gradients or step matrices, precipitation, e.g., affinity precipitations, salting-in or salting-out (ammoniumsulfate-precipitation), alcoholic precipitations or other proteinchemical, molecular biological, biochemical, immunological, chemical or physical methods to separate above components of the lysates. In a preferred embodiment those fractions which are more immunogenic than others are preferred. Those skilled in the art are able to choose a suitable method and determine its immunogenic potential by referring to the above general explanations and specific explanations in the examples herein, and appropriately modifying or altering those methods, if necessary.

Accordingly, the term "an inactive form of the microorganism of the present invention" also encompasses filtrates of the microorganism of the present invention, preferably of the *Lactobacillus* species disclosed herein, wherein said filtrates preferably inhibit the growth of one or more microorganisms of the transient pathogenic skin micro flora, preferably of *Staphylococcus aureus* and do not inhibit the growth of microorganisms of the healthy normal resident skin micro flora. This inhibition can be tested as described herein and in particular as described in the appended Examples. In case, a filtrate of the microorganism of the present invention may not inhibit or stimulate the growth of a microorganism of the transient pathogenic skin micro flora, then the skilled person can, for example, further purify said filtrate by methods known in the art, so as to remove substances which may stimulate the growth of microorganisms of the transient pathogenic skin micro flora. Afterwards the person skilled in the art can again test said filtrate whether it inhibits the growth of a microorganism of the transient pathogenic skin micro flora but not the growth of a microorganism of the resident skin micro flora.

The term "filtrate" means a cell-free solution or suspension of the microorganism of the present invention which has been obtained as supernatant of a centrifugation procedure of a culture of the microorganism of the present invention in any appropriate liquid, medium or buffer known to the person skilled in the art. However, the term should not be construed in any limiting way. The filtrate comprises, e.g., macromolecules, like DNA, RNA, proteins, peptides, carbohydrates, lipids and the like and/or micromolecules, like amino acids, sugars, lipid acids and the like, or fractions of it. Methods for preparing filtrates of microorganism are known in the art. In addition, "filtrate" relates to various methods known in the art. The exact method is not important and any method that can achieve filtration of the cells of the microorganism of the present invention may be employed.

The term "an inactive form of the microorganism of the present invention" encompasses any part of the cells of the microorganism of the present invention. Preferably, said inactive form is a membrane fraction obtained by a membrane-preparation. Membrane preparations of microorganisms belonging to the genus of *Lactobacillus* can be obtained by methods known in the art, for example, by employing the method described in Rollan et al., Int. J. Food Microbiol. 70 (2001), 303-307, Matsuguchi et al., Clin. Diagn. Lab. Immunol. 10 (2003), 259-266 or Stentz et al., Appl. Environ. Microbiol. 66 (2000), 4272-4278 or Varmanen et al., J. Bacteriology 182 (2000), 146-154. Alternatively, a whole cell preparation is also envisaged.

In another aspect the present invention relates to a composition comprising a microorganism according to the present invention or a mutant, derivative or inactive form of this microorganism as described above. In a preferred embodiment, said composition comprises a microorganism as described above in an amount between $10^2$ to $10^{12}$ cells, preferably $10^3$ to $10^8$ cells per mg in a solid form of the composition. In case of a liquid form of compositions, the amount of the microorganisms is between $10^2$ to $10^{13}$ cells per ml. In a further preferred embodiment said compositions are in the form of emulsions, e.g. oil in water or water in oil emulsions, in the form of ointments or in the form of micro-capsules. In case of emulsions, ointments or micro-capsules the compositions comprise a microorganism as described herein in an amount between $10^2$ to $10^{13}$ cells per ml. However, for specific compositions the amount of the microorganism may be different as is described herein.

In a still further aspect, the present invention provides a method for the production of a composition for protecting the skin against pathogenic microorganisms comprising the steps of formulating a microorganism according to the invention or a mutant, derivative or inactive form of this microorganism as described above with a cosmetically or pharmaceutical acceptable carrier or excipient.

The term "composition", as used in accordance with the present invention, relates to (a) composition(s) which comprise(s) at least one microorganism of the present invention or mutant, derivative or inactive form of said microorganism as described above. It is envisaged that the compositions of the present invention which are described herein below comprise the aforementioned ingredients in any combination. It may, optionally, comprise at least one further ingredient suitable for protecting the skin against pathogenic microorganisms. Accordingly, it may optionally comprise any combination of the hereinafter described further ingredients. The term "ingredients suitable for protecting the skin against pathogenic microorganisms" encompasses compounds or compositions and/or combinations thereof which lower the pH.

The composition may be in solid, liquid or gaseous form and may be, inter alia, in the form of (a) powder(s), (a) solution(s) (an) aerosol(s), suspensions, emulsions, liquids, elixirs, extracts, tincture or fluid extracts or in a form which is particularly suitable for topical administration. Forms suitable for topical application include, e.g., a paste, an ointment, a lotion, a cream, a gel or a transdermal patch.

Preferably, the composition of the present invention is a cosmetic composition further comprising a cosmetically acceptable carrier or excipient. More preferably, said cosmetic composition is a paste, an ointment, a lotion, a cream or a gel.

The cosmetic composition of the present invention comprises the microorganism of the present invention, mutant, derivative or inactive form thereof as described above in connection with the composition of the invention and further a cosmetically acceptable carrier. Preferably the cosmetic composition of the present invention is for use in topical applications.

The term "cosmetically acceptable carrier" as used herein means a suitable vehicle, which can be used to apply the present compositions to the skin in a safe and effective manner. Such vehicle may include materials such as emulsions, e.g. oil in water or water in oil emulsions, ointments or micro capsules. It is also advantageous to administer the active ingredients in encapsulated form, e.g. as cellulose encapsulation, in gelatine, with polyamides, niosomes, wax matrices, with cyclodextrins or liposomally encapsulated. The term "safe and effective amount" as used herein, means a sufficient amount to stimulate growth of at least one microorganism of the resident skin microbial flora.

In another aspect the present invention relates to a pharmaceutical composition comprising the microorganism of the present invention or a derivative or mutant or an inactive form thereof as described above further comprising a pharmaceutical acceptable carrier or excipient. The pharmaceutical composition preferably is in a form which is suitable for topical administration.

In addition, the present invention relates to the use of a microorganism of the present invention or of a derivative or mutant or an inactive form thereof as described above for the preparation of a composition, preferably a pharmaceutical or cosmetic composition.

Pharmaceutical compositions comprise a therapeutically effective amount of a microorganism of the present invention or of a derivative or mutant of the present invention or an inactive form of said microorganism of the present invention as described above and can be formulated in various forms, e.g. in solid, liquid, powder, aqueous, lyophilized form.

The pharmaceutical composition may be administered with a pharmaceutically acceptable carrier to a patient, as described herein. In a specific embodiment, the term "pharmaceutically acceptable" means approved by a regulatory agency or other generally recognized pharmacopoeia for use in animals, and more particularly in humans.

The term "carrier" refers to a diluent, adjuvant, excipient, or vehicle with which the therapeutic is administered. Such a carrier is pharmaceutically acceptable, i.e. is non-toxic to a recipient at the dosage and concentration employed. It is preferably isotonic, hypotonic or weakly hypertonic and has a relatively low ionic strength, such as provided by a sucrose solution. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers. Suitable pharmaceutical excipients include starch, glucose, sucrose, gelatin, malt, rice, flour, chalk, silica gel, sodium stearate, glycerol monostearate, talc, sodium ion, dried skim milk, glycerol, propylene, glycol, water, ethanol and the like. The composition, if desired, can also contain minor amounts of wetting or emulsifying agents, or pH buffering agents. These compositions can take the form of, e.g., solutions, suspensions, emulsion, powders, sustained-release formulations and the like. Examples of suitable pharmaceutical carriers are described in "Remington's Pharmaceutical Sciences" by E. W. Martin. Some other examples of substances which can serve as pharmaceutical carriers are sugars, such as glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; calcium carbonate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; cranberry extracts and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tabletting agents, stabilizers, anti-oxidants and preservatives, can also be present. It is also advantageous to administer the active ingredients in encapsulated form, e.g. as cellulose encapsulation, in gelatine, with polyamides, niosomes, wax matrices, with cyclodextrins or liposomally encapsulated.

Generally, the ingredients are supplied either separately or mixed together in unit dosage form, for example, as a dry lyophilised powder or water free concentrate in a hermetically sealed container such as an ampoule or sachette indicating the quantity of active agent.

The pharmaceutical composition of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In vitro or in situ assays, e.g. those described in the Examples, may optionally be employed to help identify optimal dosage ranges. The precise dose to be employed in the formulation will also depend on the route of administration, and the seriousness of the disease or disorder, and should be decided according to the judgment of the practitioner and each patient's circumstances. The topical route of administration is preferred. Effective doses may be extrapolated from dose-response curves derived from in vitro or (animal) model test systems. Preferably, the pharmaceutical composition is administered directly or in combination with an adjuvant. Adjuvants may be selected from the group consisting of a chloroquine, protic polar compounds, such as propylene glycol, polyethylene glycol, glycerol, EtOH, 1-methyl L-2-pyrrolidone or their derivatives, or aprotic polar compounds such as dimethylsulfoxide (DMSO), diethylsulfoxide, di-n-propylsulfoxide, dimethylsulfone, sulfolane, dimethylformamide, dimethylacetamide, tetramethylurea, acetonitrile or their derivatives. These compounds are added in conditions respecting pH limitations. The composition of the present invention can be administered to a vertebrate. "Vertebrate" as used herein is intended to have the same meaning as commonly understood by one of ordinary skill in the art. Particularly, "vertebrate" encompasses mammals, and more particularly humans.

The term "administered" means administration of a therapeutically effective dose of the aforementioned composition. By "therapeutically effective amount" is meant a dose that produces the effects for which it is administered, preferably this effect is the protection of skin against pathogenic microorganisms. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

The methods are applicable to both human therapy and veterinary applications. The compounds described herein having the desired therapeutic activity may be administered in a physiologically acceptable carrier to a patient, as described herein. Depending upon the manner of administration, the compounds may be formulated in a variety of ways as discussed below. The concentration of the therapeutically active compound in the formulation may vary from about 0.01-100 wt %. The agent may be administered alone or in combination with other treatments.

The administration of the pharmaceutical composition can be done in a variety of ways. The preferable route of administering is the topical route.

The attending physician and clinical factors will determine the dosage regimen. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg; however, doses below or above this exemplary range are envisioned, especially considering the aforementioned factors.

The dosages are preferably given once a week, more preferably 2 times, 3 times, 4 times, 5 times or 6 times a week and most preferably daily and even more preferably, 2 times a day or more often. In particular, it may be preferable to give a dosage each time after a disturbance of the resident skin flora occurred, e.g. by washing. However, during progression of the treatment the dosages can be given in much longer time intervals and in need can be given in much shorter time intervals, e.g., several times a day. In a preferred case the immune response is monitored using herein described methods and further methods known to those skilled in the art and dosages are optimized, e.g., in time, amount and/or composition. Progress can be monitored by periodic assessment. It is also envisaged that the pharmaceutical compositions are employed in co-therapy approaches, i.e. in co-administration with other medicaments or drugs, for example other drugs for protecting skin against pathogenic microorganisms.

Topical administration of the cosmetic or pharmaceutical composition of the present invention is useful when the desired treatment involves areas or organs readily accessible by topical administration. For application topically to the skin, the pharmaceutical composition is preferably formulated with a suitable paste, ointment, lotion, cream, gel or transdermal patches. The cosmetic or pharmaceutical preparations can, depending on the field of use, also be in the form of a spray (pump spray or aerosol), foam, gel spray, mousse, suspensions or powders.

A suitable paste comprises the active ingredient suspended in a carrier. Such carriers include, but are not limited to, petroleum, soft white paraffin, yellow petroleum jelly and glycerol.

The cosmetic or pharmaceutical composition may also be formulated with a suitable ointment comprising the active components suspended or dissolved in a carrier. Such carriers include, but are not limited to, one or more of glycerol, mineral oil, liquid oil, liquid petroleum, white petroleum, yellow petroleum jelly, propylene glycol, alcohols, triglycerides, fatty acid esters such as cetyl ester, polyoxyethylene polyoxypropylene compound, waxes such as white wax and yellow beeswax, fatty acid alcohols such as cetyl alcohol, stearyl alcohol and cetylstearylalcohol, fatty acids such as stearic acid, cetyl stearate, lanolin, magnesium hydroxide, kaolin and water.

Alternatively, the cosmetic or pharmaceutical composition may also be formulated with a suitable lotion or cream comprising the active components suspended or dissolved in a carrier. Such carriers include, but are not limited to, one or more of mineral oil such as paraffin, vegetable oils such as castor oil, castor seed oil and hydrogenated castor oil, sorbitan monostearat, polysorbat, fatty acid esters such as cetyl ester, wax, fatty acid alcohols such as cetyl alcohol, stearyl alcohol, 2-octyldodecanol, benzyl alcohol, alcohols, triglycerides and water.

Alternatively, the cosmetic or pharmaceutical composition may also be formulated with a suitable gel comprising the active components suspended or dissolved in a carrier. Such carriers include, but are not limited to, one or more of water, glycerol, propyleneglycole, liquid paraffin, polyethylene, fatty oils, cellulose derivatives, bentonite and colloidal silicon dioxide.

Suitable propellants for aerosols according to the invention are the customary propellants, for example propane, butane, pentane and others.

The preparations according to the invention may generally comprise further auxiliaries as are customarily used in such preparations, e.g. preservatives, perfumes, antifoams, dyes, pigments, thickeners, surface-active substances, emulsifiers, emollients, finishing agents, fats, oils, waxes or other customary constituents, of a cosmetic or dermatological formulation, such as alcohols, polyols, polymers, foam stabilizers, solubility promoters, electrolytes, organic acids, organic solvents, or silicone derivatives.

The cosmetic or pharmaceutical composition according to the invention may comprise emollients. Emollients may be used in amounts which are effective to prevent or relieve dryness. Useful emollients include, without limitation: hydrocarbon oils and waxes; silicone oils; triglyceride esters; acetoglyceride esters; ethoxylated glyceride; alkyl esters; alkenyl esters; fatty acids; fatty alcohols; fatty alcohol ethers; etheresters; lanolin and derivatives; polyhydric alcohols (polyols) and polyether derivatives; polyhydric alcohol (polyol) esters; wax esters; beeswax derivatives; vegetable waxes; phospholipids; sterols; and amides.

Thus, for example, typical emollients include mineral oil, especially mineral oils having a viscosity in the range of 50 to 500 SUS, lanolin oil, mink oil, coconut oil, cocoa butter, olive oil, almond oil, macadamia nut oil, aloa extract, jojoba oil, safflower oil, corn oil, liquid lanolin, cottonseed oil, peanut oil, purcellin oil, perhydrosqualene (squalene), caster oil, polybutene, odorless mineral spirits, sweet almond oil, avocado oil, calophyllum oil, ricin oil, vitamin E acetate, olive oil, mineral spirits, cetearyl alcohol (mixture of fatty alcohols consisting predominantly of cetyl and stearyl alcohols), linolenic alcohol, oleyl alcohol, octyl dodecanol, the oil of cereal germs such as the oil of wheat germ cetearyl octanoate (ester of cetearyl alcohol and 2-ethylhexanoic acid), cetyl palmitate, diisopropyl adipate, isopropyl palmitate, octyl palmitate, isopropyl myristate, butyl myristate, glyceryl stearate, hexadecyl stearate, isocetyl stearate, octyl stearate, octylhydroxy stearate, propylene glycol stearate, butyl stearate, decyl oleate, glyceryl oleate, acetyl glycerides, the octanoates and benzoates of (C12-C15) alcohols, the octanoates and decanoates of alcohols and polyalcohols such as those of glycol and glycerol, and ricin-oleates of alcohols and poly alcohols such as those of isopropyl adipate, hexyl laurate, octyl dodecanoate, dimethicone copolyol, dimethiconol, lanolin, lanolin alcohol, lanolin wax, hydrogenated lanolin, hydroxylated lanolin, acetylated lanolin, petrolatum, isopropyl lanolate, cetyl myristate, glyceryl myristate, myristyl myristate, myristyl lactate, cetyl alcohol, isostearyl alcohol stearyl alcohol, and isocetyl lanolate, and the like.

Moreover, the cosmetic or pharmaceutical composition according to the invention may also comprise emulsifiers. Emulsifiers (i.e., emulsifying agents) are preferably used in amounts effective to provide uniform blending of ingredients of the composition. Useful emulsifiers include (i) anionics such as fatty acid soaps, e.g., potassium stearate, sodium stearate, ammonium stearate, and triethanolamine stearate; polyol fatty acid monoesters containing fatty acid soaps, e.g., glycerol monostearate containing either potassium or sodium salt; sulfuric esters (sodium salts), e.g., sodium lauryl 5 sulfate, and sodium cetyl sulfate; and polyol fatty acid monoesters containing sulfuric esters, e.g., glyceryl monostearate containing sodium lauryl sulfate; (ii) cationics chloride such as N(stearoyl colamino formylmethyl) pyridium; N-soya-N-ethyl morpholinium ethosulfate; alkyl dimethyl benzyl ammonium chloride; diisobutylphenoxytheoxyethyl dimethyl benzyl ammonium chloride; and cetyl pyridium chloride; and (iii) nonionics such as polyoxyethylene fatty alcohol ethers, e.g., monostearate; polyoxyethylene lauryl alcohol; polyoxypropylene fatty alcohol ethers, e.g., propoxylated oleyl alcohol; polyoxyethylene fatty acid esters, e.g., polyoxyethylene stearate; polyoxyethylene sorbitan fatty acid esters, e.g., polyoxyethylene sorbitan monostearate; sorbitan fatty acid esters, e.g., sorbitan; polyoxyethylene glycol fatty acid esters, e.g., polyoxyethylene glycol monostearate, and polyol fatty acid esters, e.g., glyceryl monostearate and propylene glycol monostearate; and ethoxylated lanolin derivatives, e.g., ethoxylated lanolins, ethoxylated lanolin alcohols and ethoxylated cholesterol. The selection of emulsifiers is exemplarly described in Schrader, Grundlagen and Rezepturen der Kosmetika, Huthig Buch Verlag, Heidelberg, $2^{nd}$ edition, 1989, $3^{rd}$ part.

The cosmetic or pharmaceutical composition according to the invention may also include a surfactant. Suitable surfactants may include, for example, those surfactants generally grouped as cleansing agents, emulsifying agents, foam boosters, hydrotropes, solubilizing agents, suspending agents and nonsurfactants (facilitates the dispersion of solids in liquids).

The surfactants are usually classified as amphoteric, anionic, cationic and nonionic surfactants. Amphoteric surfactants include acylamino acids and derivatives and N-alkylamino acids. Anionic surfactants include: acylamino acids and salts, such as, acylglutamates, acylpeptides, acylsarcosinates, and acyltaurates, carboxylic acids and salts, such as, alkanoic acids, ester carboxylic acids, and ether carboxylic acids; sulfonic acids and salts, such as, acyl isethionates, alkylaryl sulfonates, alkyl sulfonates, and sulfosuccinates; sulfuric acid esters, such as, alkyl ether sulfates and alkyl sulfates. Cationic surfactants include: alkylamines, alkyl imidazolines, ethoxylated amines, and quaternaries (such as, alkylbenzyldimethylammonium salts, alkyl betaines, heterocyclic ammonium salts, and tetra alkylammonium salts). And nonionic surfactants include: alcohols, such as primary alcohols containing 8 to 18 carbon atoms; alkanolamides such as alkanolamine derived amides and ethoxylated amides; amine oxides; esters such as ethoxylated carboxylic acids, ethoxylated glycerides, glycol esters and derivatives, monoglycerides, polyglyceryl esters, polyhydric alcohol esters and ethers, sorbitan/sorbitol esters, and triesters of phosphoric acid; and ethers such as ethoxylated alcohols, ethoxylated lanolin, ethoxylated polysiloxanes, and propoxylated polyoxyethylene ethers.

Furthermore, a cosmetic or pharmaceutical composition according to the invention may also comprise a film former. Suitable film formers which are used in accord with the invention keep the composition smooth and even and include, without limitation: acrylamide/sodium acrylate copolymer; ammonium acrylates copolymer; Balsam Peru; cellulose gum; ethylene/maleic anhydride copolymer; hydroxyethylcellulose; hydroxypropylcellulose; polyacrylamide; polyethylene; polyvinyl alcohol; pvm/MA copolymer (polyvinyl methylether/maleic anhydride); PVP (polyvinylpyrrolidone); maleic anhydride copolymer such as PA-18 available from Gulf Science and Technology; PVP/hexadecene copolymer such as Ganex V-216 available from GAF Corporation; acryliclacrylate copolymer; and the like.

Generally, film formers can be used in amounts of about 0.1% to about 10% by weight of the total composition with about 1% to about 8% being preferred and about 0.1 DEG/O to about 5% being most preferred. Humectants can also be used in effective amounts, including: fructose; glucose; glulamic acid; glycerin; honey; maltitol; methyl gluceth-10, methyl gluceth-20; propylene glycol; sodium lactate; sucrose; and the like.

Of course, the cosmetic or pharmaceutical composition of the present invention can also comprise a preservative. Preservatives according to certain compositions of the invention include, without limitation: butylparaben; ethylparaben; imidazolidinyl urea; methylparaben; O-phenylphenol; propylparaben; quaternium-14; quaternium-15; sodium dehydroacetate; zinc pyrithione; and the like.

The preservatives are used in amounts effective to prevent or retard microbial growth. Generally, the preservatives are used in amounts of about 0.1% to about 1% by weight of the total composition with about 0.1% to about 0.8% being preferred and about 0.1% to about 0.5% being most preferred.

A cosmetic or pharmaceutical composition according to the invention may also comprise a perfume. Perfumes (fragrance components) and colorants (coloring agents) well known to those skilled in the art may be used in effective amounts to impart the desired fragrance and color to the compositions of the invention.

Furthermore, a cosmetic or pharmaceutical composition of the present invention may also comprise a wax. Suitable waxes which are useful in accord with the invention include: animal waxes, such as beeswax, spermaceti, or wool wax (lanolin); plant waxes, such as carnauba or candelilla; mineral waxes, such as montan wax or ozokerite; and petroleum waxes, such as paraffin wax and microcrystalline wax (a high molecular weight petroleum wax). Animal, plant, and some mineral waxes are primarily esters of a high molecular weight fatty alcohol with a high molecular weight fatty acid. For example, the hexadecanoic acid ester of tricontanol is commonly reported to be a major component of beeswax. Other suitable waxes according to the invention include the synthetic waxes including polyethylene polyoxyethylene and hydrocarbon waxes derived from carbon monoxide and hydrogen.

Representative waxes also include: cerosin; cetyl esters; hydrogenated joioba oil; hydrogenated jojoba wax; hydrogenated rice bran wax; Japan wax; jojoba butter; jojoba oil; jojoba wax; munk wax; montan acid wax; ouricury wax; rice bran wax; shellac wax; sufurized jojoba oil; synthetic beeswax; synthetic jojoba oils; trihydroxystearin; cetyl alcohol; stearyl alcohol; cocoa butter; fatty acids of lanolin; mono-, di- and 25 triglycerides which are solid at 25 DEG C., e.g., glyceyl tribehenate (a triester of behenic acid and glycerine) and C1g-C36 acid triglyceride (a mixture of triesters of C1g-C36 carboxylic acids and glycerine) available from Croda, Inc., New York, N.Y. under the tradenames Syncrowax HRC and Syncrowax HGL-C, respectively; fatty esters which are solid at 25 DEG C.; silicone waxes such as methyloctadecaneoxypolysiloxane and poly (dimethylsiloxy) stearoxysiloxane; stearyl mono- and diethanolamide; rosin and its derivatives such as the abietates of glycol and glycerol; hydrogenated oils solid at 25 DEG C.; and sucroglycerides. Thickeners (viscosity control agents) which may be used in effective amounts in aqueous systems include: algin; carbomers such as carbomer 934, 934P, 940 and 941; cellulose gum; cetearyl alcohol, cocamide DEA, dextrin; gelatin; hydroxyethylcellulose; hydroxypropylcellulose; hydroxypropyl methylcellulose; magnesium aluminum silicate; myristyl alcohol; oat flour; oleamide DEA; oleyl alcohol; PEG-7M; PEG-14M; PEG-90M; stearamide DEA; stearamide MEA; stearyl alcohol; tragacanth gum; wheat starch; xanthan gum; and the likein the above list of thickeners, DEA is diethanolamine, and MEA is monoethanolamine. Thickeners (viscosity control agents) which may be used in effective amounts in nonaqueous systems include aluminum stearates; beeswax; candelilla wax; carnauba; ceresin; cetearyl alcohol; cetyl alcohol; cholesterol; hydrated silica; hydrogenated castor oil; hydrogenated cottonseed oil; hydrogenated soybean oil; hydrogenated tallow glyceride; hydrogenated vegetable oil; hydroxypropyl cellulose; lanolin alcohol; myristyl alcohol; octytdodecyl stearoyl sulfate; oleyl alcohol; ozokerite; microcystalline wax; paraffin, pentaerythrityl tetraoctanoate; polyacrylamide; polybutene; polyethylene; propylene glycol dicaprylate; propylene glycol dipelargonate; stearalkonium hectorite; stearyl alcohol; stearyl stearate; synthetic beeswax; trihydroxystearin; trilinolein; tristearin; zinc stearate; and the like.

Customary native and synthetic thickeners or gel formers in formulations are crosslinked polyacrylic acids and derivatives thereof, polysaccharides, such as xanthane gum or alginates, carboxymethylcellulose or hydroxycarboxymethylcellulose, hydrocolloids such as gum Arabic or montmorillonite minerals, such as bentonites or fatty alcohols, polyvinyl alcohol and polyvinlypyrrolidone.

Other ingredients which can be added or used in a cosmetic or pharmaceutical composition according to the invention in amounts effective for their intended use, include: biological additives to enhance performance or consumer appeal such as amino acids, proteins, vanilla, aloe extract, bioflavinoids, and the like; buffering agents, chelating agents such as EDTA; emulsion stabilizers; pH adjusters; opacifying agents; and propellants such as butane carbon clioxide, ethane, hydrochlorofluorocarbons 22 and 142b, hydrofluorocarbon 152a, isobutane, isopentane, nitrogen, nitrous oxide, pentane, propane, and the like.

Furthermore, the preparations according to the invention may also comprise compounds which have an antioxidative, free-radical scavenger, skin moisturizing or moisture-retaining, antierythematous, antiinflammatory or antiallergic action, in order to supplement or enhance their action. In particular, these compounds can be chosen from the group of vitamins, plant extracts, alpha- and beta-hydroxy acids, ceramides, antiinflammatory, antimicrobial or UV-filtering substances, and derivatives thereof and mixtures thereof. Advantageously, preparations according to the invention can also comprise substances which absorb UV radiation in the UV-B and/or UV-A region. The lipid phase is advantageously chosen from the group of substances of mineral oils, mineral waxes, branched and/or unbranched hydrocarbons and hydrocarbon waxes, triglycerides of saturated and/or unsaturated, branched and/or unbranched $C_8$-$C_{24}$-alkanecarboxylic acids; they can be chosen from synthetic, semisynthetic or natural oils, such as olive oil, palm oil, almond oil or mixtures; oils, fats or waxes, esters of saturated and/or unsaturated, branched and/or unbranched $C_3$-$C_{30}$-alkane carboxylic acids and saturated and/or unsaturated, branched and/or unbranched $C_3$-$C_{30}$-alcohols, from aromatic carboxylic acids and saturated and/or unsaturated, branched and/or unbranched $C_3$-$C_{30}$-alcohols, for example isopropyl myristate, isopropyl stearate, hexyldecyl stearate, oleyl oleate; and also synthetic, semisynthetic and natural mixtures of such esters, such as jojoba oil, alkyl benzoates or silicone oils, such as, for example, cyclomethicone, dimethylpolysiloxane, diethylpolysiloxane, octamethylcyclo-tetrasiloxane and mixtures thereof or dialkyl ethers.

The active ingredients according to the invention may, for example, be used in cosmetic compositions for the cleansing of the skin, such as bar soaps, toilet soaps, curd soaps, transparent soaps, luxury soaps, deodorizing soaps, cream soaps, baby soaps, skin protection soaps, abrasive soaps, syndets, liquid soaps, pasty soaps, soft soaps, washing pastes, liquid washing, showering and bath preparations, e.g. washing lotions, shower preparations, shower gels, foam baths, cream foam baths, oil baths, bath extracts, scrub preparations, in-situ products, shaving foams, shaving lotions, shaving creams. In addition, they are suitable for skin cosmetic preparations, such as W/O or O/W skin and body creams, day and night creams, light protection compositions, aftersun products, hand care products, face creams, multiple emulsions, gelees, microemulsions, liposome preparations, niosome preparations, antiwrinkle creams, face oils, lipogels, sportgels, moisturizing creams, bleaching creams, vitamin creams, skin lotions, care lotions, ampoules, aftershave lotions, preshaves, humectant lotions, tanning lotions, cellulite creams, depigmentation compositions, massage preparations, body powders, face tonics, deodorants, antiperspirants, nose strips, antiacne compositions, repellents and others.

In a preferred embodiment, a cosmetic composition comprises a daily care O/W formulation, which may contain, for example, the following ingredients in % in accordance with the International Nomenclature of Cosmetic Ingredients, INCI:

A
 1.7 ceteareth-6, stearyl alcohol
 0.7 ceteareth-25
 2.0 diethylamino hydroxybenzoyl hexyl benzoate
 2.0 PEG-14 dimethicone
 3.6 cetearyl alcohol
 6.0 ethylhexyl methoxycinnamate
 2.0 dibutyl adipate
B
 5.0 glycerol
 0.2 disodium EDTA
 1.0 panthenol
 q.s. preservative
 67.8 aqua dem.
C
 4.0 caprylic/capric triglyceride, sodium acrylates copolymer
D
 0.2 sodium ascorbyl phosphate
 1.0 tocopheryl acetate
 0.2 bisabolol
 1.0 caprylic/capric triglyceride, sodium ascorbate, tocopherol, retinol
 1.0 *Lactobacillus* spec.
E
 q.s. sodium hydroxide Phases A and B are separately heated to app. 80° C. Phase B is subsequently stirred into phase A and homogenized. Phase C is stirred into a combination of phases A and B and homogenized. The mixture is under agitation cooled down to app. 40° C.; then phase D is added and the pH is adjusted with phase E to approx. 6.5. The solution is subsequently homogenized and cooled down to room temperature. In a further preferred embodiment, a cosmetic composition comprises a protecting day cream O/W formulation, which may contain, for example, the following ingredients in % in accordance with the International Nomenclature of Cosmetic Ingredients, INCI:

A
 1.7 ceteareth-6, stearyl alcohol
 0.7 ceteareth-25
 2.0 diethylamino hydroxybenzoyl hexyl benzoate
 2.0 PEG-14 dimethicone
 3.6 cetearyl alcohol
 6.0 ethyl hexyl methoxycinnamate
 2.0 dibutyl adipate
B
 5.0 glycerol
 0.2 disodium EDTA
 1.0 panthenol
 q.s. preservative
 68.6 aqua dem.
C
 4.0 caprylic/capric triglyceride, sodium acrylates copolymer
D
 1.0 sodium ascorbyl phosphate
 1.0 tocopheryl acetate
 0.2 bisabolol
 1.0 *Lactobacillus* spec.
E
 q.s. sodium hydroxide Phases A and B are separately heated to app. 80° C. Phase B is subsequently stirred into phase A and homogenized. Phase C is introduced into a combination of phases A and B and homogenized. The mixture is under agitation cooled down to app. 40° C.; then phase D is added and the pH is adjusted with phase E to about 6.5. The solution is subsequently homogenized and cooled down to room temperature. In a further preferred embodiment, a cosmetic composition comprises a skin cleanser O/W formulation, which may contain, for example, the following ingredients in % in accordance with the International Nomenclature of Cosmetic Ingredients, INCI:

A
 10.0 cetearyl ethylhexanoate
 10.0 caprylic/capric triglyceride
 1.5 cyclopentasiloxane, cyclohexasilosane
 2.0 PEG-40 hydrogenated castor oil
B
 3.5 caprylic/capric triglyceride, sodium acrylates copolymer
C
 1.0 tocopheryl acetate
 0.2 bisabolol
 q.s. preservative
 q.s. perfume oil
D
 3.0 polyquaternium-44
 0.5 cocotrimonium methosulfate
 0.5 ceteareth-25
 2.0 panthenol, propylene glycol
 4.0 propylene glycol
 0.1 disodium EDTA
 1.0 *Lactobacillus* spec.
 60.7 aqua dem.

Initially, phase A is dissolved and phase B subsequently stirred into phase A. Subsequently, phase C is introduced into the combination of phases A and B. In a next step, phase D is dissolved and stirred into combined phases A, B and C. The mixture is homogenized and stirred for 15 min.

In a further preferred embodiment, a cosmetic composition comprises a daily care body spray formulation, which may contain, for example, the following ingredients in % in accordance with the International Nomenclature of Cosmetic Ingredients, INCI:

A
 3.0 ethylhexyl methoxycinnamate
 2.0 diethylamino hydroxybenzoyl hexyl benzoate
 1.0 polyquaternium-44
 3.0 propylene glycol
 2.0 panthenol, propylene glycol
 1.0 cyclopentasiloxane, cyclohexasiloxane
 10.0 octyldodecanol
 0.5 PVP
 10.0 caprylic/capric triglyceride
 3.0 C12-15 alkyl benzoate
 3.0 glycerol
 1.0 tocopheryl acetate 0.3 bisabolol
1.0 *Lactobacillus* spec.
59.2 alcohol The components of phase A are weighed out and dissolved until clearness. In a further preferred embodiment, a cosmetic composition comprises a skin gel, which may contain, for example, the following ingredients in % in accordance with the International Nomenclature of Cosmetic Ingredients, INCI:

3.6 PEG-40 hydrogenated castor oil
15.0 alcohol
0.1 bisabolol
0.5 tocopheryl acetate
q.s. perfume oil B
3.0 panthenol
0.6 carbomer
1.0 *Lactobacillus* spec.
75.4 aqua dem, C
0.8 triethanolamine Initially, phase A is dissolved until clearness. Phase B is macerated and subsequently neutralized with phase C. In a next step, phase A is stirred into the homogenized phase B and the mixture is homogenized.

In yet a further preferred embodiment, a cosmetic composition comprises an after shave lotion, which may contain, for example, the following ingredients in % in accordance with the International Nomenclature of Cosmetic Ingredients, INCI:

A
10.0 cetearyl ethylhexanoate
5.0 tocopheryl acetate
1.0 bisabolol
0.1 perfume oil
0.3 acrylates/c10-30 alkyl acrylate crosspolymer B
15.0 alcohol
1.0 panthenol
3.0 glycerol
1.0 *Lactobacillus* spec.
0.1 triethanolamine
63.5 aqua dem.

The component of phase A are mixed. In a next step, phase B is dissolved and introduced into phase A and subsequently homogenized.

The present invention also relates to the use of a microorganism according to the invention or of a derivative, mutant or inactive form thereof as described herein above for the preparation of a pharmaceutical composition for preventing or treating dermatitis, preferably atopic dermatitis, psoriasis, poison-ivy dermatitis, eczema herpeticum, kerion or scabies.

In another aspect the present invention relates to a method for the production of a composition comprising the step of formulating a microorganism of the invention or a derivative or mutant thereof or an inactive form as described herein above with a cosmetically and/or pharmaceutically carrier or excipient.

The present invention furthermore relates to a method of preventing or treating dermatitis, preferably atopic dermatitis, psoriasis, poison-ivy dermatitis, eczema herpeticum, kerion or scabies comprising the step of administering to a patient in need thereof a prophylactically or therapeutically effective amount of a composition according to the invention.

It is to be understood that this invention is not limited to the particular methodology, protocols, bacteria, vectors, and reagents etc. described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nadel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

It must be noted that as used herein and in the appended claims, the singular forms "a", "an", and "the", include plural referents unless the context clearly indicates otherwise. Thus, for example, reference to "a reagent" includes one or more of such different reagents, and reference to "the method" includes reference to equivalent steps and methods known to those of ordinary skill in the art that could be modified or substituted for the methods described herein.

In a second aspect the present invention relates to a microorganism which is able to inhibit the growth of one or more microorganisms of the transient pathogenic skin micro flora and which does not inhibit the growth of microorganisms of the healthy normal resident skin micro flora.

The inventors surprisingly found that an effective protection of the skin against a colonization by pathogenic microorganisms can be achieved by administering to the skin the above described microorganisms or inactivated forms thereof. The inventors for the first time identified corresponding microorganisms and provided methods for their identification. These microorganisms are able to differentially suppress the growth of microorganisms on the skin, i.e. they selectively inhibit the growth of pathogenic microorganisms, but do not influence the growth of the inhabitants of the healthy commensal micro flora. Thereby these microorganisms are able to regenerate and to stabilize the natural skin flora.

Many different microorganisms exist on the skin. Some belong to the normal (resident) flora of the skin and are harmless commensals and some are potential pathogens.

Basically, organisms on the skin can be classified into two categories:

1. Resident organisms: resident organisms are permanent inhabitants of the skin which colonise on the surface of the skin, the stratum corneum and within the outer layer of the epidermis and the deeper crevices of the skin and hair follicles. These microorganisms of the resident microbial skin flora can grow and multiply on the skin without invading or damaging the skin tissue. Washing does not easily remove these organisms in deeper skin regions. Resident microorganisms are harmless commensals.

2. Transient organisms: transient organisms are microorganisms which are deposited on the skin but do not multiply there or contaminants which multiply on the skin and persist for short periods. They cannot settle permanently on healthy skin whose microenvironment is heavily determined by the resident skin micro flora. Transient organisms are potentially pathogenic.

Thus, the term "transient pathogenic skin micro flora" refers to microorganisms which are deposited on the skin but do not multiply there or to contaminants which multiply on the skin and persist for short periods. In particular, if a microorganism is applied to the skin and is unable to grow and reproduce there under the environmental conditions provided by the healthy skin and cannot permanently colonize this organ (or a region of it), it is considered to belong to the transient pathogenic skin micro flora. Several bacteria, yeast and fungi can be transiently isolated from human skin but particularly the following microorganism can be classified to the transient pathogenic skin micro flora due to their frequent appearance: *Staphylococcus aureus, Streptococcus pyogenes*, gram-negative bacilli (e.g *Acinetobacter calcoaceticus*), *Candida albicans* and *Malassezia furfur*. Microorganisms of the transient micro flora often have pathogenic factors that allow the bacterium to attach to disordered skin regions. This can e.g. be the attachment to collagen structures or keratin structures.

The constituents and the composition of the microbial skin flora can be determined quantitatively and qualitatively, e.g. by peeling off the upper skin layers with scotch tape. Microorganisms of the skin micro flora can be identified within the upper ten skin layers peeled off, e.g., by scotch tape. Exemplary, to isolate these microorganisms six 2 cm$^2$ scotch tapes are each pressed on a defined region of the skin, preferably of the forearm and afterwards each tape stripe is transferred from the skin to a selective culture agar plate for either gram positive (e.g. BHI, Difco Inc.) or gram negative bacteria (e.g. MacConkey agar, Difco Inc.) or to a selective culture agar for yeasts and fungi (e.g. Plate Count Agar, Difco Inc.). Afterwards the microorganisms that have been transferred from skin to culture agar plates are cultivated at 30° C. and 37° C., aerobically and anaerobically for about 24 hours. Colony forming units are determined by morphological and biochemical methods for a qualitative analysis and by counting for quantification. The relative composition and total cell counts are determined. The person skilled in the art can determine the genus and/or species of the microorganisms of the skin micro flora which have been isolated as described above by methods known in the art.

The microorganisms of the transient pathogenic skin micro flora can be determined, e.g., by metabolic footprinting, the evaluation of fatty acid composition and the composition of the cell wall, sequencing of 16S ribosomal RNA or the detection of specific DNA probes encoding specific pathogenic factors.

A microorganism is regarded as inhibiting the growth of a microorganism of the transient pathogenic skin micro flora if it leads to a decrease of growth of such a microorganism of the transient pathogenic skin micro flora when contacted with it. The term "inhibits the growth of microorganisms of the transient pathogenic skin micro flora" means that the microorganism of the invention decreases the growth of at least one, preferably of more than one, preferably of more than two, more preferably of more than five and particularly preferred of any of the microorganisms of the transient pathogenic flora. In a further preferred embodiment, the microorganism of the present invention inhibits the growth of the major representative of the transient pathogenic skin micro flora, i.e. *Staphylococcus aureus*. In a further preferred embodiment, the microorganism of the present invention specifically inhibits the growth of *Staphylococcus aureus*. "Specifically" preferably means that it inhibits the growth of *Staphylococcus aureus*, but does not significantly or only to a minor degree inhibit the growth of other microorganisms, in particular of those microorganisms which belong to the resident skin micro flora. More preferably, the term "specifically" means that the degree of inhibition on *Staphylococcus* is much higher than the degree of inhibition on another microorganism, in particular a microorganism of the resident skin micro flora. Particularly preferred, the term "specifically" means that in a suitable growth assay known to the person skilled in the art the proliferation of *Staphylococcus aureus* in the presence of the microorganism of the present invention is at the most 50% of the proliferation of another microorganism, in particular another microorganism of the resident skin micro flora in the presence of the microorganism of the present invention. Preferably, the proliferation of *Staphylococcus aureus* is 40%, 30%, 20%, 10%, more preferably 5% and most preferably 0% of the proliferation of another microorganism, in particular another microorganism of the resident skin micro flora, in the presence of a microorganism of the present invention. The specific inhibition of *Staphylococcus aureus* is indicated in Examples 10 and 11, which show by way of illustration that *Micrococcus luteus* and *Escherichia coli* are not inhibited by a microorganism according to the present invention in an in vitro liquid assay. In a preferred embodiment the microorganism of the present invention inhibits the growth of *Staphylococcus aureus* but does not inhibit the growth of *Micrococcus luteus* and/or *Escherichia coli*.

In a particularly preferred embodiment the specific inhibition of *Staphylococcus aureus* can be detected when culture conditions are used which include glycerol.

A decreased growth means preferably a decrease in proliferation, i.e. in cell divisions per unit. Alternatively, the term "inhibits" also refers to a decrease in size of individual cells. Bacterial cell size can be assessed by flow cytometry (e.g. Becton-Dickinson FACSort flow cytometer, San Jose, Calif.) after staining with the stain SYBR Green I (Molecular Probes, USA). Bacteria cell size is assessed in Side-Angle Light Scatter (SSC) mode.

A decreased growth thus means a decrease in biomass production per time unit.

The inhibition of growth of the microorganism(s) of the transient pathogenic skin micro flora can preferably be observed in vitro, more preferably in an assay in which a microorganism according to the invention is contacted with one or more microorganisms of the transient pathogenic skin micro flora and the growth of the(se) microorganism(s) of the transient pathogenic skin micro flora is determined. The growth can be determined by counting the numbers of cells/colonies after different time intervals of incubation and can be compared with a control which does not contain a microorganism according to the invention, thereby allowing to determine whether there is an increase or decrease in growth.

An in vitro assay for determining the inhibition of growth is described in the Examples and comprises a so-called "in vitro hole plate assay". In brief, such an assay comprises the following steps:

cultivation of at least one microorganism of the transient pathogenic skin micro flora and evenly spreading it/them on a prepared agar plate containing a suitable agar medium for growth, and preferably detection, of the respective microorganism(s);
providing holes in the inoculated agar plate;
filling the holes with precultured cells of a microorganism according to the invention;
incubating the agar plates for an appropriate amount of time and under conditions allowing growth of the microorganism(s) of the transient pathogenic skin micro flora; and
determining the growth of the microorganism(s) of the transient pathogenic skin micro flora surrounding the holes containing a microorganism according to the invention and comparing it to the growth of the microorganism(s) surrounding a hole which does not contain a microorganism according to the invention.

The determination of the growth in the last step may be effected by available means and methods for determining the number of cells and/or colonies, e.g. by staining with an appropriate dye and/or optical means such as densitometry and counting the cells/colonies under the microscope. In a preferred embodiment the diameter of the occurring clearing zone next to the hole may be used to determine the area of inhibition.

More preferably, the inhibition of growth of the microorganism(s) of the transient pathogenic skin micro flora can be determined in an "in vitro liquid assay". Such an assay is described in the Examples and, briefly, comprises the following steps:
cultivation of at least one microorganism of the transient pathogenic skin micro flora in a liquid culture;
applying an aliquot of a liquid culture of the microorganism according to the invention and an aliquot of a liquid culture of the microorganism of the transient pathogenic skin micro flora to a culture medium allowing the growth of the microorganism of the transient pathogenic skin micro flora;
co-cultivation of the microorganism according to the invention and the microorganism of the transient pathogenic skin micro flora in a liquid culture;
transferring an aliquot of the co-cultivation liquid culture to an agar plate, containing an appropriate growth medium;
incubation of the agar plates for a period of time and under conditions allowing the growth of the microorganism(s) of the transient pathogenic skin micro flora;
determining the growth of the microorganism(s) of the transient pathogenic skin micro flora by quantification of the colony forming units and comparing it to the growth of the microorganism(s) in a control in which no microorganism of the invention was applied.

Even more preferably, the inhibition of growth of the microorganism(s) of the transient pathogenic skin micro flora can also be observed in an "in situ skin assay". Such assay is described in the Examples and, in brief, comprises the following steps:
cultivation of at least one microorganism of the transient pathogenic skin micro flora and evenly spreading it on an area of skin of a test individual;
applying an aliquot of a microorganism according to the invention in a punctual area within the area on which the microorganism(s) of the transient pathogenic skin micro flora has/have been spread;
incubating the skin for an amount of time sufficient to allow growth of the microorganism(s) of the transient pathogenic skin micro flora;
transferring the upper skin layers, including the microorganisms comprised in these, to an agar plate containing an appropriate growth medium;
incubation of the agar plates for a period of time and under conditions allowing the growth of the microorganism(s) of the transient pathogenic skin micro flora;
determining the growth of the microorganism(s) of the transient pathogenic skin micro flora surrounding the area at which the microorganism according to the invention was applied and comparing it to the growth of the microorganism(s) in a control in which no microorganism of the invention was applied.

The area of skin used for this assay may be any suitable area of skin of an individual, preferably of a human individual. In a preferred embodiment it is an area of skin on the forearm of a human individual. The size of the area is not decisive, preferably it is about 1 to 40 $cm^2$, more preferably 5 to 20 $cm^2$, even more preferably 5 to 10 $cm^2$, e.g. about 5, 6, 7, 8, 9 or 10 $cm^2$.

The microorganism(s) of the transient pathogenic skin micro flora are evenly distributed on the area, preferably in a density of approximately $10^2$ cfu/$cm^2$-$10^3$ cfu/$cm^2$. The microorganism(s) spread on the skin are air dried and an aliquot of a microorganism according to the invention is applied in a punctual manner within the area. This can be achieved by means known to the person skilled in the art. For example, the microorganisms according to the invention are centrifuged (15 min, 4000×g). The cell pellet is washed two times with K/Na-buffer (each 1 ml). Cells are resuspended in 200 µl K/Na buffer and 10 µl of prepared microorganisms are punctual applied on the pre-inoculated skin area with a micro pipet.

The incubation of the skin preferably takes place at room temperature for, e.g., two hours. The transfer of the upper skin layers, including the microorganisms comprised therein, may, e.g., be effected with the help of an adhesive tape stripe. The agar plates to which the upper skin layers have been transferred are incubated at a temperature allowing growth of the microorganism(s) or the transient pathogenic skin micro flora to be tested and contain a growth medium known to support growth of this (these) microorganism(s). The incubation typically takes place for about 24 hours.

The growth of the microorganism(s) can be detected by methods known to the person skilled in the art. Preferably, it is determined by densitometry or by counting the colonies formed in the neighborhood of the point at which an aliquot of the microorganism of the invention was applied. Bacterial cell size can be assessed by flow cytometry (e.g. Becton-Dickinson FACSort flow cytometer, San Jose, Calif.) after staining with the stain SYBR Green I (Molecular Probes, USA). Bacteria cell size is assessed in Side-Angle Light Scatter (SSC) mode.

A microorganism is regarded to inhibit the growth of one or more microorganisms of the pathogenic transient micro flora if it leads to a decrease of growth of at least one such microorganism in an "in vitro hole plate assay" of at least 5%, preferably of at least 10%, 20%, 30%, 40%, 50%, 60%, or 70%, 80%, more preferably of at least 90% and even more preferably of at least 95% and most preferably of at least 99% in comparison to a control to which no microorganism has been added. More preferably, a microorganism is regarded to inhibit the growth of one or more microorganisms of the pathogenic transient micro flora if it leads to a decrease of growth of at least one such microorganism in an "in vitro liquid assay" of at least 5%, preferably of at least 10%, 20%, 30%, 40%, 50%, 60%, or 70%, 80%, more preferably of at least 90% and even more preferably of at least 95% and most preferably of at least 99% in comparison to a control to which no microorganism has been added.

Most preferably, a microorganism is regarded as inhibiting the growth of one or more microorganisms of the transient pathogenic skin micro flora if it leads to an decrease of growth of at least one such microorganism in an in situ skin assay of at least 5%, preferably of at least 10%, 20%, 30%, 40%, 50%, 60%, or 70%, 80%, more preferably of at least 90%, even more preferably of at least 95% and most preferably of at least 99%.

The test for determining whether a microorganism inhibits or does not inhibit the growth of a microorganism of the transient pathogenic skin micro flora, e.g. *Staphylococcus aureus*, is preferably an in vitro and/or an in situ test as described herein-above, more preferably a test as described in the Examples.

In a preferred embodiment the microorganism according to the invention leads to an inhibition of the growth of one or more microorganisms of the pathogenic transient micro flora, preferably *Staphylococcus aureus*, which is comparable to the inhibition of growth of at least one such micro-microorganism after the use of an antibiotic. The term "comparable" means that the inhibitory activity of a specific amount of the microorganism according to the invention is within the same range as the activity of an antibiotic. In particular, this effect can be achieved by using preferably an amount of between $1.0 \times 10^8$ and $3.0 \times 10^9$ cells, more preferably between $2.0 \times 10^8$ and $1.0 \times 10^9$ cells, even more preferably between $3.0 \times 10^8$ and $5.0 \times 10^8$ cells and most preferably at $3.4 \times 10^8$ cells and the inhibitory activity achieved by this amount of cells corresponds preferably to 5 to 15 units of an antibiotic. The term "antibiotic" refers to a chemical substance which has the capacity to inhibit the growth or to kill microorganisms. Such substances are known to the person skilled in the art. Preferably, the term refers to beta-lactam compounds like penicillines, cephalosporins or carbapenems; macrolides; tetracyclines; fluoroquinolones; sulphonamides; aminoglycosides; imidazoles; peptide-antibiotics and lincosamides. More preferably, the term relates to bacitracin and erythromycin. In a preferred embodiment the term "comparable" means that the inhibitory activity of about $3.4 \times 10^8$ cells of a microorganism of the present invention corresponds to about 150 μg of bacitracin or about 2.5 μg of erythromycin. Most preferably the term "comparable" relates to the inhibitory activity of about $3.4 \times 10^8$ cells of a microorganism of the present invention corresponds to about 150 μg of bacitracin or about 2.5 μg of erythromycin on *Staphylococcus aureus* as indicator strain, as illustrated in Example 12.

The term "microorganisms of the pathogenic transient micro flora" has been described herein above. Preferably, the term relates to *Staphylococcus aureus*. The degree of growth inhibition of the microorganism(s) of the transient pathogenic skin micro flora in comparison to the inhibition of growth of at least one such microorganism after the use of an antibiotic can preferably be observed in vitro, more preferably in an assay in which a microorganism according to the invention is contacted with one or more microorganisms of the transient pathogenic skin micro flora and the growth of the(se) microorganism(s) of the transient pathogenic skin micro flora is determined. Most preferably, the comparison of growth inhibition can be determined in an "in vitro hole plate assay" as described in the Examples and mentioned herein above. In brief, such a comparison in an "in vitro hole plate assay" comprises the following steps cultivation of at least one microorganism of the transient pathogenic skin micro flora and evenly spreading it/them on a prepared agar plate containing a suitable agar medium for growth, and preferably detection, of the respective microorganism(s);

providing holes in the inoculated agar plate;

filling some of the holes with precultured cells of a microorganism according to the invention and filling some of the holes with an antibiotic at different concentrations;

incubating the agar plates for an appropriate amount of time and under conditions allowing growth of the microorganism(s) of the transient pathogenic skin micro flora;

determining the growth of the microorganism(s) of the transient pathogenic skin micro flora surrounding the holes containing a microorganism according to the invention and comparing it to the growth of the microorganism(s) surrounding a hole which contains an antibiotic at different concentrations;

measurement of the diameter of the inhibition zones of the holes and calculation of the area of inhibition; and correlation of the growth inhibition caused by a microorganism according to the invention and an antibiotic.

In a preferred embodiment the term "inhibits the growth of microorganisms of the transient pathogenic skin micro flora" means that the decrease of growth of microorganisms of the transient pathogenic skin micro flora is due to the release of (defensive) antimicrobial substances. The term "antimicrobial substance" refers to a substance that is able to mediate the selective inhibition of growth of microorganisms of the transient pathogenic skin micro flora. Preferably the substance is not sensitive against protease digestion. The term "not sensitive" means that the substance is not or only partially affected by protease activity. The term "protease" refers to any enzyme that catalyses the splitting of interior peptide bonds in a protein, known to the person skilled in the art. In a preferred embodiment the term refers to proteinase K, a protease from *Streptomyces griseus*, trypsin or chymotrypsin. The term "protease digestion" refers to a protease reaction under conditions known to the person skilled in the art. In a preferred embodiment the term refers to an incubation at 37° C., for example for one our.

In a further preferred embodiment the term "antimicrobial substance" refers to a substance that is characterized by its property not to be disturbed at high or low pH values. The term "not to be disturbed" means that the substance is stable and biologically active. The terms "high pH value" and "low pH value" are known to the person skilled in the art. Preferably, the property not to be disturbed is present between pH 3 and pH 11.

The microorganism according to the invention is also characterized in that it does not inhibit the growth of the healthy normal resident skin micro flora. Thus, the terms "resident skin micro flora" and "healthy normal resident skin micro flora" relate to microorganisms which can normally be found on healthy skin, preferably human skin, and which constitute the majority of the microorganisms found on the skin.

In particular, the term "resident skin micro flora" relates to microorganisms which are permanent inhabitants on the surface of the skin, the stratum corneum and within the outer layer of the epidermis and the deeper crevices of the skin and hair follicles. These microorganisms are characterized in that they can grow and multiply on the skin without invading or damaging the skin tissue. A characteristic of these microorganisms is that washing does not easily remove them in deeper skin regions. The microorganisms of the resident skin micro flora are harmless commensals.

The term "resident skin micro flora" preferably relates to a flora of aerobic and anaerobic microorganisms which can be found on skin, preferably human skin. More preferably, it relates to a flora of microorganisms which comprises *Staphylococcus epidermidis* (coagulase negative), *Micrococcus* spec., Diphteroids and propioni bacteria. Typically, about 90% of the aerobic resident microbial skin flora consists of *Staphylococcus epidermidis*. The remaining about 10% are composed of mainly *Micrococcus* spec. (80% *Micrococcus luteus*) and Diphteroids (13%). The term "Diphtheroid" denotes a wide range of bacteria belonging to the genus *Corynebacterium*. For convenience, cutaneous diphtheroids have been categorized into the following four groups: lipophilic or nonlipophilic diphtheroids; anaerobic diphtheroids; diphtheroids producing porphyrins. Major representatives (90%) of the anaerobic microbial skin flora are propionibacteria; especially *Propionibacterium acnes, P. granulosum* and *P. avidum* can be isolated from the skin. The anaerobic flora accounts for approximately 4% of the total resident skin flora.

More preferably, more than 90% of the microorganisms of the micro flora belong to *Staphylococcus epidermidis, Micrococcus* spec., Diphteroids and propioni bacteria. Even more preferably, the resident skin micro flora is characterized in that its major constituent is *Staphylococcus epidermidis*.

The term "skin" refers to the body's outer covering, as known to the person skilled in the art. Preferably the term relates to three layers: epidermis, dermis, and subcutaneous fatty tissue. The epidermis is the outermost layer of the skin. It typically forms the waterproof, protective wrap over the body's surface and is made up of stratified squamous epithelium with an underlying basal lamina. It usually contains no blood vessels, and is nourished by diffusion from the dermis. The main type of cells which make up the epidermis are keratinocytes, with melanocytes and Langerhans cells also present. The epidermis is divided into several layers where cells are formed through mitosis at the innermost layers. They move up the strata changing shape and composition as they differentiate and become filled with keratin. They eventually reach the top layer called stratum corneum and become sloughed off, or desquamated. The outermost layer of the epidermis consists of 25 to 30 layers of dead cells. Conventionally, the epidermis is divided into 5 sublayers or strata (from superficial to deep): the stratum corneum, the stratum lucidum, the stratum granulosum, the stratum spinosum and the stratum germinativum or stratum basale. Typically, the interface between the epidermis and dermis is irregular and consists of a succession of papillae, or fingerlike projections, which are smallest where the skin is thin and longest in the skin of the palms and soles. Typically, the papillae of the palms and soles are associated with elevations of the epidermis, which produce ridges. Subcutaneous fatty tissue is the deepest layer of the skin. A characteristic of this layer is that it is composed of connective tissue, blood vessels, and fat cells. Typically, this layer binds the skin to underlying structures, insulates the body from cold, and stores energy in the form of fat. In general the skin forms a protective barrier against the action of physical, chemical, and bacterial agents on the deeper tissues. This means that tissues belonging, e.g. to the oral cavity or the vaginal region or mucous membranes do not belong to the skin. In a preferred embodiment the term "skin" relates to the outermost layer of the body's covering, i.e. the epidermis. In a more preferred embodiment the term "skin" relates to the stratum corneum of the epidermis. In an even more preferred embodiment the term skin relates to the outermost 25 to 30 layers of dead cells of the epidermis. In the most preferred embodiment the term "skin" relates to the outermost 10 layers of dead cell of the epidermis The term "not inhibit" in connection with the growth of microorganisms of the resident skin micro flora means that the growth of at least one, preferably of more than one, preferably of more than two, more preferably of more than five and particularly preferred of any of the microorganisms of the resident skin micro flora is not altered when contacted with a microorganism according to the invention. A not altered growth means preferably an unchanged proliferation, i.e. cell divisions per time unit.

A microorganism is regarded as not altering the growth of a microorganism of the resident skin micro flora if it does not lead to an decreased growth of such a microorganism of the resident skin micro flora when contacted with it. The inhibition of growth or its absence can be tested in vitro or in situ as described above in connection with the property of a microorganism of the invention to inhibit the growth of at least one microorganism of the transient pathogenic skin micro flora. Most preferably the test for determining inhibition or its absence takes place by carrying out an "in vitro hole plate assay" and/or "in vitro liquid assay" and/or an "in situ skin assay" with a microorganism of the resident skin micro flora as explained herein below, more preferably as described in the Examples.

In brief, an "in vitro hole plate assay" with a microorganism of the resident skin micro flora comprises the following steps:

cultivation of at least one microorganism of the resident skin microbial flora and evenly spreading it/them on a prepared agar plate containing a suitable agar medium for growth, and preferably detection, of the respective microorganism(s);

providing holes in the inoculated agar plate;

filling the holes with precultured cells of a microorganism according to the invention;

incubating the agar plates for an appropriate amount of time and under conditions allowing growth of the microorganism(s) of the resident skin microbial flora; and determining the growth of the microorganism(s) of the resident skin microbial flora surrounding the holes containing a microorganism according to the invention and comparing it to the growth of the microorganism(s) surrounding a hole which does not contain a microorganism according to the invention.

The determination of the growth in the last step may be effected by available means and methods for determining the number of cells and/or colonies, e.g. by staining with an appropriate dye and/or optical means such as densitometry and counting the cells/colonies under the microscope. In a preferred embodiment the diameter of the occurring clearing zone next to the hole may be used to determine the area of inhibition.

An assay "in vitro liquid assay" with a microorganism of the resident skin micro flora is described in the Examples and, briefly, comprises the following steps:

cultivation of at least one microorganism of the resident skin micro flora in a liquid culture;

applying an aliquot of a liquid culture of the microorganism according to the invention and an aliquot of a liquid culture of the microorganism of the resident skin micro flora to a culture medium allowing the growth of the microorganism of the resident skin micro flora;

co-cultivation of the microorganism according to the invention and the microorganism of the resident skin micro flora in a liquid culture;

transferring an aliquot of the co-cultivation liquid culture to an agar plate, containing an appropriate growth medium;

incubation of the agar plates for a period of time and under conditions allowing the growth of the microorganism(s) of the resident skin micro flora;

determining the growth of the microorganism(s) of the resident skin micro flora by quantification of the colony forming units and comparing it to the growth of the microorganism(s) in a control in which no microorganism of the invention was applied.

In brief, an "in situ skin assay" with a microorganism of the resident skin micro flora comprises the following steps:

cultivation of at least one microorganism of the resident skin micro flora and evenly spreading it on an area of skin of a test individual;

applying an aliquot of a microorganism according to the invention in a punctual area within the area on which the microorganism(s) of the resident skin micro flora has/have been spread;

incubating the skin for an amount of time sufficient to allow growth of the microorganism(s) of the resident skin micro flora;

transferring the upper skin layers, including the microorganisms comprised in these, to an agar plate containing an appropriate growth medium;

incubation of the agar plates for a period of time and under conditions allowing the growth of the microorganism(s) of the resident skin micro flora;

determining the growth of the microorganism(s) of the resident skin micro flora surrounding the area at which the microorganism according to the invention was applied and comparing it to the growth of the microorganism(s) in a control in which no microorganism of the invention was applied.

A microorganism is regarded as not altering the growth of a microorganism of the resident skin micro flora if the growth of the latter microorganism is not decreased or only slightly decreased when contacted with the former microorganism. "Slightly decreased" means that the growth is decreased not more than by 5% when compared to the control, more preferably not more than 2% when compared to the control. The term "not decreased" means that there can be found no statistically relevant difference between the growth of the microorganism of the resident skin micro flora contacted with a microorganism of the invention when compared to the control where no microorganism of the invention is present. The term "not decreased" in a preferred embodiment also includes those cases where a microorganism actually leads to an increase of the growth of a microorganism of the resident skin micro flora, i.e. where it stimulates the growth of such a microorganism. In another preferred embodiment the microorganism of the present invention does not negatively influence the growth of the microorganisms of the resident skin micro flora. The term "not negatively influence" means that that there can be found no inhibition of the growth of the microorganism of the resident skin micro flora contacted with a microorganism of the invention when compared to the control where no microorganism of the invention is present.

In a particularly preferred embodiment the microorganism of the present invention is a microorganism belonging to the group of lactic acid bacteria. The term "microorganism belonging to the group of lactic acid bacteria" encompasses (a) microorganism(s) which belong(s) to bacteria, in particular belonging to gram-positive fermentative eubacteria, more particularly belonging to the family of lactobacteriaceae including lactic acid bacteria. Lactic acid bacteria are from a taxonomical point of view divided up into the subdivisions of *Streptococcus, Leuconostoc, Pediococcus, Lactococcus* and *Lactobacillus*. The microorganism of the present invention is preferably a *Lactobacillus* species. Members of the lactic acid bacteria group normally lack porphyrins and cytochromes, do not carry out electron-transport phosphorylation and hence obtain energy only by substrate-level phosphorylation. I.e. in lactic acid bacteria ATP is synthesized through fermentation of carbohydrates. All of the lactic acid bacteria grow anaerobically, however, unlike many anaerobes, most lactic acid bacteria are not sensitive to oxygen and can thus grow in its presence as well as in its absence. Accordingly, the bacteria of the present invention are preferably aerotolerant anaerobic lactic acid bacteria, preferably belonging to the genus of *Lactobacillus*.

The lactic acid bacteria of the present invention are preferably rod-shaped or spherical, varying from long and slender to short bent rods, are moreover preferably immotile and/or asporogenous and produce lactic acid as a major or sole product of fermentative metabolism. The genus *Lactobacillus* to which the microorganism of the present invention belongs in a preferred embodiment is divided up by the following characteristics into three major subgroups, whereby it is envisaged that the *Lactobacillus* species of the present invention can belong to each of the three major subgroups:

(a) homofermentative lactobacilli
  (i) producing lactic acid, preferably the L-, D- or DL-isomer(s) of lactic acid in an amount of at least 85% from glucose via the Embden-Meyerhof pathway;
  (ii) growing at a temperature of 45° C., but not at a temperature of 15° C.,
  (iii) being long-rod shaped; and
  (iv) having glycerol teichoic acid in the cell wall;

(b) homofermantative lactobacilli
  (i) producing lactic acid, preferably the L- or DL-isomer(s) of lactic acid via the Embden-Meyerhof pathway;
  (ii) growing at a temperature of 15° C., showing variable growth at a temperature of 45° C.;
  (iii) being short-rod shaped or coryneform; and
  (iv) having ribitol and/or glycerol teichoic acid in their cell wall;

(c) heterofermentative lactobacilli
  (i) producing lactic acid, preferably the DL-isomer of lactic acid in an amount of at least 50% from glucose via the pentose-phosphate pathway;
  (ii) producing carbondioxide and ethanol
  (iii) showing variable growth at a temperature of 15° C. or 45° C.;
  (iv) being long or short rod shaped; and
  (v) having glycerol teichoic acid in their cell wall.

Based on the above-described characteristics, the microorganisms of the present invention can be classified to belong to the group of lactic acid bacteria, particularly to the genus of *Lactobacillus*. By using classical systematics, for example, by reference to the pertinent descriptions in "Bergey's Manual of Systematic Bacteriology" (Williams & Wilkins Co., 1984), a microorganism of the present invention can be determined to belong to the genus of *Lactobacillus*. Alternatively, the microorganisms of the present invention can be classified to belong to the genus of *Lactobacillus* by methods known in the art, for example, by their metabolic fingerprint, i.e. a comparable overview of the capability of the microorganism(s) of the present invention to metabolize sugars or by other methods described, for example, in Schleifer et al., System. Appl. Microb., 18 (1995), 461-467 or Ludwig et al., System. Appl. Microb., 15 (1992), 487-501. The microorganisms of the present invention are capable of metabolizing sugar sources which are typical and known in the art for microorganisms belonging to the genus of *Lactobacillus*.

The affiliation of the microorganisms of the present invention to the genus of *Lactobacillus* can also be characterized by using other methods known in the art, for example, using SDS-PAGE gel electrophoresis of total protein of the species to be determined and comparing them to known and already characterized strains of the genus *Lactobacillus*. The techniques for preparing a total protein profile as described above, as well as the numerical analysis of such profiles, are well known to a person skilled in the art. However, the results are only reliable insofar as each stage of the process is sufficiently standardized. Faced with the requirement of accuracy when determining the attachment of a microorganism to the genus of *Lactobacillus*, standardized procedures are regularly made available to the public by their authors such as that of Pot et al., as presented during a "workshop" organized by the European Union, at the University of Ghent, in Belgium, on Sep. 12 to 16, 1994 (Fingerprinting techniques for classification and identification of bacteria, SDS-PAGE of whole cell protein). The software used in the technique for analyzing the SDS-PAGE electrophoresis gel is of crucial importance since the degree of correlation between the species depends on the parameters and algorithms used by this software. Without going into the theoretical details, quantitative comparison of bands measured by a densitometer and normalized by a computer is preferably made with the Pearson correlation coefficient. The similarity matrix thus obtained may be organized with the aid of the UPGMA (unweighted pair group method using average linkage) algorithm that not only makes it possible to group together the most similar profiles, but also to construct dendograms (see Kersters, Numerical methods in the classification and identification of bacteria by electrophoresis, in Computer-assisted Bacterial Systematics, 337-368, M. Goodfellow, A. G. O'Donnell Ed., John Wiley and Sons Ltd, 1985).

Alternatively, the affiliation of said microorganisms of the present invention to the genus of *Lactobacillus* can be characterized with regard to ribosomal RNA in a so called Riboprinter® More preferably, the affiliation of the newly identified species of the invention to the genus *Lactobacillus* is demonstrated by comparing the nucleotide sequence of the 16S ribosomal RNA of the bacteria of the invention, or of their genomic DNA which codes for the 16S ribosomal RNA, with those of other genera and species of lactic acid bacteria known to date. Another preferred alternative for determining the attachment of the newly identified species of the invention to the genus *Lactobacillus* is the use of species-specific PCR primers that target the 16S-23S rRNA spacer region. Another preferred alternative is RAPD-PCR (Nidatu et al. in Antonie van Leeuwenhoek (79), 1-6, 2001) by virtue of that a strain specific DNA pattern is generated which allows to determine the affiliation of an identified microorganisms in accordance with the present invention to the genus of *Lactobacillus*. Further techniques useful for determining the affiliation of the microorganism of the present invention to the genus of *Lactobacillus* are restriction fragment length polymorphism (RFLP) (Giraffa et al., Int. J. Food Microbiol. 82 (2003), 163-172), fingerprinting of the repetitive elements (Gevers et al., FEMS Microbiol. Lett. 205 (2001) 31-36) or analysis of the fatty acid methyl ester (FAME) pattern of bacterial cells (Heyrman et al., FEMS Microbiol. Lett. 181 (1991), 55-62). Alternatively, lactobacilli can be determined by lectin typing (Annuk et al., J. Med. Microbiol. 50 (2001), 1069-1074) or by analysis of their cell wall proteins (Gatti et al., Lett. Appl. Microbiol. 25 (1997), 345-348.

In a preferred embodiment of the present application the microorganism is a probiotic *Lactobacillus* species. The term "probiotic" in the context of the present invention means that the microorganism has a beneficial effect on health if it is topically applied to the skin. Preferably, a "probiotic" microorganism is a live microorganism which, when topically applied to the skin, is beneficial for health of this tissue. Most preferably, this means that the microorganism has a positive effect on the micro flora of the skin.

In a preferred embodiment the microorganism of the present invention belongs to the species of *Lactobacillus buchneri* or *Lactobacillus delbrückii*. However, the *Lactobacillus* species are not limited thereto.

In a particularly preferred embodiment of the present invention the microorganism of the present invention is selected from the group consisting of *Lactobacillus buchneri*, or *Lactobacillus delbrückii* being deposited at the DSMZ under the accession number DSM 18007 (*Lactobacillus buchneri* OB-LB-Sa16) and DSM 18006 (*Lactobacillus delbrückii* ssp. *delbrückii* OB-LB-Sa3). The invention also relates to a mutant or derivative of the above-mentioned deposited *Lactobacillus* strains wherein said mutants or derivatives have retained their capability to stimulate the growth of at least one microorganism of the resident skin micro flora and their property not to stimulate the growth of microorganisms of the transient pathogenic skin micro flora. The term "*Lactobacillus buchneri* or *Lactobacillus delbrückii* being deposited at the DSMZ under the accession number" relates to cells of a microorganism belonging to the species *Lactobacillus buchneri*, or *Lactobacillus delbrückii* deposited at the Deutsche Sammlung für Mikroorganismen and Zellkulturen (DSMZ) on Feb. 24, 2006 and having the following deposit numbers: DSM 18007 (*Lactobacillus buchneri* OB-LB-Sa16) and DSM 18006 (*Lactobacillus delbrückii* ssp. *delbrückii* OB-LB-Sa3). The DSMZ is located at the Mascheroder Weg 1 b, D-38124 Braunschweig, Germany. The aforementioned deposits were made pursuant to the terms of the Budapest treaty on the international recognition of the deposit of microorganisms for the purposes of patent procedures.

In a particular preferred embodiment the microorganisms of the present invention are "isolated" or "purified". The term "isolated" means that the material is removed from its original environment, e.g. the natural environment if it is naturally occurring, or the culture medium if it is cultured. For example, a naturally-occurring microorganism, preferably a *Lactobacillus* species, separated from some or all of the coexisting materials in the natural system, is isolated. Such a microorganism could be part of a composition, and is to be regarded as still being isolated in that the composition is not part of its natural environment.

The term "purified" does not require absolute purity; rather, it is intended as a relative definition. Individual microorganisms obtained from a library have been conventionally purified to microbiological homogeneity, i.e. they grow as single colonies when streaked out on agar plates by methods known in the art. Preferably, the agar plates that are used for this purpose are selective for *Lactobacillus* species. Such selective agar plates are known in the art.

In another aspect the present invention relates to an inactivated form of the microorganism of the present invention, which is, e.g., thermally inactivated or lyophilized, but which retains the property of inhibiting the growth of one or more microorganisms of the transient pathogenic skin micro flora and of not inhibiting the growth of microorganisms of the healthy normal resident skin micro flora.

According to the present invention the term "inactivated form of the microorganism of the present invention" includes a dead or inactivated cell of the microorganism of the present invention, preferably of the *Lactobacillus* species disclosed herein, which is no longer capable to form a single colony on a plate specific for microorganisms belonging to the genus of *Lactobacillus*. Said dead or inactivated cell may have either an intact or broken cell membrane. Methods for killing or inactivating cells of the microorganism of the present invention are known in the art. El-Nezami et al., J. Food Prot. 61 (1998), 466-468 describes a method for inactivating *Lactobacillus* species by UV-irradiation. Preferably, the cells of the microorganism of the present invention are thermally inactivated or lyophilised. Lyophilisation of the cells of the present invention has the advantage that they can be easily stored and handled while retaining their property of inhibiting the growth of one or more microorganisms of the transient pathogenic skin micro flora and of not inhibiting the growth of microorganisms of the healthy normal resident skin micro flora. Moreover, lyophilised cells can be grown again when applied under conditions known in the art to appropriate liquid or solid media. Lyophilization is done by methods known in the art. Preferably, it is carried out for at least 2 hours at room temperature, i.e. any temperature between 16° C. and 25° C. Moreover, the lyophilized cells of the microorganism of the present invention are stable for at least 4 weeks at a temperature of 4° C. so as to still retain their properties as described above. Thermal inactivation can be achieved by incubating the cells of the microorganism of the present invention for at least 2 hours at a temperature of 170° C. Yet, thermal inactivation is preferably achieved by autoclaving said cells at a temperature of 121° C. for at least 20 minutes in the presence of satured steam at an atmospheric pressure of 2 bar. In the alternative, thermal inactivation of the cells of the microorganism of the present invention is achieved by freezing said cells for at least 4 weeks, 3 weeks, 2 weeks, 1 week, 12 hours, 6 hours, 2 hours or 1 hour at −20° C. It is preferred that at least 70%, 75% or 80%, more preferably 85%, 90% or 95% and particularly preferred at least 97%, 98%, 99% and more particularly preferred, 99.1%, 99.2%, 99.3%, 99.4%, 99.5%, 99.6%, 99.7%, 99.8% or 99.9% and most particularly preferred 100% of the cells of the inactivated form of the microorganism of the present invention are dead or inactivated, however, they have still the capability to inhibit the growth of one or more microorganisms of the transient pathogenic skin micro flora but do not inhibit the growth of microorganisms of the healthy normal resident skin micro flora. Whether the inactivated form of the microorganism of the present invention is indeed dead or inactivated can be tested by methods known in the art, for example, by a test for viability.

The term "inactivated form of the microorganism of the present invention" also encompasses lysates or fractions of the microorganism of the present invention, preferably of the *Lactobacillus* species disclosed herein, wherein said lysates or fractions preferably inhibit the growth of one or more microorganisms of the transient pathogenic skin micro flora, preferably of *Staphylococcus aureus* and do not inhibit the growth of microorganisms of the healthy normal resident skin micro flora. This inhibition can be tested as described herein and in particular as described in the appended Examples. In case, a lysate or fraction of the microorganism of the present invention may not inhibit or stimulate the growth of a microorganism of the transient pathogenic skin micro flora, then the skilled person can, for example, further purify said lysate or fraction by methods known in the art, which are exemplified herein below, so as to remove substances which may stimulate the growth of microorganisms of the transient pathogenic skin micro flora. Afterwards the person skilled in the art can again test said lysate or fraction whether it inhibits the growth of a microorganism of the transient pathogenic skin micro flora but not the growth of a microorganism of the resident skin micro flora.

According to the present invention the term "lysate" means a solution or suspension in an aqueous medium of cells of the microorganism of the present invention that are broken or an extract. However, the term should not be construed in any limiting way. The cell lysate comprises, e.g., macromolecules, like DNA, RNA, proteins, peptides, carbohydrates, lipids and the like and/or micromolecules, like amino acids, sugars, lipid acids and the like, or fractions of it. Additionally, said lysate comprises cell debris which may be of smooth or granular structure. Methods for preparing cell lysates of microorganism are known in the art, for example, by employing French press, cells mill using glass or iron beads or enzymatic cell lysis and the like. In addition, lysing cells relates to various methods known in the art for opening/destroying cells. The method for lysing a cell is not important and any method that can achieve lysis of the cells of the microorganism of the present invention may be employed. An appropriate one can be chosen by the person skilled in the art, e.g. opening/destruction of cells can be done enzymatically, chemically or physically. Non-limiting examples for enzymes and enzyme cocktails are proteases, like proteinase K, lipases or glycosidases; non-limiting examples for chemicals are ionophores, detergents, like sodium dodecyl sulfate, acids or bases; and non-limiting examples of physical means are high pressure, like French-pressing, osmolarity, temperature, like heat or cold. Additionally, a method employing an appropriate combination of an enzyme other than the proteolytic enzyme, an acid, a base and the like may also be utilized. For example, the cells of the microorganism of the present invention are lysed by freezing and thawing, more preferably freezing at temperatures below −70° C. and thawing at temperatures of more than 30° C., particularly freezing is preferred at temperatures below −75° C. and thawing is preferred at temperatures of more than 35° C. and most preferred are temperatures for freezing below −80° C. and temperatures for thawing of more than 37° C. It is also preferred that said freezing/thawing is repeated for at least 1 time, more preferably for at least 2 times, even more preferred for at least 3 times, particularly preferred for at least 4 times and most preferred for at least 5 times.

Accordingly, those skilled in the art can prepare the desired lysates by referring to the above general explanations, and appropriately modifying or altering those methods, if necessary. Preferably, the aqueous medium used for the lysates as described is water, physiological saline, or a buffer solution. An advantage of a bacterial cell lysate is that it can be easily produced and stored cost efficiently since less technical facilities are needed.

According to the invention, lysates are also preparations of fractions of molecules from the above-mentioned lysates.

These fractions can be obtained by methods known to those skilled in the art, e.g., chromatography, including, e.g., affinity chromatography, ion-exchange chromatography, size-exclusion chromatography, reversed phase-chromatography, and chromatography with other chromatographic material in column or batch methods, other fractionation methods, e.g., filtration methods, e.g., ultrafiltration, dialysis, dialysis and concentration with size-exclusion in centrifugation, centrifugation in density-gradients or step matrices, precipitation, e.g., affinity precipitations, salting-in or salting-out (ammoniumsulfate-precipitation), alcoholic precipitations or other proteinchemical, molecular biological, biochemical, immunological, chemical or physical methods to separate above components of the lysates. In a preferred embodiment those fractions which are more immunogenic than others are preferred. Those skilled in the art are able to choose a suitable method and determine its immunogenic potential by referring to the above general explanations and specific explanations in the examples herein, and appropriately modifying or altering those methods, if necessary.

Accordingly, the term "an inactive form of the microorganism of the present invention" also encompasses filtrates of the microorganism of the present invention, preferably of the *Lactobacillus* species disclosed herein, wherein said filtrates preferably inhibit the growth of one or more microorganisms of the transient pathogenic skin micro flora, preferably of *Staphylococcus aureus* and do not inhibit the growth of microorganisms of the healthy normal resident skin micro flora. This inhibition can be tested as described herein and in particular as described in the appended Examples. In case, a filtrate of the microorganism of the present invention may not inhibit or stimulate the growth of a microorganism of the transient pathogenic skin micro flora, then the skilled person can, for example, further purify said filtrate by methods known in the art, so as to remove substances which may stimulate the growth of microorganisms of the transient pathogenic skin micro flora. Afterwards the person skilled in the art can again test said filtrate whether it inhibits the growth of a microorganism of the transient pathogenic skin micro flora but not the growth of a microorganism of the resident skin micro flora.

The term "filtrate" means a cell-free solution or suspension of the microorganism of the present invention which has been obtained as supernatant of a centrifugation procedure of a culture of the microorganism of the present invention in any appropriate liquid, medium or buffer known to the person skilled in the art. However, the term should not be construed in any limiting way. The filtrate comprises, e.g., macromolecules, like DNA, RNA, proteins, peptides, carbohydrates, lipids and the like and/or micromolecules, like amino acids, sugars, lipid acids and the like, or fractions of it. Methods for preparing filtrates of microorganism are known in the art. In addition, "filtrate" relates to various methods known in the art. The exact method is not important and any method that can achieve filtration of the cells of the microorganism of the present invention may be employed.

The term "an inactive form of the microorganism of the present invention" encompasses any part of the cells of the microorganism of the present invention. Preferably, said inactive form is a membrane fraction obtained by a membrane-preparation. Membrane preparations of microorganisms belonging to the genus of *Lactobacillus* can be obtained by methods known in the art, for example, by employing the method described in Rollan et al., Int. J. Food Microbiol. 70 (2001), 303-307, Matsuduchi et al., Clin. Diagn. Lab. Immunol. 10 (2003), 259-266 or Stentz et al., Appl. Environ. Microbiol. 66 (2000), 4272-4278 or Varmanen et al., J. Bacteriology 182 (2000), 146-154. Alternatively, a whole cell preparation is also envisaged.

In another aspect the present invention relates to a composition comprising a microorganism according to the present invention or a mutant, derivative or inactive form of this microorganism as described above. In a preferred embodiment, said composition comprises a microorganism as described above in an amount between $10^2$ to $10^{12}$ cells, preferably $10^3$ to $10^8$ cells per mg in a solid form of the composition. In case of a liquid form of compositions, the amount of the microorganisms is between $10^2$ to $10^{13}$ cells per ml. In a further preferred embodiment said compositions are in the form of emulsions, e.g. oil in water or water in oil emulsions, in the form of ointments or in the form of micro-capsules. In case of emulsions, ointments or micro-capsules the compositions comprise a microorganism as described herein in an amount between $10^2$ to $10^{13}$ cells per ml. However, for specific compositions the amount of the microorganism may be different as is described herein.

In a still further aspect, the present invention provides a method for the production of a composition for protecting the skin against pathogenic microorganisms comprising the steps of formulating a microorganism according to the invention or a mutant, derivative or inactive form of this microorganism as described above with a cosmetically or pharmaceutical acceptable carrier or excipient.

The term "composition", as used in accordance with the present invention, relates to (a) composition(s) which comprise(s) at least one microorganism of the present invention or mutant, derivative or inactive form of said microorganism as described above. It is envisaged that the compositions of the present invention which are described herein below comprise the aforementioned ingredients in any combination. It may, optionally, comprise at least one further ingredient suitable for protecting the skin against pathogenic microorganisms. Accordingly, it may optionally comprise any combination of the hereinafter described further ingredients. The term "ingredients suitable for protecting the skin against pathogenic microorganisms" encompasses compounds or compositions and/or combinations thereof which lower the pH.

The composition may be in solid, liquid or gaseous form and may be, inter alia, in the form of (a) powder(s), (a) solution(s) (an) aerosol(s), suspensions, emulsions, liquids, elixirs, extracts, tincture or fluid extracts or in a form which is particularly suitable for topical administration. Forms suitable for topical application include, e.g., a paste, an ointment, a lotion, a cream, a gel or a transdermal patch.

Preferably, the composition of the present invention is a cosmetic composition further comprising a cosmetically acceptable carrier or excipient. More preferably, said cosmetic composition is a paste, an ointment, a lotion, a cream or a gel.

The cosmetic composition of the present invention comprises the microorganism of the present invention, mutant, derivative or inactive form thereof as described above in connection with the composition of the invention and further a cosmetically acceptable carrier. Preferably the cosmetic composition of the present invention is for use in topical applications.

The term "cosmetically acceptable carrier" as used herein means a suitable vehicle, which can be used to apply the present compositions to the skin in a safe and effective manner. Such vehicle may include materials such as emulsions, e.g. oil in water or water in oil emulsions, ointments or micro capsules. It is also advantageous to administer the active ingredients in encapsulated form, e.g. as cellulose encapsulation, in gelatine, with polyamides, niosomes, wax matrices, with cyclodextrins or liposomally encapsulated. The term "safe and effective amount" as used herein, means a sufficient amount to inhibit the growth of one or more microorganisms of the transient pathogenic skin micro flora.

In another aspect the present invention relates to a pharmaceutical composition comprising the microorganism of the present invention or a derivative or mutant or an inactive form thereof as described above further comprising a pharmaceutical acceptable carrier or excipient. The pharmaceutical composition preferably is in a form which is suitable for topical administration.

In addition, the present invention relates to the use of a microorganism of the present invention or of a derivative or mutant or an inactive form thereof as described above for the preparation of a composition, preferably a pharmaceutical or cosmetic composition.

Pharmaceutical compositions comprise a therapeutically effective amount of a microorganism of the present invention or of a derivative or mutant of the present invention or an inactive form of said microorganism of the present invention as described above and can be formulated in various forms, e.g. in solid, liquid, powder, aqueous, lyophilized form.

The pharmaceutical composition may be administered with a pharmaceutically acceptable carrier to a patient, as described herein. In a specific embodiment, the term "pharmaceutically acceptable" means approved by a regulatory agency or other generally recognized pharmacopoeia for use in animals, and more particularly in humans.

The term "carrier" refers to a diluent, adjuvant, excipient, or vehicle with which the therapeutic is administered. Such a carrier is pharmaceutically acceptable, i.e. is non-toxic to a recipient at the dosage and concentration employed. It is preferably isotonic, hypotonic or weakly hypertonic and has a relatively low ionic strength, such as provided by a sucrose solution. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers. Suitable pharmaceutical excipients include starch, glucose, sucrose, gelatin, malt, rice, flour, chalk, silica gel, sodium stearate, glycerol monostearate, talc, sodium ion, dried skim milk, glycerol, propylene, glycol, water, ethanol and the like. The composition, if desired, can also contain minor amounts of wetting or emulsifying agents, or pH buffering agents. These compositions can take the form of, e.g., solutions, suspensions, emulsion, powders, sustained-release formulations and the like. Examples of suitable pharmaceutical carriers are described in "Remington's Pharmaceutical Sciences" by E. W. Martin. Some other examples of substances which can serve as pharmaceutical carriers are sugars, such as glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; calcium carbonate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; cranberry extracts and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tabletting agents, stabilizers, anti-oxidants and preservatives, can also be present. It is also advantageous to administer the active ingredients in encapsulated form, e.g. as cellulose encapsulation, in gelatine, with polyamides, niosomes, wax matrices, with cyclodextrins or liposomally encapsulated.

Generally, the ingredients are supplied either separately or mixed together in unit dosage form, for example, as a dry lyophilised powder or water free concentrate in a hermetically sealed container such as an ampoule or sachette indicating the quantity of active agent.

The pharmaceutical composition of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In vitro or in situ assays, e.g. those described in the Examples, may optionally be employed to help identify optimal dosage ranges. The precise dose to be employed in the formulation will also depend on the route of administration, and the seriousness of the disease or disorder, and should be decided according to the judgment of the practitioner and each patient's circumstances. The topical route of administration is preferred. Effective doses may be extrapolated from dose-response curves derived from in vitro or (animal) model test systems. Preferably, the pharmaceutical composition is administered directly or in combination with an adjuvant. Adjuvants may be selected from the group consisting of a chloroquine, protic polar compounds, such as propylene glycol, polyethylene glycol, glycerol, EtOH, 1-methyl L-2-pyrrolidone or their derivatives, or aprotic polar compounds such as dimethylsulfoxide (DMSO), diethylsulfoxide, di-n-propylsulfoxide, dimethylsulfone, sulfolane, dimethylformamide, dimethylacetamide, tetramethylurea, acetonitrile or their derivatives. These compounds are added in conditions respecting pH limitations. The composition of the present invention can be administered to a vertebrate. "Vertebrate" as used herein is intended to have the same meaning as commonly understood by one of ordinary skill in the art. Particularly, "vertebrate" encompasses mammals, and more particularly humans.

The term "administered" means administration of a therapeutically effective dose of the aforementioned composition. By "therapeutically effective amount" is meant a dose that produces the effects for which it is administered, preferably this effect is the protection of skin against pathogenic microorganisms. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

The methods are applicable to both human therapy and veterinary applications. The compounds described herein having the desired therapeutic activity may be administered in a physiologically acceptable carrier to a patient, as described herein. Depending upon the manner of administration, the compounds may be formulated in a variety of ways as discussed below. The concentration of the therapeutically active compound in the formulation may vary from about 0.01-100 wt %. The agent may be administered alone or in combination with other treatments.

The administration of the pharmaceutical composition can be done in a variety of ways. The preferable route of administering is the topical route.

The attending physician and clinical factors will determine the dosage regimen. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg; however, doses below or above this exemplary range are envisioned, especially considering the aforementioned factors.

The dosages are preferably given once a week, more preferably 2 times, 3 times, 4 times, 5 times or 6 times a week and most preferably daily and even more preferably, 2 times a day or more often. In particular, it may be preferable to give a dosage each time after a disturbance of the resident skin flora occurred, e.g. by washing. However, during progression of the treatment the dosages can be given in much longer time intervals and in need can be given in much shorter time intervals, e.g., several times a day. In a preferred case the immune response is monitored using herein described methods and further methods known to those skilled in the art and dosages are optimized, e.g., in time, amount and/or composition. Progress can be monitored by periodic assessment. It is also envisaged that the pharmaceutical compositions are employed in co-therapy approaches, i.e. in co-administration with other medicaments or drugs, for example other drugs for protecting skin against pathogenic microorganisms.

Topical administration of the cosmetic or pharmaceutical composition of the present invention is useful when the desired treatment involves areas or organs readily accessible by topical administration. For application topically to the skin, the pharmaceutical composition is preferably formulated with a suitable paste, ointment, lotion, cream, gel or transdermal patches. The cosmetic or pharmaceutical preparations can, depending on the field of use, also be in the form of a spray (pump spray or aerosol), foam, gel spray, mousse, suspensions or powders.

A suitable paste comprises the active ingredient suspended in a carrier. Such carriers include, but are not limited to, petroleum, soft white paraffin, yellow petroleum jelly and glycerol.

The cosmetic or pharmaceutical composition may also be formulated with a suitable ointment comprising the active components suspended or dissolved in a carrier. Such carriers include, but are not limited to, one or more of glycerol, mineral oil, liquid oil, liquid petroleum, white petroleum, yellow petroleum jelly, propylene glycol, alcohols, triglycerides, fatty acid esters such as cetyl ester, polyoxyethylene polyoxypropylene compound, waxes such as white wax and yellow beeswax, fatty acid alcohols such as cetyl alcohol, stearyl alcohol and cetylstearylalcohol, fatty acids such as stearic acid, cetyl stearate, lanolin, magnesium hydroxide, kaolin and water.

Alternatively, the cosmetic or pharmaceutical composition may also be formulated with a suitable lotion or cream comprising the active components suspended or dissolved in a carrier. Such carriers include, but are not limited to, one or more of mineral oil such as paraffin, vegetable oils such as castor oil, castor seed oil and hydrogenated castor oil, sorbitan monostearat, polysorbat, fatty acid esters such as cetyl ester, wax, fatty acid alcohols such as cetyl alcohol, stearyl alcohol, 2-octyldodecanol, benzyl alcohol, alcohols, triglycerides and water.

Alternatively, the cosmetic or pharmaceutical composition may also be formulated with a suitable gel comprising the active components suspended or dissolved in a carrier. Such carriers include, but are not limited to, one or more of water, glycerol, propyleneglycole, liquid paraffin, polyethylene, fatty oils, cellulose derivatives, bentonite and colloidal silicon dioxide.

Suitable propellants for aerosols according to the invention are the customary propellants, for example propane, butane, pentane and others.

The preparations according to the invention may generally comprise further auxiliaries as are customarily used in such preparations, e.g. preservatives, perfumes, antifoams, dyes, pigments, thickeners, surface-active substances, emulsifiers, emollients, finishing agents, fats, oils, waxes or other customary constituents, of a cosmetic or dermatological formulation, such as alcohols, polyols, polymers, foam stabilizers, solubility promoters, electrolytes, organic acids, organic solvents, or silicone derivatives.

The cosmetic or pharmaceutical composition according to the invention may comprise emollients. Emollients may be used in amounts which are effective to prevent or relieve dryness. Useful emollients include, without limitation: hydrocarbon oils and waxes; silicone oils; triglyceride esters; acetoglyceride esters; ethoxylated glyceride; alkyl esters; alkenyl esters; fatty acids; fatty alcohols; fatty alcohol ethers; etheresters; lanolin and derivatives; polyhydric alcohols (polyols) and polyether derivatives; polyhydric alcohol (polyol) esters; wax esters; beeswax derivatives; vegetable waxes; phospholipids; sterols; and amides.

Thus, for example, typical emollients include mineral oil, especially mineral oils having a viscosity in the range of 50 to 500 SUS, lanolin oil, mink oil, coconut oil, cocoa butter, olive oil, almond oil, macadamia nut oil, aloa extract, jojoba oil, safflower oil, corn oil, liquid lanolin, cottonseed oil, peanut oil, purcellin oil, perhydrosqualene (squalene), caster oil, polybutene, odorless mineral spirits, sweet almond oil, avocado oil, calophyllum oil, ricin oil, vitamin E acetate, olive oil, mineral spirits, cetearyl alcohol (mixture of fatty alcohols consisting predominantly of cetyl and stearyl alcohols), linolenic alcohol, oleyl alcohol, octyl dodecanol, the oil of cereal germs such as the oil of wheat germ cetearyl octanoate (ester of cetearyl alcohol and 2-ethylhexanoic acid), cetyl palmitate, diisopropyl adipate, isopropyl palmitate, octyl palmitate, isopropyl myristate, butyl myristate, glyceryl stearate, hexadecyl stearate, isocetyl stearate, octyl stearate, octylhydroxy stearate, propylene glycol stearate, butyl stearate, decyl oleate, glyceryl oleate, acetyl glycerides, the octanoates and benzoates of (C12-C15) alcohols, the octanoates and decanoates of alcohols and polyalcohols such as those of glycol and glycerol, and ricin-oleates of alcohols and poly alcohols such as those of isopropyl adipate, hexyl laurate, octyl dodecanoate, dimethicone copolyol, dimethiconol, lanolin, lanolin alcohol, lanolin wax, hydrogenated lanolin, hydroxylated lanolin, acetylated lanolin, petrolatum, isopropyl lanolate, cetyl myristate, glyceryl myristate, myristyl myristate, myristyl lactate, cetyl alcohol, isostearyl alcohol stearyl alcohol, and isocetyl lanolate, and the like.

Moreover, the cosmetic or pharmaceutical composition according to the invention may also comprise emulsifiers. Emulsifiers (i.e., emulsifying agents) are preferably used in amounts effective to provide uniform blending of ingredients of the composition. Useful emulsifiers include (i) anionics such as fatty acid soaps, e.g., potassium stearate, sodium stearate, ammonium stearate, and triethanolamine stearate; polyol fatty acid monoesters containing fatty acid soaps, e.g., glycerol monostearate containing either potassium or sodium salt; sulfuric esters (sodium salts), e.g., sodium lauryl 5 sulfate, and sodium cetyl sulfate; and polyol fatty acid monoesters containing sulfuric esters, e.g., glyceryl monostearate containing sodium lauryl sulfate; (ii) cationics chloride such as N(stearoyl colamino formylmethyl) pyridium; N-soya-N-ethyl morpholinium ethosulfate; alkyl dimethyl benzyl ammonium chloride; diisobutylphenoxytheoxyethyl dimethyl benzyl ammonium chloride; and cetyl pyridium chloride; and (iii) nonionics such as polyoxyethylene fatty alcohol ethers, e.g., monostearate; polyoxyethylene lauryl alcohol; polyoxypropylene fatty alcohol ethers, e.g., propoxylated oleyl alcohol; polyoxyethylene fatty acid esters, e.g., polyoxyethylene stearate; polyoxyethylene sorbitan fatty acid esters, e.g., polyoxyethylene sorbitan monostearate; sorbitan fatty acid esters, e.g., sorbitan; polyoxyethylene glycol fatty acid esters, e.g., polyoxyethylene glycol monostearate, and polyol fatty acid esters, e.g., glyceryl monostearate and propylene glycol monostearate; and ethoxylated lanolin derivatives, e.g., ethoxylated lanolins, ethoxylated lanolin alcohols and ethoxylated cholesterol. The selection of emulsifiers is exemplarly described in Schrader, Grundlagen and Rezepturen der Kosmetika, Huthig Buch Verlag, Heidelberg, $2^{nd}$ edition, 1989, $3^{rd}$ part.

The cosmetic or pharmaceutical composition according to the invention may also include a surfactant. Suitable surfactants may include, for example, those surfactants generally grouped as cleansing agents, emulsifying agents, foam boosters, hydrotropes, solubilizing agents, suspending agents and nonsurfactants (facilitates the dispersion of solids in liquids).

The surfactants are usually classified as amphoteric, anionic, cationic and nonionic surfactants. Amphoteric surfactants include acylamino acids and derivatives and N-alkylamino acids. Anionic surfactants include: acylamino acids and salts, such as, acylglutamates, acylpeptides, acylsarcosinates, and acyltaurates, carboxylic acids and salts, such as, alkanoic acids, ester carboxylic acids, and ether carboxylic acids; sulfonic acids and salts, such as, acyl isethionates, alkylaryl sulfonates, alkyl sulfonates, and sulfosuccinates; sulfuric acid esters, such as, alkyl ether sulfates and alkyl sulfates. Cationic surfactants include: alkylamines, alkyl imidazolines, ethoxylated amines, and quaternaries (such as, alkylbenzyldimethylammonium salts, alkyl betaines, heterocyclic ammonium salts, and tetra alkylammonium salts). And nonionic surfactants include: alcohols, such as primary alcohols containing 8 to 18 carbon atoms; alkanolamides such as alkanolamine derived amides and ethoxylated amides; amine oxides; esters such as ethoxylated carboxylic acids, ethoxylated glycerides, glycol esters and derivatives, monoglycerides, polyglyceryl esters, polyhydric alcohol esters and ethers, sorbitan/sorbitol esters, and triesters of phosphoric acid; and ethers such as ethoxylated alcohols, ethoxylated lanolin, ethoxylated polysiloxanes, and propoxylated polyoxyethylene ethers.

Furthermore, a cosmetic or pharmaceutical composition according to the invention may also comprise a film former. Suitable film formers which are used in accord with the invention keep the composition smooth and even and include, without limitation: acrylamide/sodium acrylate copolymer; ammonium acrylates copolymer; Balsam Peru; cellulose gum; ethylene/maleic anhydride copolymer; hydroxyethylcellulose; hydroxypropylcellulose; polyacrylamide; polyethylene; polyvinyl alcohol; pvm/MA copolymer (polyvinyl methylether/maleic anhydride); PVP (polyvinylpyrrolidone); maleic anhydride copolymer such as PA-18 available from Gulf Science and Technology; PVP/hexadecene copolymer such as Ganex V-216 available from GAF Corporation; acryliclacrylate copolymer; and the like.

Generally, film formers can be used in amounts of about 0.1% to about 10% by weight of the total composition with about 1% to about 8% being preferred and about 0.1 DEG/O to about 5% being most preferred. Humectants can also be used in effective amounts, including: fructose; glucose; glulamic acid; glycerin; honey; maltitol; methyl gluceth-10, methyl gluceth-20; propylene glycol; sodium lactate; sucrose; and the like.

Of course, the cosmetic or pharmaceutical composition of the present invention can also comprise a preservative. Preservatives according to certain compositions of the invention include, without limitation: butylparaben; ethylparaben; imidazolidinyl urea; methylparaben; O-phenylphenol; propylparaben; quaternium-14; quaternium-15; sodium dehydroacetate; zinc pyrithione; and the like.

The preservatives are used in amounts effective to prevent or retard microbial growth. Generally, the preservatives are used in amounts of about 0.1% to about 1% by weight of the total composition with about 0.1% to about 0.8% being preferred and about 0.1% to about 0.5% being most preferred.

A cosmetic or pharmaceutical composition according to the invention may also comprise a perfume. Perfumes (fragrance components) and colorants (coloring agents) well known to those skilled in the art may be used in effective amounts to impart the desired fragrance and color to the compositions of the invention.

Furthermore, a cosmetic or pharmaceutical composition of the present invention may also comprise a wax. Suitable waxes which are useful in accord with the invention include: animal waxes, such as beeswax, spermaceti, or wool wax (lanolin); plant waxes, such as carnauba or candelilla; mineral waxes, such as montan wax or ozokerite; and petroleum waxes, such as paraffin wax and microcrystalline wax (a high molecular weight petroleum wax). Animal, plant, and some mineral waxes are primarily esters of a high molecular weight fatty alcohol with a high molecular weight fatty acid. For example, the hexadecanoic acid ester of tricontanol is commonly reported to be a major component of beeswax. Other suitable waxes according to the invention include the synthetic waxes including polyethylene polyoxyethylene and hydrocarbon waxes derived from carbon monoxide and hydrogen.

Representative waxes also include: cerosin; cetyl esters; hydrogenated joioba oil; hydrogenated jojoba wax; hydrogenated rice bran wax; Japan wax; jojoba butter; jojoba oil; jojoba wax; munk wax; montan acid wax; ouricury wax; rice bran wax; shellac wax; sufurized jojoba oil; synthetic beeswax; synthetic jojoba oils; trihydroxystearin; cetyl alcohol; stearyl alcohol; cocoa butter; fatty acids of lanolin; mono-, di- and 25 triglycerides which are solid at 25 DEG C., e.g., glyceyl tribehenate (a triester of behenic acid and glycerine) and C1g-C36 acid triglyceride (a mixture of triesters of C1g-C36 carboxylic acids and glycerine) available from Croda, Inc., New York, N.Y. under the tradenames Syncrowax HRC and Syncrowax HGL-C, respectively; fatty esters which are solid at 25 DEG C.; silicone waxes such as methyloctadecaneoxypolysiloxane and poly (dimethylsiloxy) stearoxysiloxane; stearyl mono- and diethanolamide; rosin and its derivatives such as the abietates of glycol and glycerol; hydrogenated oils solid at 25 DEG C.; and sucroglycerides. Thickeners (viscosity control agents) which may be used in effective amounts in aqueous systems include: algin; carbomers such as carbomer 934, 934P, 940 and 941; cellulose gum; cetearyl alcohol, cocamide DEA, dextrin; gelatin; hydroxyethylcellulose; hydroxypropylcellulose; hydroxypropyl methylcellulose; magnesium aluminum silicate; myristyl alcohol; oat flour; oleamide DEA; oleyl alcohol; PEG-7M; PEG-14M; PEG-90M; stearamide DEA; stearamide MEA; stearyl alcohol; tragacanth gum; wheat starch; xanthan gum; and the likein the above list of thickeners, DEA is diethanolamine, and MEA is monoethanolamine. Thickeners (viscosity control agents) which may be used in effective amounts in nonaqueous systems include aluminum stearates; beeswax; candelilla wax; carnauba; ceresin; cetearyl alcohol; cetyl alcohol; cholesterol; hydrated silica; hydrogenated castor oil; hydrogenated cottonseed oil; hydrogenated soybean oil; hydrogenated tallow glyceride; hydrogenated vegetable oil; hydroxypropyl cellulose; lanolin alcohol; myristyl alcohol; octytdodecyl stearoyl sulfate; oleyl alcohol; ozokerite; microcystalline wax; paraffin, pentaerythrityl tetraoctanoate; polyacrylamide; polybutene; polyethylene; propylene glycol dicaprylate; propylene glycol dipelargonate; stearalkonium hectorite; stearyl alcohol; stearyl stearate; synthetic beeswax; trihydroxystearin; trilinolein; tristearin; zinc stearate; and the like.

Customary native and synthetic thickeners or gel formers in formulations are crosslinked polyacrylic acids and derivatives thereof, polysaccharides, such as xanthane gum or alginates, carboxymethylcellulose or hydroxycarboxymethylcellulose, hydrocolloids such as gum Arabic or montmorillonite minerals, such as bentonites or fatty alcohols, polyvinyl alcohol and polyvinlypyrrolidone.

Other ingredients which can be added or used in a cosmetic or pharmaceutical composition according to the invention in amounts effective for their intended use, include: biological additives to enhance performance or consumer appeal such as amino acids, proteins, vanilla, aloe extract, bioflavinoids, and the like; buffering agents, chelating agents such as EDTA; emulsion stabilizers; pH adjusters; opacifying agents; and propellants such as butane carbon clioxide, ethane, hydrochlorofluorocarbons 22 and 142b, hydrofluorocarbon 152a, isobutane, isopentane, nitrogen, nitrous oxide, pentane, propane, and the like.

Furthermore, the preparations according to the invention may also comprise compounds which have an antioxidative, free-radical scavenger, skin moisturizing or moisture-retaining, antierythematous, antiinflammatory or antiallergic action, in order to supplement or enhance their action. In particular, these compounds can be chosen from the group of vitamins, plant extracts, alpha- and beta-hydroxy acids, ceramides, antiinflammatory, antimicrobial or UV-filtering substances, and derivatives thereof and mixtures thereof. Advantageously, preparations according to the invention can also comprise substances which absorb UV radiation in the UV-B and/or UV-A region. The lipid phase is advantageously chosen from the group of substances of mineral oils, mineral waxes, branched and/or unbranched hydrocarbons and hydrocarbon waxes, triglycerides of saturated and/or unsaturated, branched and/or unbranched $C_8$-$C_{24}$-alkanecarboxylic acids; they can be chosen from synthetic, semisynthetic or natural oils, such as olive oil, palm oil, almond oil or mixtures; oils, fats or waxes, esters of saturated and/or unsaturated, branched and/or unbranched $C_3$-$C_{30}$-alkane carboxylic acids and saturated and/or unsaturated, branched and/or unbranched $C_3$-$C_{30}$-alcohols, from aromatic carboxylic acids and saturated and/or unsaturated, branched and/or unbranched $C_3$-$C_{30}$-alcohols, for example isopropyl myristate, isopropyl stearate, hexyldecyl stearate, oleyl oleate; and also synthetic, semisynthetic and natural mixtures of such esters, such as jojoba oil, alkyl benzoates or silicone oils, such as, for example, cyclomethicone, dimethylpolysiloxane, diethylpolysiloxane, octamethylcyclo-tetrasiloxane and mixtures thereof or dialkyl ethers.

The active ingredients according to the invention may, for example, be used in cosmetic compositions for the cleansing of the skin, such as bar soaps, toilet soaps, curd soaps, transparent soaps, luxury soaps, deodorizing soaps, cream soaps, baby soaps, skin protection soaps, abrasive soaps, syndets, liquid soaps, pasty soaps, soft soaps, washing pastes, liquid washing, showering and bath preparations, e.g. washing lotions, shower preparations, shower gels, foam baths, cream foam baths, oil baths, bath extracts, scrub preparations, in-situ products, shaving foams, shaving lotions, shaving creams. In addition, they are suitable for skin cosmetic preparations, such as W/O or O/W skin and body creams, day and night creams, light protection compositions, aftersun products, hand care products, face creams, multiple emulsions, gelees, microemulsions, liposome preparations, niosome preparations, antiwrinkle creams, face oils, lipogels, sportgels, moisturizing creams, bleaching creams, vitamin creams, skin lotions, care lotions, ampoules, aftershave lotions, preshaves, humectant lotions, tanning lotions, cellulite creams, depigmentation compositions, massage preparations, body powders, face tonics, deodorants, antiperspirants, nose strips, antiacne compositions, repellents and others.

In a preferred embodiment, a cosmetic composition comprises a daily care O/W formulation, which may contain, for example, the following ingredients in % in accordance with the International Nomenclature of Cosmetic Ingredients, INCI:

A
  1.7 ceteareth-6, stearyl alcohol
  0.7 ceteareth-25
  2.0 diethylamino hydroxybenzoyl hexyl benzoate
  2.0 PEG-14 dimethicone
  3.6 cetearyl alcohol
  6.0 ethylhexyl methoxycinnamate
  2.0 dibutyl adipate
B
  5.0 glycerol
  0.2 disodium EDTA
  1.0 panthenol
  q.s. preservative
  67.8 aqua dem.
C
  4.0 caprylic/capric triglyceride, sodium acrylates copolymer
D
  0.2 sodium ascorbyl phosphate
  1.0 tocopheryl acetate
  0.2 bisabolol
  1.0 caprylic/capric triglyceride, sodium ascorbate, tocopherol, retinol
  1.0 *Lactobacillus* spec.
E
  q.s. sodium hydroxide Phases A and B are separately heated to app. 80° C. Phase B is subsequently stirred into phase A and homogenized. Phase C is stirred into a combination of phases A and B and homogenized. The mixture is under agitation cooled down to app. 40° C.; then phase D is added and the pH is adjusted with phase E to approx. 6.5. The solution is subsequently homogenized and cooled down to room temperature.

In a further preferred embodiment, a cosmetic composition comprises a protecting day cream O/W formulation, which may contain, for example, the following ingredients in % in accordance with the International Nomenclature of Cosmetic Ingredients, INCI:

A
- 1.7 ceteareth-6, stearyl alcohol
- 0.7 ceteareth-25
- 2.0 diethylamino hydroxybenzoyl hexyl benzoate
- 2.0 PEG-14 dimethicone
- 3.6 cetearyl alcohol
- 6.0 ethyl hexyl methoxycinnamate
- 2.0 dibutyl adipate B
- 5.0 glycerol
- 0.2 disodium EDTA
- 1.0 panthenol
- q.s. preservative
- 68.6 aqua dem.

C
- 4.0 caprylic/capric triglyceride, sodium acrylates copolymer

D
- 1.0 sodium ascorbyl phosphate
- 1.0 tocopheryl acetate
- 0.2 bisabolol
- 1.0 *Lactobacillus* spec.

E
- q.s. sodium hydroxide

Phases A and B are separately heated to app. 80° C. Phase B is subsequently stirred into phase A and homogenized. Phase C is introduced into a combination of phases A and B and homogenized. The mixture is under agitation cooled down to app. 40° C.; then phase D is added and the pH is adjusted with phase E to about 6.5. The solution is subsequently homogenized and cooled down to room temperature.

In a further preferred embodiment, a cosmetic composition comprises a skin cleanser O/W formulation, which may contain, for example, the following ingredients in % in accordance with the International Nomenclature of Cosmetic Ingredients, INCI:

A
- 10.0 cetearyl ethylhexanoate
- 10.0 caprylic/capric triglyceride
- 1.5 cyclopentasiloxane, cyclohexasilosane
- 2.0 PEG-40 hydrogenated castor oil B
- 3.5 caprylic/capric triglyceride, sodium acrylates copolymer C
- 1.0 tocopheryl acetate
- 0.2 bisabolol
- q.s. preservative
- q.s. perfume oil D
- 3.0 polyquaternium-44
- 0.5 cocotrimonium methosulfate
- 0.5 ceteareth-25
- 2.0 panthenol, propylene glycol
- 4.0 propylene glycol
- 0.1 disodium EDTA
- 1.0 *Lactobacillus* spec.
- 60.7 aqua dem.

Initially, phase A is dissolved and phase B subsequently stirred into phase A. Subsequently, phase C is introduced into the combination of phases A and B. In a next step, phase D is dissolved and stirred into combined phases A, B and C. The mixture is homogenized and stirred for 15 min.

In a further preferred embodiment, a cosmetic composition comprises a daily care body spray formulation, which may contain, for example, the following ingredients in % in accordance with the International Nomenclature of Cosmetic Ingredients, INCI:

A
- 3.0 ethylhexyl methoxycinnamate
- 2.0 diethylamino hydroxybenzoyl hexyl benzoate
- 1.0 polyquaternium-44
- 3.0 propylene glycol
- 2.0 panthenol, propylene glycol
- 1.0 cyclopentasiloxane, cyclohexasiloxane
- 10.0 octyldodecanol
- 0.5 PVP
- 10.0 caprylic/capric triglyceride
- 3.0 C12-15 alkyl benzoate
- 3.0 glycerol
- 1.0 tocopheryl acetate
- 0.3 bisabolol
- 1.0 *Lactobacillus* spec.
- 59.2 alcohol The components of phase A are weighed out and dissolved until clearness.

In a further preferred embodiment, a cosmetic composition comprises a skin gel, which may contain, for example, the following ingredients in % in accordance with the International Nomenclature of Cosmetic Ingredients, INCI:
- 3.6 PEG-40 hydrogenated castor oil
- 15.0 alcohol
- 0.1 bisabolol
- 0.5 tocopheryl acetate
- q.s. perfume oil B
- 3.0 panthenol
- 0.6 carbomer
- 1.0 *Lactobacillus* spec.
- 75.4 aqua dem, C
- 0.8 triethanolamine Initially, phase A is dissolved until clearness. Phase B is macerated and subsequently neutralized with phase C. In a next step, phase A is stirred into the homogenized phase B and the mixture is homogenized.

In yet a further preferred embodiment, a cosmetic composition comprises an after shave lotion, which may contain, for example, the following ingredients in % in accordance with the International Nomenclature of Cosmetic Ingredients, INCI:

A
- 10.0 cetearyl ethylhexanoate
- 5.0 tocopheryl acetate
- 1.0 bisabolol
- 0.1 perfume oil
- 0.3 acrylates/c10-30 alkyl acrylate crosspolymer B
- 15.0 alcohol
- 1.0 panthenol
- 3.0 glycerol
- 1.0 *Lactobacillus* spec.
- 0.1 triethanolamine
- 63.5 aqua dem.

The component of phase A are mixed. In a next step, phase B is dissolved and introduced into phase A and subsequently homogenized.

The present invention also relates to the use of a microorganism according to the invention or of a derivative, mutant or inactive form thereof as described herein above for the preparation of a pharmaceutical composition for preventing or treating dermatitis, preferably atopic dermatitis, psoriasis, poison-ivy dermatitis, eczema herpeticum, kerion or scabies.

In another aspect the present invention relates to a method for the production of a composition comprising the step of formulating a microorganism of the invention or a derivative or mutant thereof or an inactive form as described herein above with a cosmetically and/or pharmaceutically carrier or excipient.

The present invention furthermore relates to a method of preventing or treating dermatitis, preferably atopic dermatitis, psoriasis, poison-ivy dermatitis, eczema herpeticum, kerion or scabies comprising the step of administering to a patient in need thereof a prophylactically or therapeutically effective amount of a composition according to the invention.

It is to be understood that this invention is not limited to the particular methodology, protocols, bacteria, vectors, and reagents etc. described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nadel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

It must be noted that as used herein and in the appended claims, the singular forms "a", "an", and "the", include plural referents unless the context clearly indicates otherwise. Thus, for example, reference to "a reagent" includes one or more of such different reagents, and reference to "the method" includes reference to equivalent steps and methods known to those of ordinary skill in the art that could be modified or substituted for the methods described herein.

Figure 5:
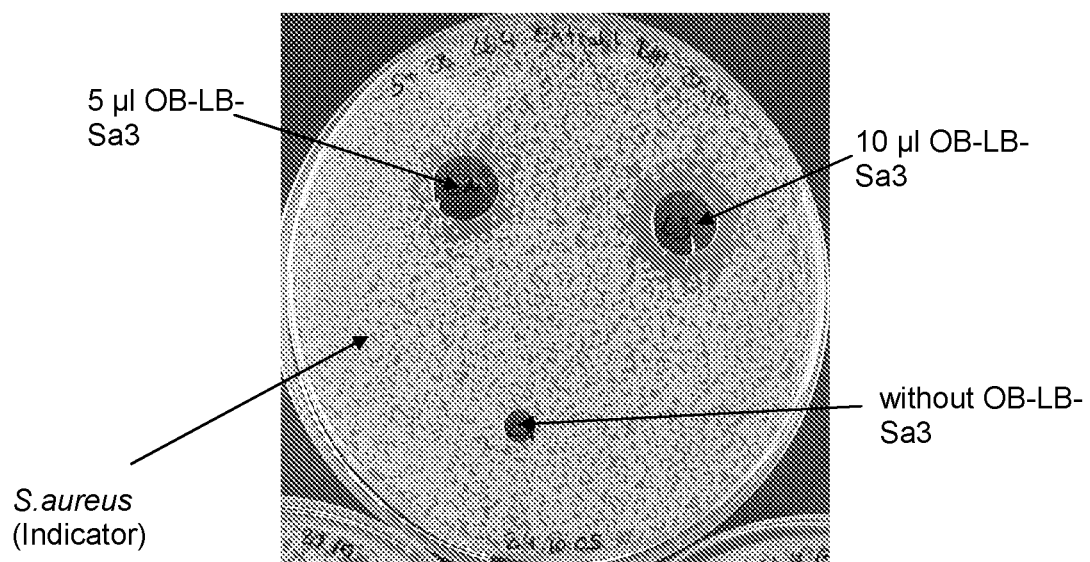

The second aspect of the invention is illustrated by FIGS. 5 to 11 as described in the following:

FIG. 5 shows the growth inhibition of *Staphylococcus aureus* in an in vitro hole/well plate assay (Example 5). The formation of a clear ring around the well indicates growth inhibition of the indicator strain *Staphylococcus aureus*.

Figure 6:
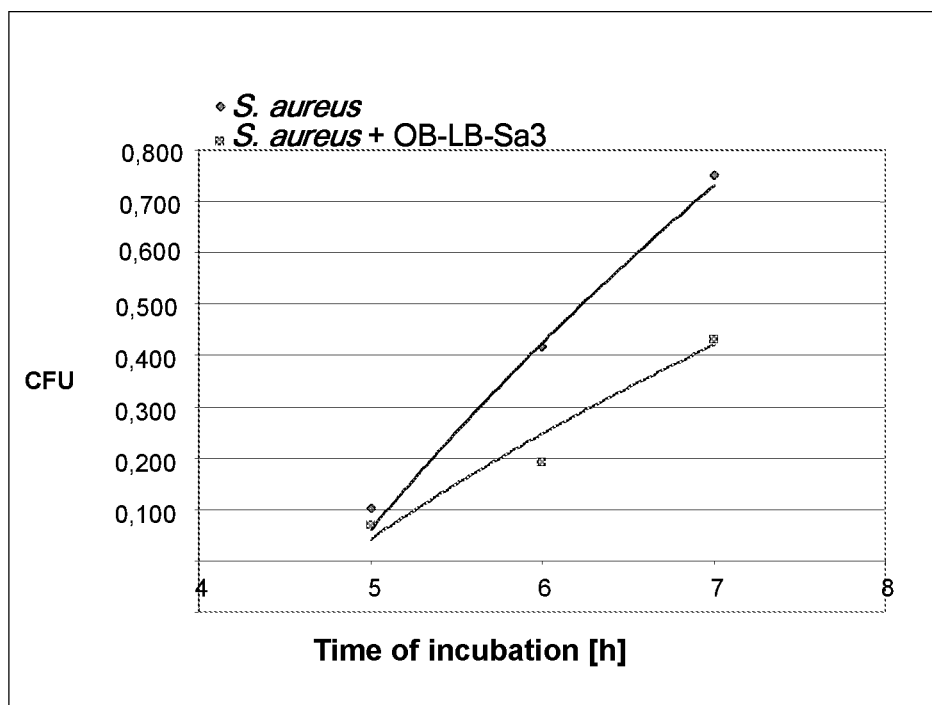

FIG. 6 shows growth inhibition of *Staphylococcus aureus* in an in vitro liquid assay (Example 6). Shown is the degree of inhibition which was quantified by counting the colony forming units of the indicator strain *Staphylococcus aureus* in comparison to a control without lactic acid bacteria.

Figure 7:
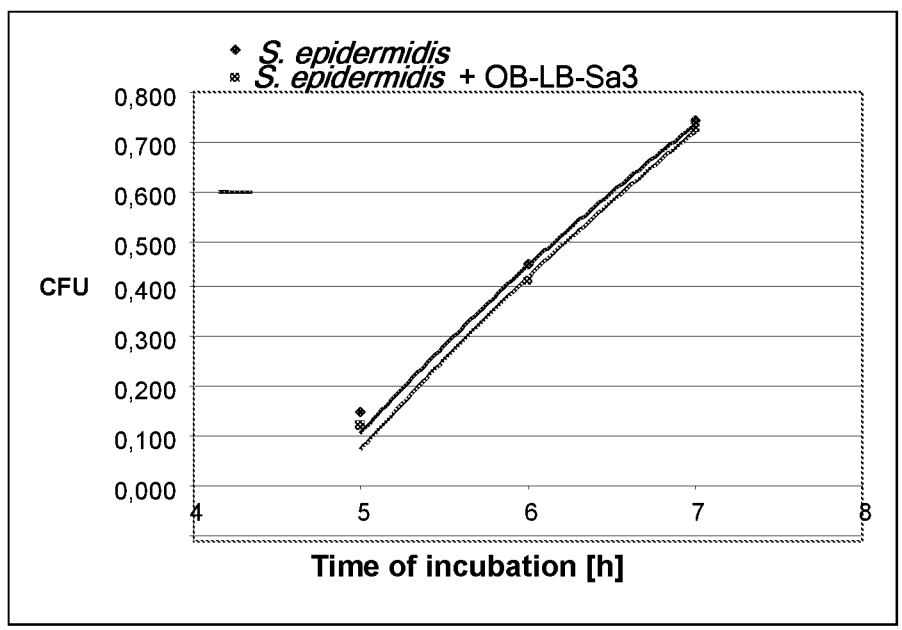

FIG. 7 shows the lack of growth inhibition of *Staphylococcus epidermidis* in an in vitro liquid assay (Example 7). Shown is the degree of inhibition which was quantified by counting the colony forming units of the indicator strain *Staphylococcus epidermidis* in comparison to a control without lactic acid bacteria.

Figure 8:
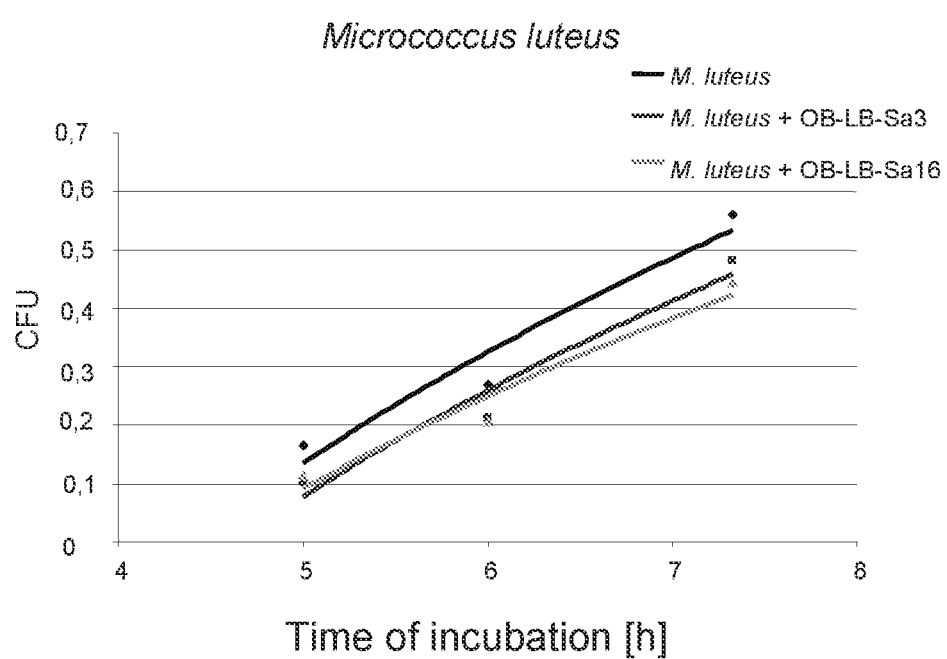

FIG. 8 shows the lack of growth inhibition of *Micrococcus luteus* in an in an in vitro liquid assay (Example 10). Shown is the degree of inhibition which was quantified by counting the colony forming units of the indicator strain *Micrococcus luteus* in comparison to a control without lactic acid bacteria.

Figure 9:
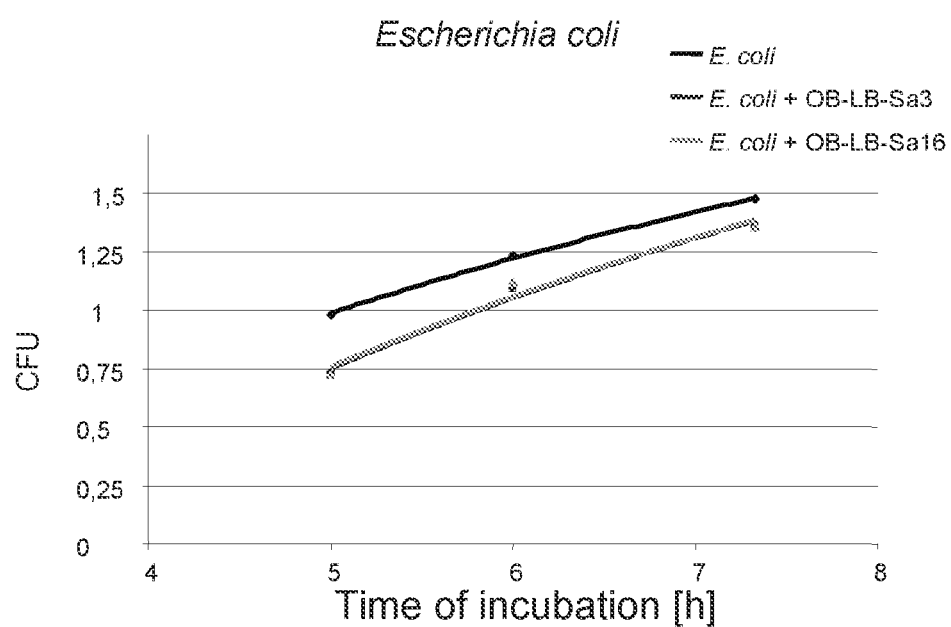

FIG. 9 shows the lack of growth inhibition of *Escherichia coli* in an in an in vitro liquid assay (Example 11). Shown is the degree of inhibition which was quantified by counting the colony forming units of the indicator strain *Escherichia coli* in comparison to a control without lactic acid bacteria.

Figure 11:
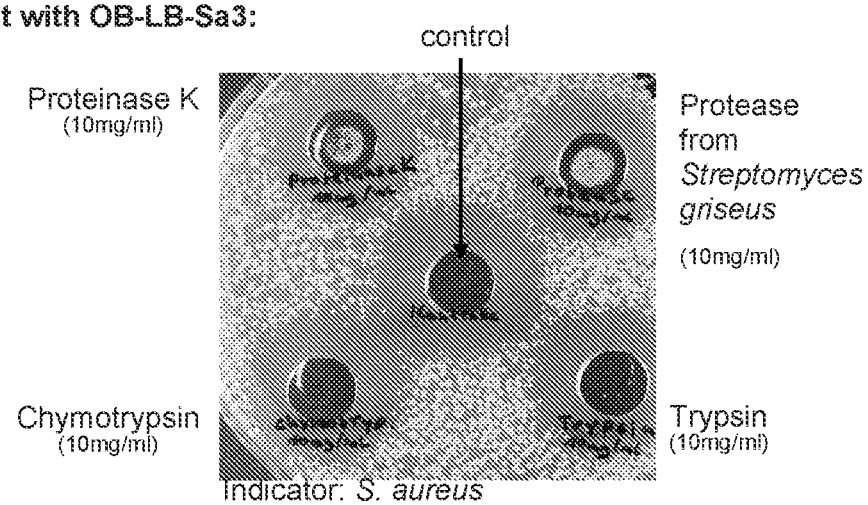

FIG. 10 shows the degree of growth inhibition of *Staphylococcus aureus* in an in vitro hole plate assay in comparison to bacitracin and erythromycin (Example 12). Bacitracin and erythromycin have been filled in precutted holes at different concentrations and the growth of *Staphylococcus aureus* has been observed. The corresponding calibration curves are shown in FIG. 10A. The growth inhibition of *S. aureus* by a defined number of precultured *Lactobacillus* cells (DSM 18006) is shown in FIG. 10B FIG. 11 shows the protease stability of *Lactobacillus* inhibitory substances (Example 13). Antimicrobial activity of *Lactobacillus* DSM 18006 has been characterized concerning the digestability by proteinase K, chymotrypsin, trypsin and protease from *Streptomyces griseus*.

The first aspect of the invention is illustrated by the following Examples 1 to 4:

Example 1

Growth Stimulation of *S. epidermidis* in an In-Vitro-Hole Plate Assay

Figure 1:
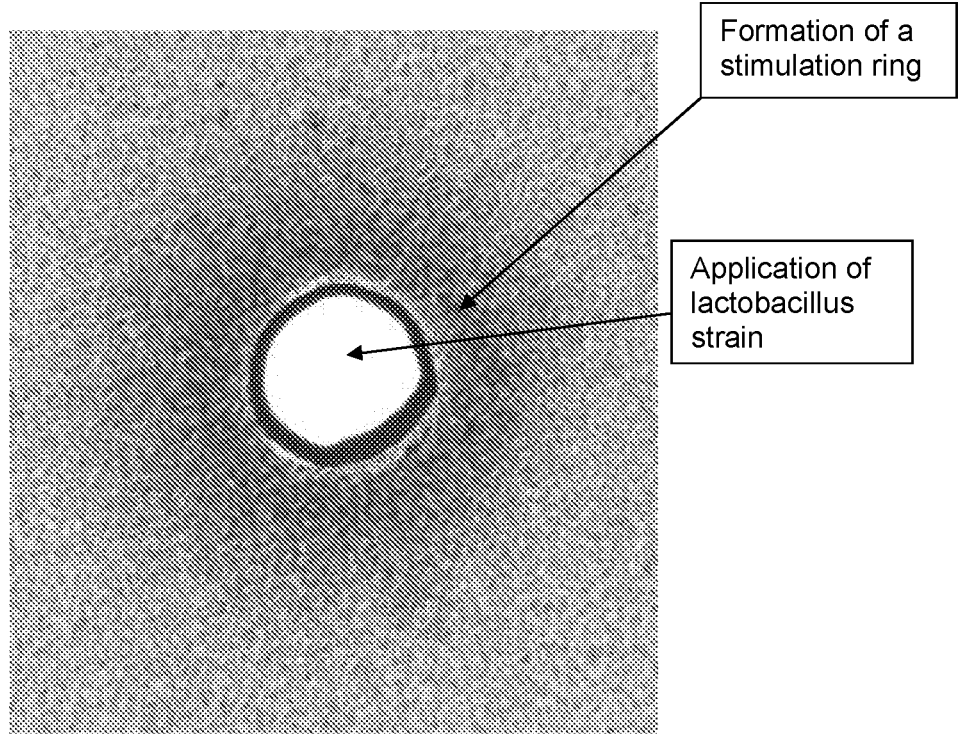
FIG. 1 shows the growth stimulation of *Staphylococcus epidermidis* in an in-vitro-hole/well plate assay (Example 1). The formation of a black ring around the well indicates growth stimulation of the indicator strain *Staphylococcus epidermidis*. Microscopically an increased number of colonies can be observed.

Specific lactic acid bacteria have been identified that are able to stimulate the growth of *Staphylococcus epidermidis* on agar plates in an in-vitro-hole plate assay. These lactic acid bacteria are described herein. To test this effect, pre-cultured lactic acid bacteria have been filled into pre-cutted holes and a growth stimulation of the Indicator strain *S. epidermidis* has been observed. To advance the visual effect of growth stimulation Tellurite has been used. Tellurite specifically stains staphylococci. Stimulance was defined as the formation of a black ring around the hole the lactic acid bacterium was pipetted in and an increase of the colony count. Data are shown in FIG. 1.

Cultivation and Preparation of Lactobacilli:

Lactic acid bacteria were cultivated from a −80° C. freezing culture in 1 ml MRS broth in Eppendorf tubes. The tubes were closed and cultivated for 2 days at 37° C. 10 µl of this preculture were transferred to the main culture consisting of 7 ml MRS broth in Falcon tubes. The culture was incubated for two days. After cultivation cells were harvested by centrifugation (15 min, 4000×g). The cell pellet was washed two times with K/Na-buffer (1 ml each). The cells were resuspended in 200 µl K/Na buffer.

Cultivation and Preparation of the Indicator Strain:

The indicator strain was *Staphylococcus epidermidis* (DSM20044). 20 ml BHI broth in a shaking glass flask were inoculated with 15 µl of a 24 h preculture. The indicator strain was cultivated for 24 h at 37° C. An aliquot was diluted to an optical density $OD_{595\ nm}$ of 0.025-0.05 in BHI-broth and 800 µl were spread on indicator plates (BHI/Tellurite). The agar was stamped using a cork borer. The holes were filled with the pre cultured lactic acid bacteria.

Media and Buffer:

| | | | |
|---|---|---|---|
| BHI-Agar | Difco Agar 1.8%; 20 ml per plate | | |
| BHI-Medium | Difco | | |
| BHI/Tellurite-Agar | like BHI-Agar, after cooling to 50° C. 1 ml of a sterile filtered 1% potassium-Tellurite solution are transferred to 100 ml BHI-Medium, 20 ml per plate | | |
| MRS-broth | Difco, 150 µl/well | | |
| K/Na-buffer | Küster Thiel, pH 7.0, autoclaved | | |
| | 0.066M $Na_2HPO_4 \times 2H_2O$ | 61.2 ml | |
| | 0.066M $KH_2PO_4$ | 38.8 ml | |

Example 2

Growth Stimulation of *Staphylococcus epidermidis* in an In-Situ-Skin Assay Probiotic lactic acid bacteria have been identified that are able to stimulate the growth of *Staphylococcus epidermidis* directly on the skin.

Figure 2:
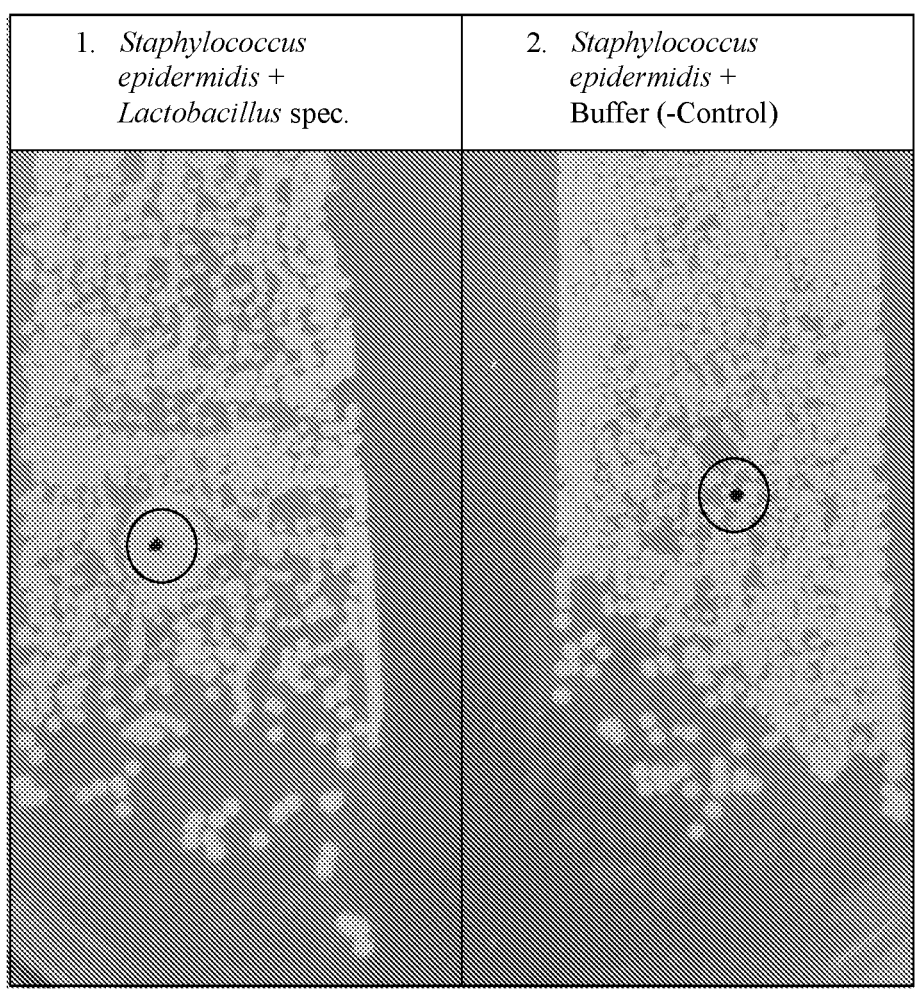
FIG. 2 shows stimulation of *Staphylococcus epidermidis* on the skin by lactobacilli. Shown are agar plates with the indicator strain *Staphylococcus epidermidis* and a *lactobacillus* strain that both have been applied to the skin. The upper skin layer has been transferred to an agar plate using an adhesive tape. By this the indicator strain has been transferred to the agar plate. The control plate does not contain the *Lactobacillus* strain.

A culture of *Staphylococcus epidermidis* was diluted and directly applied to the skin and air dried. Afterwards an aliquot of the lactic acid bacterium was applied punctual on this skin area. The indicator strain *Staphylococcus epidermidis* can be stimulated directly on the skin by the lactic acid bacterium. After incubation the staphylococci were transferred from the skin to an agar plate using an adhesive tape. The agar plate was incubated at 37° C. An increased colony count indicates a growth stimulation of the indicator strain on the skin (FIG. 2). The lactobacilli strains of the present invention, in particular those deposited with the DSMZ exhibited growth stimulation of the indicator strain as described herein.

Cultivation and Preparation of Lactobacilli:

Lactic acid bacteria were cultivated from a −80° C. freezing culture in 1 ml MRS broth in Eppendorf tubes. The tubes were closed and cultivated for 2 days at 37° C. 10 µl of this preculture were transferred to the main culture consisting of 7 ml MRS broth in Falcon tubes. The culture was incubated for two days. After cultivation cells were harvested by centrifugation (15 min, 4000×g). The cell pellet was washed two times with K/Na-buffer (1 ml each). The cells were resuspended in 200 µl K/Na buffer.

Cultivation and Preparation of the Indicator Strain:

The indicator strain was *Staphylococcus epidermidis* (DSM20044). 20 ml BHI broth in a shaking glass flask were inoculated with 15 µl of a 24 h preculture. The indicator strain was cultivated for 24 h at 37° C. An aliquot was diluted to an optical density $OD_{595\ nm}$ of 0.025-0.05 in BHI-broth. This solution was diluted again (1:100).

Media and Buffer:

| | | | |
|---|---|---|---|
| BHI-Agar | Difco Agar 1.8%; 20 ml per plate | | |
| BHI-Medium | Difco | | |
| MRS-broth | Difco, 150 µl/well | | |
| K/Na-buffer | Küster Thiel, pH 7.0, autoclaved | | |
| | 0.066M $Na_2HPO_4 \times 2H_2O$ | 61.2 ml | |
| | 0.066M $KH_2PO_4$ | 38.8 ml | |

Application of *S. epidermidis* on the Forearm:

400 µl of a 1:100 dilution of the prepared indicator strain *Staphylococcus epidermidis* was spread evenly on a defined skin area (10 cm×3 cm) and air dried.

Application of Lactobacilli on the *S. epidermidis* Inoculated Skin Area:

10 µl of prepared lactobacilli were punctually applied to the *S. epidermidis* pre-inoculated skin area. The arm was incubated for two hours in a normal environment.

Reisolation of Microorganisms from the Skin:

After 2 h the four upper skin layers were transferred to a BHI-agar plate using adhesive tape stripes. By this the isolated skin bacteria were transferred to the agar plate. The agar plates were incubated for 24 h at 37° C.

Example 3

No Growth Stimulation of *Staphylococcus aureus* in an In-Situ-Skin Assay

Using this assay it is possible to check whether unwanted bacteria of the transient, pathogenic microbial flora are not stimulated by lactic acid bacteria that are able to stimulate bacteria of the protecting resident skin microbial flora.

For this purpose the indicator strain *Staphylococcus aureus* was highly diluted and applied to the skin in the same manner as *Staphylococcus epidermidis* (see Example 2). Again the stimulating activity of lactic acid bacteria was tested. A stimulation of *Staphylococcus aureus* by the described lactic acid bacteria could not be observed. The lactobacilli strains of the present invention, in particular those deposited with the DSMZ, did not show stimulation of *Staphylococcus aureus*. Data are presented in FIG. 3.

Cultivation and Preparation of Lactobacilli:

Lactic acid bacteria were cultivated from a −80° C. freezing culture in 1 ml MRS broth in Eppendorf tubes. The tubes were closed and cultivated for 2 days at 37° C. 10 μl of this preculture were transferred to the main culture consisting of 7 ml MRS broth in Falcon tubes. The culture was incubated for two days. After cultivation cells were harvested by centrifugation (15 min, 4000×g). The cell pellet was washed two times with K/Na-buffer (1 ml each). The cells were resuspended in 200 μl K/Na buffer.

Cultivation and Preparation of the Indicator Strain:

The indicator strain was *Staphylococcus aureus* (DSM346). 20 ml BHI broth in a shaking glass flask were inoculated with 15 μl of a 24 h preculture. The indicator strain was cultivated for 24 h at 37° C. An aliquot was diluted to an optical density $OD_{595\ nm}$ of 0.025-0.05 in BHI-broth. This solution was diluted again (1:100).

Media and Buffer:

| BHI-Agar | Difco Agar 1.8%; 20 ml per plate | |
|---|---|---|
| BHI-Medium | Difco | |
| MRS-broth | Difco, 150 μl/well | |
| K/Na-buffer | Küster Thiel, pH 7.0, autoclaved | |
| | 0.066M $Na_2HPO_4 \times 2H_2O$ | 61.2 ml |
| | 0.066M $KH_2PO_4$ | 38.8 ml |

Application of *Staphylococcus aureus* on the Forearm:

400 μl of a 1:100 dilution of the prepared indicator strain *Staphylococcus aureus* was spread evenly on a defined skin area (10 cm×3 cm) and air dried.

Application of Lactobacilli on the *S. aureus* Inoculated Skin Area:

10 μl of prepared lactobacilli were punctually applied to the *S. aureus* pre-inoculated skin area. The arm was incubated for two hours in a normal environment.

Figure 3:
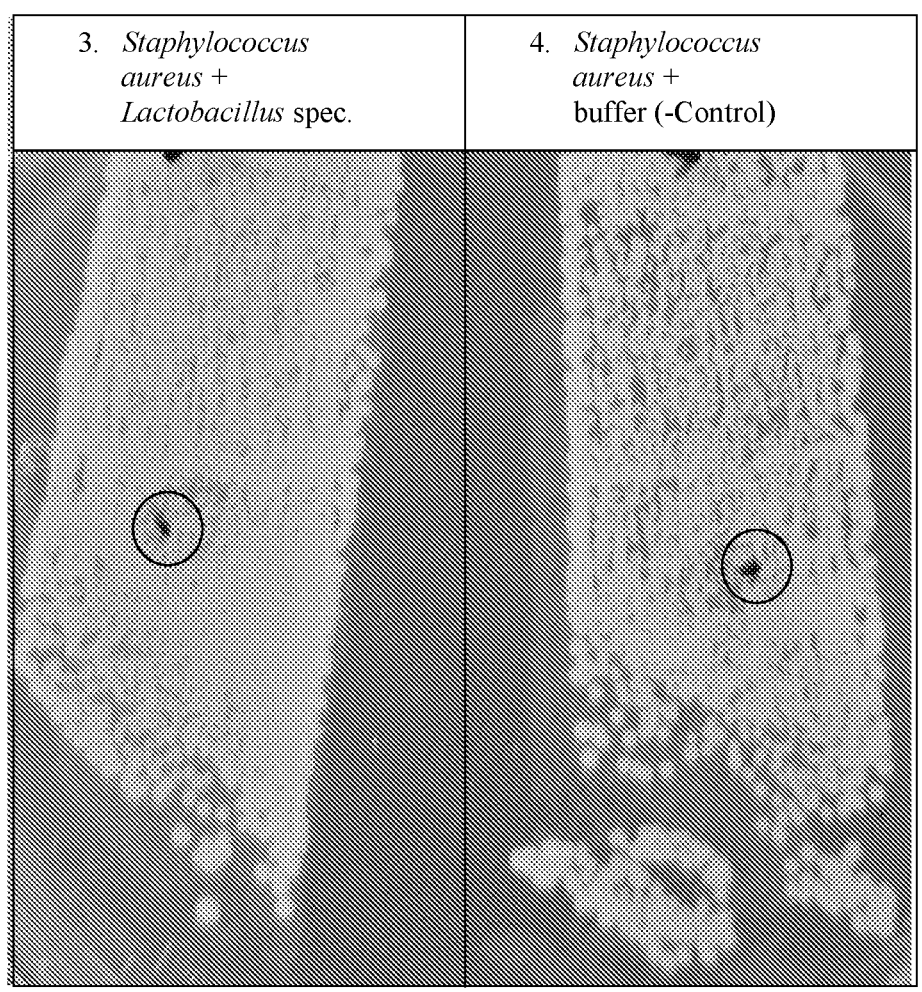
FIG. 3 shows the lack of stimulation of *Staphylococcus aureus* on the skin by lactobacilli. Shown are agar plates with the indicator strain *Staphylococcus aureus* and a *lactobacillus* strain that both have been applied to the skin. The upper skin layer has been transferred to an agar plate using an adhesive tape. By this the indicator strain has been transferred to the agar plate. The control plate does not contain the *lactobacillus* strain.

Reisolation of Microorganisms from the Skin:

After 2 h the four upper skin layers were transferred to a BHI-agar plate using adhesive tape stripes. By this the isolated skin bacteria were transferred to the agar plate. The agar plates were incubated for 24 h at 37° C. The data are shown in FIG. 3.

Example 4

No Growth Stimulation of *S. aureus* in an In-Vitro-Hole Plate Assay

Figure 4:
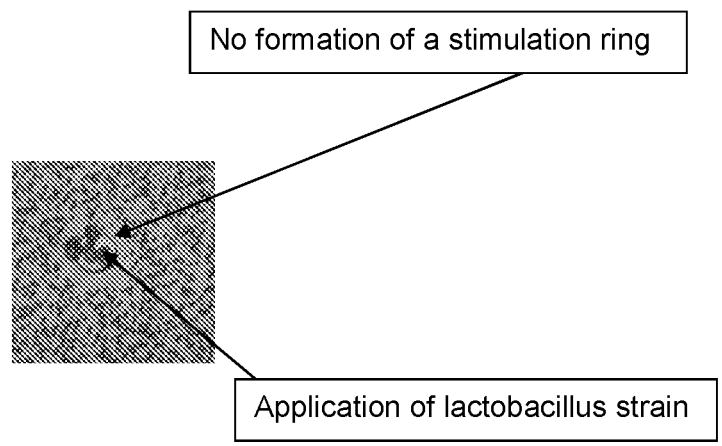
FIG. 4 shows the lack of stimulation of *Staphylococcus aureus* in an in-vitro-hole/well plate assay (Example 4). No formation of a black ring with increased cell density around the well can be observed. This indicates that the indicator strain is not stimulated by the *lactobacillus*.

Specific lactic acid bacteria have been identified that are able to stimulate the growth of *Staphylococcus epidermidis* on agar plates in an in-vitro-hole plate assay but not the representative of the transient microbial skin flora *Staphylococcus aureus*. To test this effect, precultured lactic acid bacteria that are able to stimulate *Staphylococcus epidermidis* have been filled into pre-cutted holes and absence of growth stimulation of the indictator strain *S. aureus* has been observed. To advance the visual effect of growth stimulation tellurite has been used. Tellurite specifically stains staphylococci. Stimulance was defined as the formation of a black ring around the hole containing the lactic acid bacterium and an increase of the colony count. The lactobacilli strains of the present invention, in particular those deposited with the DSMZ did not show stimulation of *Staphylococcus aureus*. Data are shown in FIG. 4.

Cultivation and Preparation of Lactobacilli:

Lactic acid bacteria were cultivated from a −80° C. freezing culture in 1 ml MRS broth in Eppendorf tubes. The tubes were closed and cultivated for 2 days at 37° C. 10 μl of this preculture were transferred to the main culture consisting of 7 ml MRS broth in Falcon tubes. The culture was incubated for two days. After cultivation cells were harvested by centrifugation (15 min, 4000×g). The cell pellet was washed two times with K/Na-buffer (1 ml each). Cells were resuspended in 200 μl K/Na buffer.

Cultivation and Preparation of the Indicator Strain:

The indicator strain was *Staphylococcus aureus* (DSM346). 20 ml BHI broth in a shaking glass flask were inoculated with 15 μl of a 24 h preculture. The indicator strain was cultivated for 24 h at 37° C. An aliquot was diluted to an optical density $OD_{595\ nm}$ of 0.025-0.05 in BHI-broth and 800 μl were spread on indicator plates (BHI/Tellurite). The agar was stamped using a cork borer. The holes were filled with the pre cultured lactic acid bacteria.

Media and Buffer:

| BHI-Agar | Difco Agar 1.8%; 20 ml per plate | |
|---|---|---|
| BHI-Medium | Difco | |
| BHI/Tellurite-Agar | like BHI-Agar, after cooling to 50° C. 1 ml of a filter sterilized 1% potassium-Tellurite solution are transferred to 100 ml BHI-Medium, 20 ml are distributed per plate | |
| MRS-broth | Difco, 150 μl/well | |
| K/Na-buffer | Küster Thiel, pH 7.0, autoclaved | |
| | 0.066M $Na_2HPO_4 \times 2H_2O$ | 61.2 ml |
| | 0.066M $KH_2PO_4$ | 38.8 ml |

The second aspect of the invention is illustrated by the following Examples 5 to 13:

Example 5

Growth Inhibition of *S. aureus* in an In Vitro Hole Plate Assay

Specific lactic acid bacteria have been identified, that are able to specifically inhibit the growth of *Staphylococcus aureus* on agar plates in an in vitro hole plate assay. To test this effect, pre cultured lactic acid bacteria have been filled into pre-cutted holes and a growth inhibition of the indicator strain *S. aureus* has been observed. Data are shown in FIG. 5.

Cultivation and Preparation of Lactobacilli:

Lactic acid bacteria were cultivated (OB-LB-Sa3; DSM 18006) from a −80° C. freezing culture in 1 ml MRS broth in eppendorf tubes. Tubes were closed and cultivated for 2 days at 37° C. 10 μl of this pre culture was transferred to the main culture consisting of 7 ml MRS broth in falcon tubes. The culture was incubated for 2 days. After cultivation cells were harvested by centrifugation (15 min, 4000×g). The cell pellet was washed two times with K/Na-buffer (each 1 ml). Cells were resuspended in 200 μl K/Na buffer.

Cultivation and Preparation of the Indicator Strain:

The indicator strain was *Staphylococcus aureus* (DSM346). 20 ml BHI broth in a shaking glass flask were inoculated with 15 μl of a 24 h pre culture. The indicator strain was cultivated for 24 h at 37° C. An aliquot was diluted to an optical density $OD_{595\ nm}$ of 0.025-0.05 in BHI-broth and 800 μl spread on indicator plates (BHI). The agar was stamped using a cork borer. The holes were filled with 5 μl or 10 μl of the pre cultured lactic acid bacteria.

Media and Buffer:

| BHI-Agar | Difco Agar 1.8%; 20 ml per plate | |
|---|---|---|
| BHI-Medium | Difco | |
| MRS-broth | Difco | |
| K/Na-buffer | according to Küster Thiel, pH 7.0, autoclaved | |
| | 0.066M $Na_2HPO_4 \times 2H_2O$ | 61.2 ml |
| | 0.066M $KH_2PO_4$ | 38.8 ml |

Example 6

Growth Inhibition of *S. aureus* in an In Vitro Liquid Assay

Specific lactic acid bacteria have been identified, that are able to specifically inhibit the growth of *Staphylococcus aureus* in liquid medium in an in vitro liquid assay. To test this effect, pre cultured lactic acid bacteria have been co-incubated with the indictator strain *S. aureus* in liquid cultivation medium, optimized for the growth of Staphylococci. The degree of inhibition was quantified by counting the colony forming units of the indicator strain in comparison to the control without lactic acid bacteria. Data are shown in FIG. 6.

Cultivation and Preparation of Lactobacilli:

Lactic acid bacteria were cultivated (OB-LB-Sa3; DSM 18006) from a −80° C. freezing culture in 1 ml MRS broth in eppendorf tubes. Tubes was closed and cultivated for 2 days at 37° C. 10 µl of this pre culture was transferred to the main culture consisting of 7 ml MRS broth in falcon tubes. The culture was incubated for 2 days. After cultivation cells were harvested by centrifugation (15 min, 4000×g). The cell pellet was washed two times with K/Na-buffer (each 1 ml). Cells were resuspended in 200 µl K/Na buffer with 250 mM glycerol and incubated for 17 h.

Cultivation and Preparation of the Indicator Strain:

The indicator strain was *Staphylococcus aureus* (DSM346). 10 ml BHI broth in a shaking glass flask were inoculated with 15 µl of a freezing culture for a 24 h pre culture. The culture was diluted with fresh BHI broth to a cell concentration of 2.5×10⁸ cells/ml.

Liquid Inhibition Assay

For the liquid assay 5 µl of the freshly prepared lactic acid bacteria (out of 200 µl) and 10 µl of the pre cultured indicator strain *S. aureus* were inoculated for a co-cultivation in 10 ml of BHI broth. The culture was incubated for 7 h. Afterwards 100 µl of a 1:10000 dilution was spread on a BHI agar plate for quantification of the colony forming units. The plate was incubated for 24 h hours and the colony forming units were counted.

Media and Buffer:

| BHI-Agar | Difco Agar 1.8%; 20 ml per plate | |
|---|---|---|
| BHI-Medium | Difco | |
| MRS-broth | Difco | |
| K/Na-buffer | according to Küster Thiel, pH 7.0, autoclaved | |
| | 0.066M $Na_2HPO_4 \times 2H_2O$ | 61.2 ml |
| | 0.066M $KH_2PO_4$ | 38.8 ml |

Example 7

No Growth Inhibition of *Staphylococcus epidermidis* an In Vitro Liquid Assay

Using this assay it was possible to check whether selected lactic acid bacteria that were able to inhibit the growth of the pathogenic microorganism *Staphylococcus aureus* did not inhibit the major member of the commensal micro flora of the skin, *Staphylococcus epidermidis* in an in vitro liquid assay.

To test this effect, pre cultured lactic acid bacteria have been co-incubated with the indicator strain in a liquid culture. The degree of inhibition was quantified by counting the colony forming units of both indicator strains in comparison to the control without lactic acid bacteria. Data are shown in FIG. 7.

Cultivation and Preparation of Lactobacilli:

Lactic acid bacteria were cultivated (OB-LB-Sa3; DSM 18006) from a −80° C. freezing culture in 1 ml MRS broth in eppendorf tubes. Tubes were closed and cultivated for 2 days at 37° C. 10 µl of this pre culture was transferred to the main culture consisting of 7 ml MRS broth in falcon tubes. The culture was incubated for 2 days. After cultivation cells were harvested by centrifugation (15 min, 4000×g). The cell pellet was washed two times with K/Na-buffer (each 1 ml). Cells were resuspended in 200 µl K/Na buffer with 250 mM glycerol and incubated for 17 h.

Cultivation and Preparation of the Indicator Strain:

The indicator strain was *Staphylococcus epidermidis* (DSM20044). 20 ml BHI broth in a shaking glass flask was inoculated with 15 µl of a freezing culture for a 24 h pre culture.

Liquid Inhibition Assay

For the liquid assay 5 µl of the freshly prepared lactic acid bacteria (out of 200 µl) and 10 µl of the pre cultured indicator strain *S. epidermidis* were inoculated for a co-cultivation in 10 ml of BHI broth. The culture was incubated for 7 h. Afterwards 100 µl of a 1:10000 dilution was spread on a BHI agar plate for quantification of the colony forming units. The plate was incubated for 24 h hours and the colony forming units were counted.

Media and Buffer:

| BHI-Agar | Difco Agar 1.8%; 20 ml per plate | |
|---|---|---|
| BHI-Medium | Difco | |
| MRS-broth | Difco | |
| K/Na-buffer | according to Küster Thiel, pH 7.0, autoclaved | |
| | 0.066M $Na_2HPO_4 \times 2H_2O$ | 61.2 ml |
| | 0.066M $KH_2PO_4$ | 38.8 ml |

Example 8

Growth Inhibition of *Staphylococcus aureus* in an In Situ Skin Assay

Lactic acid bacteria have been identified that are able to inhibit the growth of *S. aureus* directly on the skin.

To test this effect, a culture of *Staphylococcus aureus* was diluted and directly applied to the skin and air dried. Afterwards an aliquot of the lactic acid bacterium was applied on this skin area. Thus the indicator strain *Staphylococcus aureus* was inhibited directly on the skin by the lactic acid bacterium. After incubation the staphylococci were transferred from the skin to an agar plate using in an adhesive tape. The agar plate was incubated at 37° C. A decreased colony count in comparison to the control without lactic acid bacteria indicates a growth inhibition of the indicator strain on the skin.

Cultivation and Preparation of Lactobacilli:

Lactic acid bacteria were cultivated (OB-LB-Sa3; DSM 18006) from a −80° C. freezing culture in 1 ml MRS broth in eppendorf tubes. Tubes were closed and cultivated for 2 days at 37° C. 10 µl of this pre culture were transferred to the main culture consisting of 7 ml MRS broth in falcon tubes. The culture was incubated for 2 days. After cultivation cells were harvested by centrifugation (15 min, 4000×g). The cell pellet was washed two times with K/Na-buffer (each 1 ml). Cells are resuspended in 200 µl K/Na buffer.

Cultivation and Preparation of the Indicator Strain:

The indicator strain was *Staphylococcus aureus* (DSM346). 20 ml BHI broth in a shaking glass flask were inoculated with 15 µl of a 24 h pre culture. The indicator strain was cultivated for 24 h at 37° C.

Media and Buffer:

| BHI-Agar | Difco Agar 1.8%; 20 ml per plate | |
|---|---|---|
| BHI-Medium | Difco | |
| MRS-broth | Difco | |
| K/Na-buffer | Küster Thiel, pH 7.0, autoclaved | |
| | 0.066M $Na_2HPO_4 \times 2H_2O$ | 61.2 ml |
| | 0.066M $KH_2PO_4$ | 38.8 ml |

Application of *S. aureus* on the Forearm:

400 µl of an 1:100 dilution of the prepared indicator strain *Staphylococcus aureus* was spread consistently on a defined skin area (10 cm×3 cm) and air dried.

Application of Lactobacilli on the *S. aureus* Inoculated Skin Area:

10 µl of prepared lactobacilli was applied to the *S. aureus* pre-inoculated skin area. The arm was incubated for six hours in a normal environment.

Reisolation of Microorganisms from the Skin:

After 6 h the four upper skin layers were transferred to a BHI-agar plate using adhesive tape stripes. Thus the isolated skin bacteria were transferred to the agar plate. Agar plates were incubated for 24 h at 37° C.

Example 9

No Growth Inhibition of *Staphylococcus epidermidis* in an In Situ Skin Assay

Lactic acid bacteria have been identified that inhibit the growth of *Staphylococcus aureus*, while the growth of *Staphylococcus epidermidis* is not affected directly on the skin.

Using this assay it was possible to check if the commensal microorganism *Staphylococcus epidermidis* of the healthy normal skin flora was not inhibited by lactic acid bacteria that are able to inhibit *Staphylococcus aureus*.

Therefore the indicator strain *Staphylococcus epidermidis* was applied highly diluted to the skin in the same manner as *Staphylococcus aureus*. Again the inhibiting activity of lactic acid bacteria was tested. An inhibition of *Staphylococcus epidermidis* has not been observed with the described lactic acid bacteria.

Cultivation and Preparation of Lactobacilli:

Lactic acid bacteria were cultivated (OB-LB-Sa3; DSM 18006) from a −80° C. freezing culture in 1 ml MRS broth in eppendorf tubes. Tubes were closed and cultivated for 2 days at 37° C. 10 µl of this pre culture was transferred to the main culture consisting of 7 ml MRS broth in falcon tubes. The culture was incubated for 2 days. After cultivation cells were harvested by centrifugation (15 min, 4000×g). The cell pellet was washed two times with K/Na-buffer (each 1 ml). Cells are resuspended in 200 µl K/Na buffer.

Cultivation and Preparation of the Indicator Strain:

The indicator strain was *Staphylococcus epidermidis* (DSM20044). 20 ml BHI broth in a shaking glass flask were inoculated with 15 µl of a 24 h pre culture. The indicator strain was cultivated for 24 h at 37° C.

Media and Buffer:

| BHI-Agar | Difco Agar 1.8%; 20 ml per plate | |
|---|---|---|
| BHI-Medium | Difco | |
| MRS-broth | Difco | |
| K/Na-buffer | Küster Thiel, pH 7.0, autoclaved | |
| | 0.066M $Na_2HPO_4 \times 2H_2O$ | 61.2 ml |
| | 0.066M $KH_2PO_4$ | 38.8 ml |

Application of *Staphylococcus epidermidis* on the Forearm:

400 µl of a 1:100 dilution of the prepared indicator strain *Staphylococcus epidermidis* was spread consistently on a defined skin area (10 cm×3 cm) and air dried.

Application of Lactobacilli on the *S. epidermidis* Inoculated Skin Area:

10 µl of prepared lactobacilli were applied to the *S. epidermidis* pre-inoculated skin area. The arm was incubated for six hours in a normal environment.

Reisolation of Microorganisms from the Skin:

After 6 h the four upper skin layers was transferred to a BHI-agar plate using adhesive tape stripes. Thus the isolated skin bacteria are transferred to the agar plate. Agar plates are incubated for 24 h at 37° C.

Example 10

No Growth Inhibition of *Micrococcus luteus* in the In-Vitro-Liquid Assay

The selected lactic acid bacteria that are able to inhibit the growth of the pathogenic microorganism *Staphylococcus aureus* do not inhibit the relevant member of the commensal micro flora of the skin, *Micrococcus luteus* in an in vitro liquid assay.

To test this effect, pre cultured lactic acid bacteria have been co-incubated with the indictator strain in a liquid culture. The degree of inhibition was quantified by counting the colony forming units of both indicator strains in comparison to the control without lactic acid bacteria. Data are shown in FIG. 8.

Cultivation and Preparation of Lactobacilli:

Lactic acid bacteria were cultivated (OB-LB-Sa3; DSM 18006 and OB-LB-Sa16; DSM 18007) from a −80° C. freezing culture in 1 ml MRS broth in eppendorf tubes. Tubes were closed and cultivated for 2 days at 37° C. 10 µl of this pre culture was transferred to the main culture consisting of 7 ml MRS broth in falcon tubes. The culture was incubated for 2 days. After cultivation cells were harvested by centrifugation (15 min, 4000×g). The cell pellet was washed two times with K/Na-buffer (each 1 ml). Cells were resuspended in 200 µl K/Na buffer with 250 mM glycerol and incubated for 17 h.

Cultivation and Preparation of the Indicator Strain:

The indicator strain was *Micrococcus luteus*. 20 ml BHI broth in a shaking glass flask was inoculated with 15 µl of a freezing culture for a 24 h pre culture.

Liquid Inhibition Assay:

For the liquid assay 5 µl of the freshly prepared lactic acid bacteria (out of 200 µl) and 10 µl of the pre cultured indicator strain *M. luteus* were inoculated for a co-cultivation in 10 ml of BHI broth. The culture was incubated for 7 h. Afterwards 100 µl of a 1:1000 dilution was spread on a BHI agar plate for quantification of the colony forming units. The plate was incubated for 24 h and the colony forming units were counted.

Media and Buffer:

| | |
|---|---|
| BHI-Agar | Difco Agar 1.8%; 20 ml per plate |
| BHI-Medium | Difco |
| MRS-broth | Difco |
| K/Na-buffer | according to Küster Thiel, pH 7.0, autoclaved |
| | 0.066M $Na_2HPO_4 \times 2H_2O$  61.2 ml |
| | 0.066M $KH_2PO_4$  38.8 ml |

Example 11

No Growth Inhibition of Escherichia coli in the In-Vitro-Liquid Assay

The selected lactic acid bacteria that are able to inhibit the growth of the pathogenic microorganism Staphylococcus aureus do not inhibit other human relevant microorganisms, e.g Escherichia coli in an in vitro liquid assay.

To test this effect, pre cultured lactic acid bacteria have been co-incubated with the indicator strain in liquid culture. The degree of inhibition was quantified by counting the colony forming units of both indicator strains in comparison to the control without lactic acid bacteria. Data are shown in FIG. 9.

Cultivation and Preparation of Lactobacilli:

Lactic acid bacteria were cultivated (OB-LB-Sa3; DSM 18006 and OB-LB-Sa16; DSM 18007) from a −80° C. freezing culture in 1 ml MRS broth in eppendorf tubes. Tubes were closed and cultivated for 2 days at 37° C. 10 µl of this pre culture was transferred to the main culture consisting of 7 ml MRS broth in falcon tubes. The culture was incubated for 2 days. After cultivation cells were harvested by centrifugation (15 min, 4000×g). The cell pellet was washed two times with K/Na-buffer (each 1 ml). Cells were resuspended in 200 µl K/Na buffer with 250 mM glycerol and incubated for 17 h.

Cultivation and Preparation of the Indicator Strain:

The indicator strain was Escherichia coli. 20 ml BHI broth in a shaking glass flask was inoculated with 15 µl of a freezing culture for a 24 h pre culture.

Liquid Inhibition Assay:

For the liquid assay 5 µl of the freshly prepared lactic acid bacteria (out of 200 µl) and 10 µl of the pre cultured indicator strain E. coli were inoculated for a co-cultivation in 10 ml of BHI broth. The culture was incubated for 7 h. Afterwards 100 µl of a 1:1000 dilution was spread on a BHI agar plate for quantification of the colony forming units. The plate was incubated for 24 h and the colony forming units were counted.

Media and Buffer:

| | |
|---|---|
| BHI-Agar | Difco Agar 1.8%; 20 ml per plate |
| BHI-Medium | Difco |
| MRS-broth | Difco |
| K/Na-buffer | according to Küster Thiel, pH 7.0, autoclaved |
| | 0.066M $Na_2HPO_4 \times 2H_2O$  61.2 ml |
| | 0.066M $KH_2PO_4$  38.8 ml |

Example 12

Degree of Growth Inhibition of S. aureus in an In-Vitro-Hole Plate Assay in Comparison to Bacitracin and Erythromycin Specific lactic acid bacteria have been identified, that are able to specifically inhibit the growth of Staphylococcus aureus on agar plates in an in-vitro-hole plate assay. This effect has been compared to commercial antibiotic cream preparations of bacitracin and erythromycin. To compare this effect, both antibiotics have been filled into pre-cutted holes at different concentrations and a growth inhibition of the indictator strain S. aureus has been observed (calibration curves in FIG. 10A). The diameter of the inhibition zones has been measured and the area of inhibition has been calculated thereof. Afterwards this area has been correlated to the growth inhibition of S. aureus by defined numbers of precultured Lactobacillus cells of strain OB-LB-Sa3 (DSM 18006) (see FIG. 10B).

Cultivation and Preparation of Lactobacilli:

Lactic acid bacteria were cultivated (OB-LB-Sa3; DSM 18006) from a −80° C. freezing culture in 1 ml MRS broth in eppendorf tubes. Tubes were closed and cultivated for 2 days at 37° C. 10 µl of this pre culture was transferred to the main culture consisting of 7 ml MRS broth in falcon tubes. The culture was incubated for 2 days. After cultivation cells were harvested by centrifugation (15 min, 4000×g). The cell pellet was washed two times with K/Na-buffer (each 1 ml). Cells were resuspended in 200 µl K/Na buffer.

Cultivation and Preparation of the Indicator Strain:

The indicator strain was Staphylococcus aureus (DSM346). 20 ml BHI broth in a shaking glass flask were inoculated with 15 µl of a 24 h pre culture. The indicator strain was cultivated for 24 h at 37° C. An aliquot was diluted to an optical density $OD_{595\ nm}$ of 0.025-0.05 in BHI-broth and 800 µl spread on indicator plates (BHI). The agar was stamped using a cork borer. The holes were filled with 5 µl or 10 µl of the pre cultured lactic acid bacteria or corresponding volumes of commercial antibiotic preparations.

Media and Buffer:

| | |
|---|---|
| BHI-Agar | Difco Agar 1.8%; 20 ml per plate |
| BHI-Medium | Difco |
| MRS-broth | Difco |
| K/Na-buffer | according to Küster Thiel, pH 7.0, autoclaved |
| | 0.066M $Na_2HPO_4 \times 2H_2O$  61.2 ml |
| | 0.066M $KH_2PO_4$  38.8 ml |

Example 13

Protease Stability of Lactobacillus Inhibitory Substance

Specific lactic acid bacteria have been identified, that are able to specifically inhibit the growth of Staphylococcus aureus on agar plates in an in-vitro-hole plate assay.

The antimicrobial activity of selected lactobacilli has been characterized concerning digestibility by proteinase K, proteas from Streptomyces griseus, chymotrypsin and trypsin. Cell free preparations of Lactobacillus supernatants have been prepared and incubated with different proteases for 1 h at 37° C. Afterwards these preparations have been tested for their ability to inhibit the growth of the indicator strain S.

*aureus*. The diameter of the inhibition zones has been measured and the area of inhibition has been calculated thereof (see FIG. 11).

Cultivation and Preparation of Lactobacilli:

Lactic acid bacteria were cultivated (OB-LB-Sa3; DSM 18006) from a −80° C. freezing culture in 7 ml MRS broth in falcon tubes. Tubes were closed and cultivated for 2 days at 37° C. 7 ml of this pre culture was transferred to the main culture consisting of 40 ml MRS broth in flasks. The culture was incubated for 2 days. After cultivation cells were harvested by centrifugation (15 min, 4000×g). The cell pellet was washed two times with K/Na-buffer (each 2 ml). Cells were resuspended in 10 ml BHI medium and incubated for 6 h at 37° C. Cells were harvested by centrifugation (15 min, 4000×g) and the supernatant was used for protease incubation. In detail, 150 µl of the supernatant was incubated with 15 µl of a 10 mg/ml protease solution at 37° C.

Cultivation and Preparation of the Indicator Strain:

The indicator strain was *Staphylococcus aureus* (DSM346). 20 ml BHI broth in a shaking glass flask were inoculated with 15 µl of a 24 h pre culture. The indicator strain was cultivated for 24 h at 37° C. An aliquot was diluted to an optical density $OD_{595\ nm}$ of 0.025-0.05 in BHI-broth and 800 µl spread on indicator plates (BHI). The agar was stamped using a cork borer. The holes were filled with 5 µl or 10 µl of the pre cultured cells and was incubated with 15 µl of a 10 mg/ml protease solution at 37° C. for 1 h. Afterwards 5 µl or 10 µl of the protease treated *lactobacillus* supernatant was used for the inhibition assay Media and Buffer:

| | |
|---|---|
| BHI-Agar | Difco Agar 1.8%; 20 ml per plate |
| BHI-Medium | Difco |
| MRS-broth | Difco |
| K/Na-buffer | according to Küster Thiel, pH 7.0, autoclaved |
| | 0.066M $Na_2HPO_4 \times 2H_2O$   61.2 ml |
| | 0.066M $KH_2PO_4$   38.8 ml |

CITED REFERENCES

Aly, R., Maibach, H I., Shinefield, H R., Strauss, W G. (1972): Survival of pathogenic microorganisms on human skin. J Invest Dermatol. 58(4): 205-210.

Bisno, A L. (1984): Cutaneous infections: microbiologic and epidemiologic considerations. Am J Med. 76(5A): 172-179.

Brook, I. (2000): The effects of amoxicillin therapy on skin flora in infants. Pediatr Dermatol. 17(5): 360-363.

Elek, S D. (1956): Experimental staphylococcal infections in the skin of man. Ann. NY Acad Sci. 65: 85-90.

Feingold, D S. (1985): Cutaneous microbial flora. Cutis. 36(5A): 1.

Gfatter, R., Hackl, P., Braun, F. (1997): Effects of soap and detergents on skin surface pH, stratum corneum hydration and fat content in infants. Dermatology. 195(3): 258-262.

Gibbons, R J., Houte, J V. (1975): Bacterial adherence in oral microbial ecology. Annu Rev Microbiol. 1975; 29: 19-44.

Hurst, V. (1959): Transmission of hospital staphylococci among newborn infants. Pediatrics 25: 204-214.

Imokawa, G., Akasaki, S., Hattori, M., Yoshizuka, N. (1986): Selective recovery of deranged water-holding properties by stratum corneum lipids. J Invest Dermatol. 87(6): 758-761.

Korting, H C. (1992): Einfluß des pH-Wertes auf das Wachstum von *Staphylococcus epidermidis, Staphylococcus aureus* und *Propionibacterium acnes* in kontinuierlicher Kultur. Zbl. Hyg. 193: 78-90.

Korting, H C., Hübner, K., Greiner, K., Hamm, G., Braun-Falco, O. (1990): Unterschiede des Hautoberflachen-pH-Wertes und der bakteriellen Mikroflora durch Langzeit-Anwendung synthetische Detergenz-Zubereitungen mit pH 5,5 und pH 7,0 in Acta Derm Venereol. 70: 429-457.

Larson, E. (2001): Hygiene of the skin: when is clean too clean? Emerg Infect Dis. 7(2): 225-230.

Leyden, J J., McGinley, K J., Nordstrom, K M., Webster, G F. (1987): Skin microflora. J Invest Dermatol. 88(3): 65-72.

Lukas, A. (1990): Beeinflußbarkeit des Wachstums wichtiger Bakterien der Residentflora in-vitro durch den pH-Wert. In: O. Braun-Falco, H C. Korting (Hrsg.): Hautreinigung mit Syndets, 104-112.

Milyani, R M., Selwyn, S. (1978): Quantitative studies on competitive activities of skin bacteria growing on solid media. J Med Microbiol. 11(4): 379-386.

Ohnishi, Y., Okino, N., Ito, M., Imayama, S. (1999): Ceramidase activity in bacterial skin flora as a possible cause of ceramide deficiency in atopic dermatitis. Clin Diagn Lab Immunol. 6(1): 101-104.

Roth, R R., James, W D. (1988): Microbial ecology of the skin. Annu Rev Microbiol. 42: 441-464.

Selwyn, S., Ellis, H. (1972): Skin bacteria and skin disinfection reconsidered. Br Med J. 1(793): 136-140.

Sullivan, A., Edlund, C., Nord, C E. (2001): Effect of antimicrobial agents on the ecological balance of human micro flora. Lancet Infect Dis. 1(2): 101-114.

Yosipovitch, G., Maibach, H I. (1996): Skin surface pH: A protective acid mantle in Cosmetics Toiletries magazine 111 (12): 101

The invention claimed is:

1. A method for the prophylaxis or treatment of skin against transient pathogenic micro flora, the method comprising administering to an individual in need thereof a prophylactically or therapeutically effective amount of a cosmetic or pharmaceutical composition, wherein the composition comprises a microorganism which is able to stimulate the growth of one or more microorganisms of the resident skin microbial flora and which does not stimulate the growth of microorganisms of the transient pathogenic micro flora, and wherein said microorganism is selected from a *Lactobacillus paracasei* having DSMZ accession number DSM 17248, a *Lactobacillus brevis* having DSMZ accession number DSM 17247, a *Lactobacillus brevis* having DSMZ accession number DSM 17250 and a *Lactobacillus fermentum* having DSMZ accession number DSM 17249.

2. The method of claim 1, wherein said microorganism is able to stimulate the growth of *Staphylococcus epidermidis*.

3. The method of claim 2, wherein stimulation of the growth of *Staphylococcus epidermidis* is measured in an in situ skin assay.

4. The method of claim 1, wherein said microorganism does not stimulate the growth of *Staphylococcus aureus*.

5. The method of claim 1, wherein said microorganism is in an inactive form.

6. The method of claim 5, wherein in said microorganism is thermally inactivated or lyophilized.

7. The method of claim 1, wherein the composition comprises a cosmetically acceptable carrier or excipient.

8. The method of claim 1, wherein the composition comprises a pharmaceutically acceptable carrier or excipient.

9. The method of claim 1, wherein the method is the prophylaxis or treatment of dermatitis.

10. The method of claim 9, wherein the dermatitis is atopic dermatitis, psoriasis, poison-ivy dermatitis, eczema herpeticum, kerion or scabies.

11. The method of claim 1, wherein the individual is a human.

12. The method of claim 1, wherein the microorganism is isolated.

13. The method of claim 1, wherein the composition comprises the microorganism in an amount between $10^3$ and $10^8$ cells per mg in solid form, or between $10^2$ and $10^{13}$ cells per mL in liquid form.

14. The method of claim 1, wherein the composition is administered topically.

15. A method of preventing or treating dermatitis, the method comprising administering to a patient in need thereof a prophylactically or therapeutically effective amount of a cosmetic or pharmaceutical composition, wherein the composition comprises an isolated microorganism selected from a *Lactobacillus paracasei* having DSMZ accession number DSM 17248, a *Lactobacillus brevis* having DSMZ accession number DSM 17247, a *Lactobacillus brevis* having DSMZ accession number DSM 17250 and a *Lactobacillus fermentum* having DSMZ accession number DSM 17249, and wherein said microorganism has the ability to stimulate the growth of at least one microorganism of the resident skin microbial flora and does not stimulate the growth of microorganisms of the transient pathogenic micro flora.

16. The method of claim 15, wherein said microorganism is in an inactive form.

17. The method of claim 15, wherein the composition is administered topically.

18. The method of claim 15, wherein said microorganism is able to stimulate the growth of *Staphylococcus epidermidis*, and wherein said microorganism does not stimulate the growth of *Staphylococcus aureus*.

19. The method of claim 1, wherein said microorganism is able to stimulate the growth of *Staphylococcus epidermidis*, and wherein said microorganism does not stimulate the growth of *Staphylococcus aureus*.

* * * * *